United States Patent [19]
Kensil et al.

[11] Patent Number: 5,583,112
[45] Date of Patent: Dec. 10, 1996

[54] SAPONIN-ANTIGEN CONJUGATES AND THE USE THEREOF

[75] Inventors: Charlotte A. Kensil, Milford; Sean Soltysik, Worcester; Dante J. Marciani, Hopkinton, all of Mass.

[73] Assignee: Cambridge Biotech Corporation, Worcester, Mass.

[21] Appl. No.: 906,880

[22] Filed: Jul. 2, 1992

Related U.S. Application Data

[63] Continuation-in-part of Ser. No. 762,754, Sep. 18, 1991, abandoned, which is a continuation-in-part of Ser. No. 573,268, Aug. 27, 1990, Pat. No. 5,057,540, which is a continuation of Ser. No. 200,754, May 31, 1988, abandoned, which is a continuation-in-part of Ser. No. 55,229, May 29, 1987, abandoned.

[51] Int. Cl.$^6$ .................. A61K 31/115; A61K 31/70; A61K 31/705; A61K 39/10
[52] U.S. Cl. .................. 514/25; 514/23; 514/26; 514/53; 514/54; 514/61; 530/395; 424/184.1; 424/278.1; 424/194.1; 424/197.11; 536/5; 536/4.1; 536/6.1; 536/6
[58] Field of Search .................. 536/5, 6.1, 4.1, 536/6; 514/23, 26, 25, 53, 54, 61; 530/395; 424/88, 89, 91, 92, 184.1, 278.1, 194.1, 197.11

[56] References Cited

U.S. PATENT DOCUMENTS

| | | | |
|---|---|---|---|
| 4,335,113 | 6/1982 | Combier et al. | 424/180 |
| 4,432,969 | 2/1984 | Batchelor | 424/91 |
| 4,524,067 | 6/1985 | Arichi et al. | 514/33 |
| 4,578,269 | 3/1986 | Morein | 424/88 |
| 4,744,983 | 5/1988 | Morein | 424/88 |
| 4,788,056 | 11/1988 | Lütticken et al. | 424/89 |
| 4,789,702 | 12/1988 | Nunberg | 530/324 |
| 4,789,735 | 12/1988 | Frank et al. | 530/395 |
| 4,900,549 | 2/1990 | De Vries et al. | 424/88 |
| 4,981,684 | 1/1991 | MacKenzie et al. | 424/88 |
| 5,057,540 | 10/1991 | Kensil et al. | 514/25 |
| 5,080,896 | 1/1992 | Visser et al. | 424/88 |
| 5,118,671 | 6/1992 | Bombardelli et al. | 514/26 |
| 5,273,965 | 12/1993 | Kensil et al. | 514/3 |
| 5,443,829 | 8/1995 | Kensil et al. | 424/195.1 |

FOREIGN PATENT DOCUMENTS

| | | |
|---|---|---|
| 0191536 | 8/1986 | European Pat. Off. |
| 91-01750 | 2/1991 | WIPO |

OTHER PUBLICATIONS

Berezin, V. E. et al., "Controlled Organization of Multimolecular Complexes of Enveloped Virus Glycoproteins: Study of Immunogenicity", *Vaccine* 6:450–456 (1988).

Ertürk, M. et al., "Antibody Responses and Protection In Mice Immunized with Herpes Simplex Virus Type 1 Antigen Immune–Stimulating Complex Preparations", *J. gen. Virol.* 70:2149–2155 (1989).

Howard, C. R. et al., "Preparation and Properties of Immune–Stimulating Complexes Containing Hepatitis B. Virus Surface Antigen", *J. gen. Virol.* 68:2281–2289 (1987).

Kersten, G. F. A. et al., "Incorporation of the Major Outer Membrane Protein of *Neisseria gonorrhoeae* In Saponin–Lipid Complexes (Iscoms): Chemical Analysis . . . ", *Infection and Immunity* 56(2):432–438 (1988).

Maharaj, I. et al., "Immune Response of Mice to Inactivated Rabies Vaccine Administered Orally: Potentiation by Quillaja Saponin", *Can. J. Microbiol.* 32:414–420 (1986).

Winter, A. J. et al., "Effectiveness of Natural and Synthetic Complexes of Porin and O Polysaccharide As Vaccines Against *Brucella abortus* In Mice", *Infection and Immunity* 56(11):2808–2817 (1988).

Bomford, R., *Int. Archs Allergy Appl. Immun.* 75:280–281 (1984).

Bomford, R., *Int. Archs Allergy Appl. Immun.* 63:170–177 (1980).

Bomford, R., *Int. Archs Allergy Appl. Immun.* 67:127–131 (1982).

Dalsgaard, K., *Archiv für die gesamte Virusforschung* 44:243–254 (1974).

Dalsgaard, K., *Acta Veterinaria Scandinavice* (Suppl.) 69:1–40 (1978).

Egerton et al., *Veterinary Science Communications* 2:247–252 (1978).

Higuchi et al., *Phytochemistry* 26:229–235 (1987).

Higuchi et al., *Phytochemistry* 27:1165–1168 (1988).

Higuchi et al., *Phytochemistry* 26:2357–2360 (1987).

Kartnig et al., *Planta Medica* 23:269–271 (1973).

McColm et al., *Parasite Immunology* 4:337–347 (1982).

Morein et al., *Nature* 308:457–460 (1984).

Mostad et al., *Journal of Chromatography* 396:157–168 (1987).

Nagasawa et al., *Chem. Pharm. Bull.* 28:2059–2064 (1980).

Petermann et al., *Chemical Abstracts* 72:198, 88330c (1970).

Sakuma et al., *Journal of Chromatography* 400:293–295 (1987).

Scott et al., *Int. Archs Allergy Appl. Immun.* 77:409–412 (1985.

Strobbe et al., *Arch. Exper. Vet. Med.* 28:385–392 (1974).

Zhou et al., *Chem. Pharm. Bull.* 29:2844–2850 (1981).

Newman, M. J. et al., Grant Application accepted by the Department of Health and Human Services, Public Health Service, Saponin Adjuvant Based HIV–1 Subunit Vaccines, funded Aug. 1, 1992.

White et al., A Purified Saponin Acts As An Adjuvant For A T–Independent Antigen, *Immunology of Proteins and Peptides* VI:207–209 (1991).

Osterhaus, Albert et al., "Induction of Protective Immune Response in Cats by Vaccination with Feline Leukemia Virus Iscom", *J. Immunology* 135: 591–596 (1985).

Primary Examiner—James C. Housel
Assistant Examiner—N. M. Minnifield
Attorney, Agent, or Firm—Sterne, Kessler, Goldstein & Fox

[57] ABSTRACT

Saponin/antigen conjugates and the use thereof for enhancing immune responses in individuals are disclosed. The saponins may be substantially pure or mixtures of saponins.

50 Claims, 39 Drawing Sheets

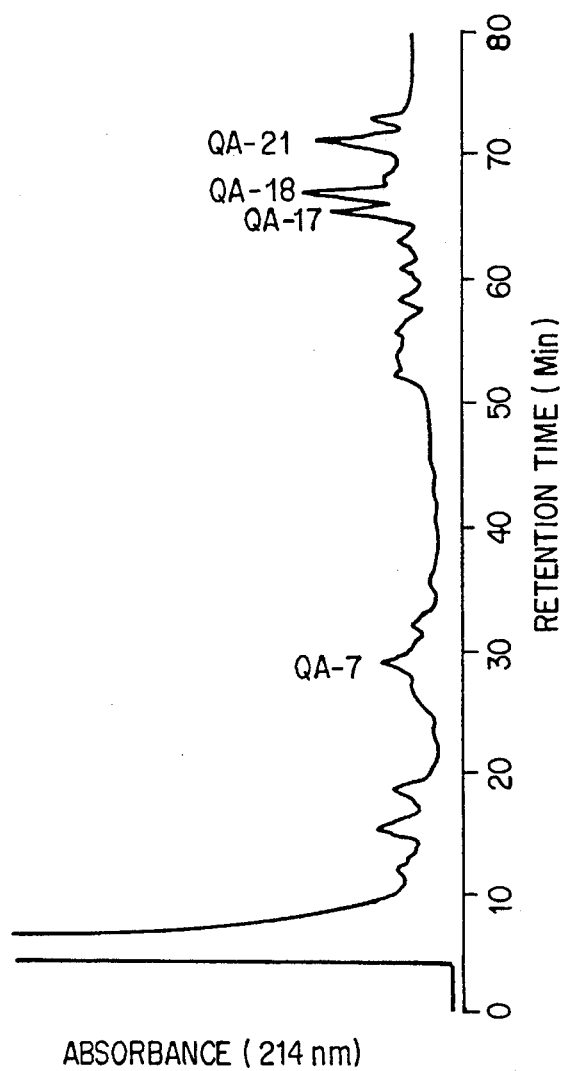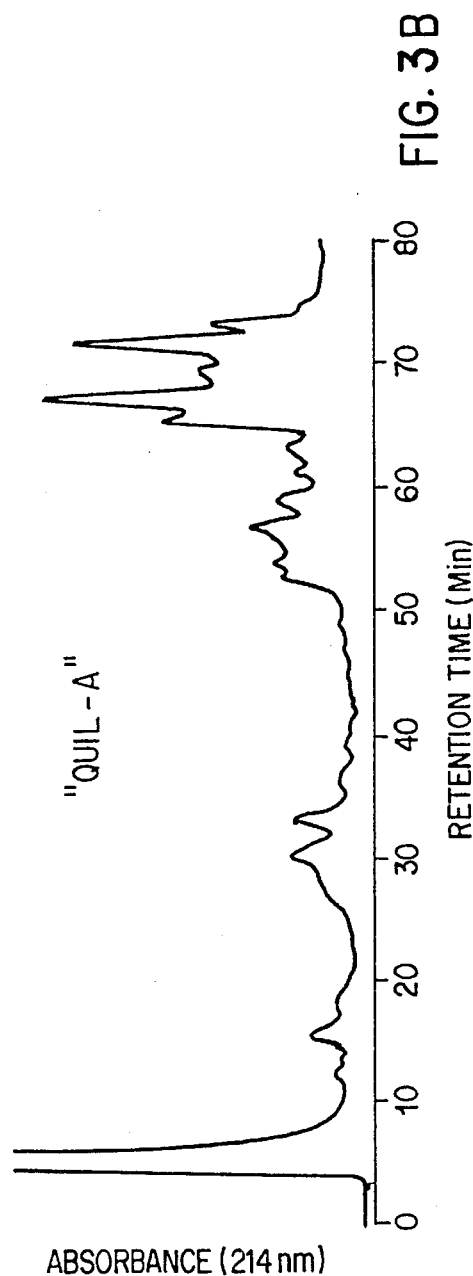

| | $R_1$ | $R_2$ | $R_3$ | M/Z | REVERSE PHASE RETENTION TIME (MIN) | |
|---|---|---|---|---|---|---|
| | | | | | FRAGMENT A | FRAGMENT B |
| QA17 | GLUCOSE | RHAMNOSE | APIOSE | 2321 | 8.0 | 26.7 |
| QA18 | GLUCOSE | H | APIOSE | 2174 | 8.0 | 26.4 |
| QA21-V1 | H | H | APIOSE | 2012 | 9.3 | 25.6 |
| QA21-V2 | H | H | XYLOSE | 2012 | 9.3 | 25.6 |

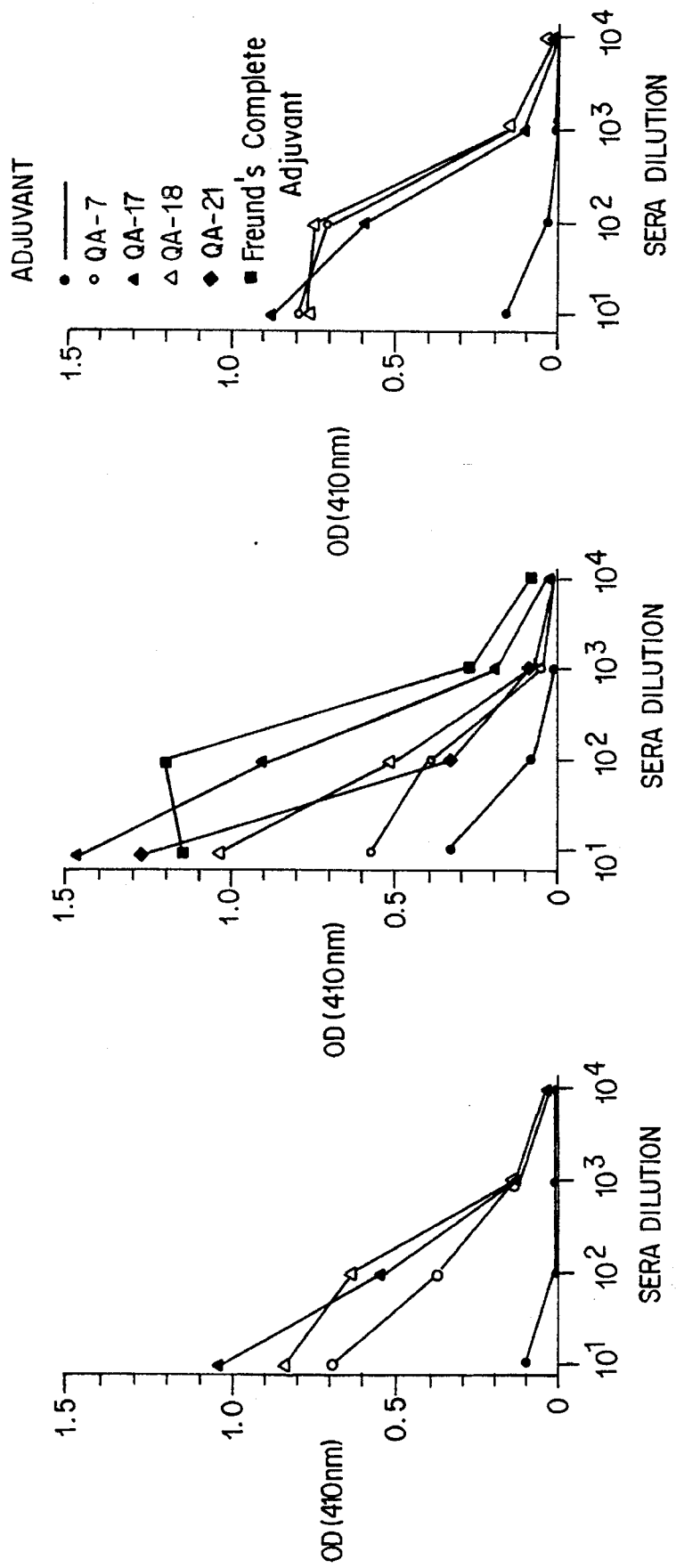

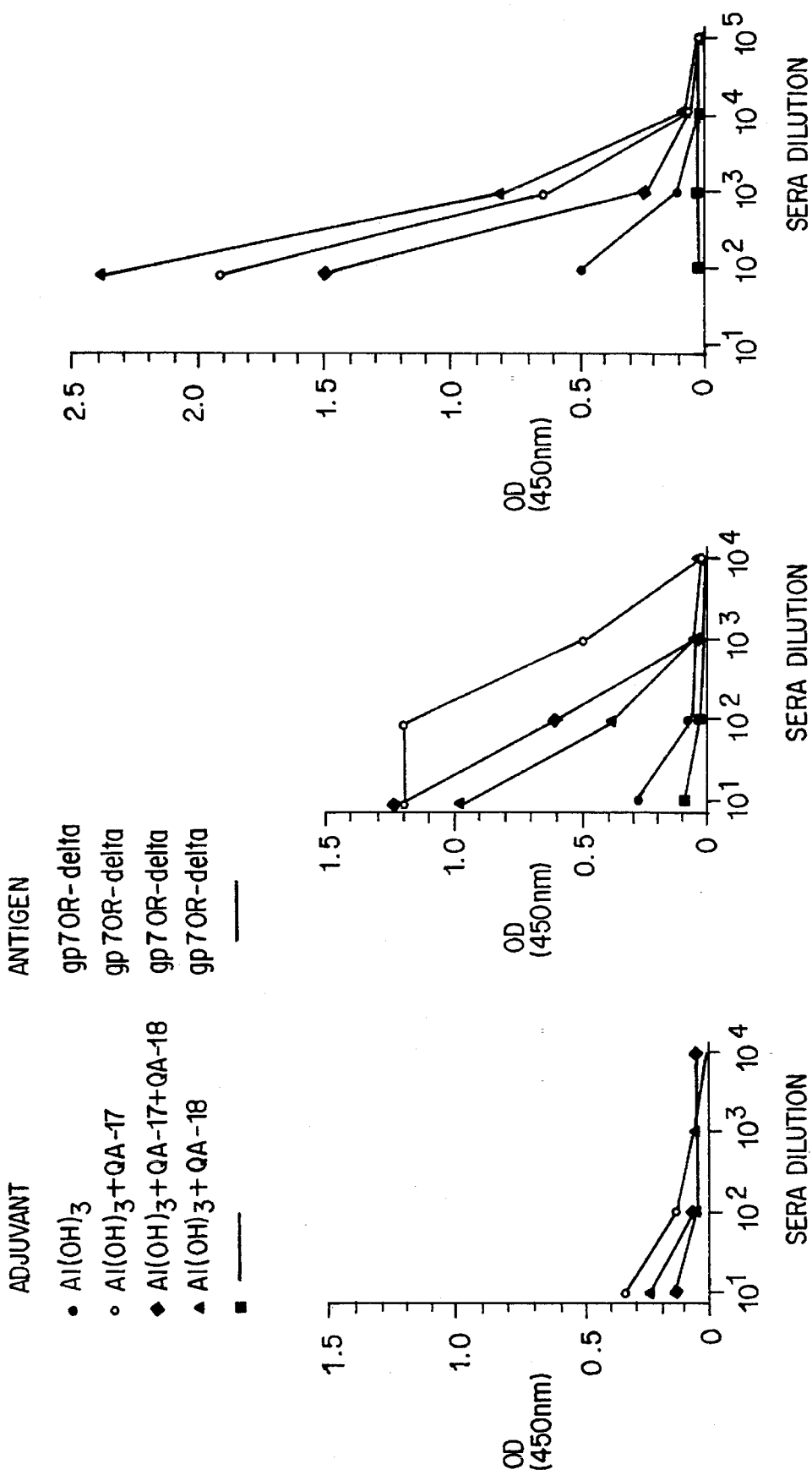

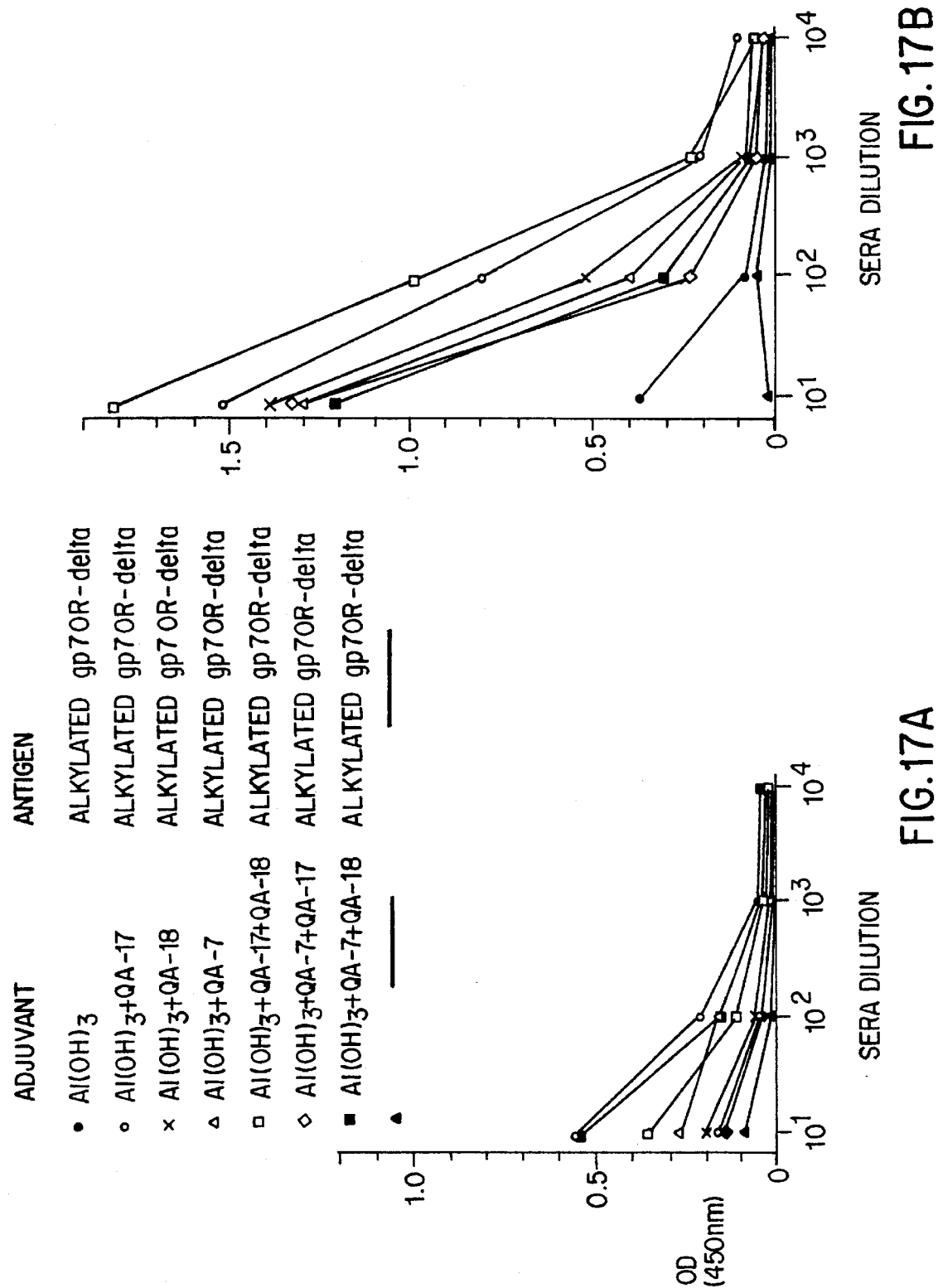

5,583,112

SAPONIN-ANTIGEN CONJUGATES AND THE USE THEREOF

CROSS REFERENCE TO RELATED APPLICATIONS

This application is a continuation-in-part of co-pending U.S. application Ser. No. 07/762,754, filed Sep. 18, 1991, now abandoned, which is a continuation-in-part of U.S. application Ser. No. 07/573,268, filed Aug. 27, 1990, and issued as U.S. Pat. No. 5,057,540 on Oct. 15, 1991, which is a file wrapper continuation of U.S. application Ser. No. 07/200,754, filed May 31, 1988, abandoned, which is a continuation-in-part of U.S. patent application Ser. No. 07/055,229 filed May 29, 1987, abandoned, the disclosures of which are fully incorporated by reference herein.

BACKGROUND OF THE INVENTION

1. Field of the Invention

The present invention is in the field of medicinal chemistry. In particular, the invention is related to vaccines comprising a saponin, the process for production thereof, and the use thereof to immunize animals.

2. Brief Description of the Background Art

Quillaja saponins are a mixture of triterpene glycosides extracted from the bark of the tree *Quillaja saponaria*. Crude saponins have been extensively employed as adjuvants in vaccines against foot and mouth disease, and in amplifying the protective immunity conferred by experimental vaccines against protozoal parasites such as *Trypanosoma cruzi* plasmodium and also the humoral response to sheep red blood cells (SRBC). (Bomford, *Int. Arch. Allerg. Appl. Immum.* 67:127 (1982)).

Saponins are natural products which have been characterized by a number of common properties. The ability to produce foam in aqueous solution gave the name to the group. Further characteristics are the hemolytic activity, the toxicity for fish, the complexing with cholesterol, and in some cases antibiotic activity. Kofler, *Die Saponine* (Springer Berlag), Berlin, 1927; Tschesche et al., *Chemine und Biologic der Saponine, Fortscher. Chem. Org. Naturst.* XXX:461 (1972).

The common properties of saponins are not reflected in a common chemical composition. Although all saponins are glycosides, the aglycone may belong to the steroids, the triterpenoids, or the steroidalkaloids. The number of sugar and sugar chains attached to the glycosidic bonds may vary greatly. Saponins have been produced commercially and have many uses. The commercially available Quillaja saponins are crude mixtures which, because of their variability, are not desirable for use in veterinary practice or in pharmaceutical compositions for man. Because of the variability and heterogeneity, each batch must be tested in animal experiments to determine adjuvant activity and toxicity. The impurities in the commercially available products may produce adverse reactions. In addition, the content of the active substance in a given batch of saponin may vary, thereby decreasing the reproducibility from batch to batch.

An early attempt to purify *Quillaja saponin* adjuvants was made by Dalsgaard, *Archiv fuer die gesamte Virusforschung* 44:243 (1974). Dalsgaard partially purified an aqueous extract of the saponin adjuvant material from *Quillaja saponaria* Molina. Dalsgaard's preparation, commercially available from Superfos under the name "Quil-A," has been isolated from the bark of the South American tree, *Quillaja saponaria* Molina, and is characterized chemically as a carbohydrate moiety in glycosidic linkage to the triterpenoid quillaic acid. However, while the saponin Quil A of Dalsgaard presents a definite improvement over the previously available commercial saponins, it also shows considerable heterogeneity.

Higuchi et al., *Phytochemistry* 26:229 (January, 1987) treated a crude Quillaja saponin mixture with alkaline hydrolysis in 6% $NH_4HCO_3$ in 50% methanol and generated two major desacylsaponins, termed DS-1 and DS-2. DS-1 was shown to contain glucuronic acid, galactose, xylose, fucose, rhamnose, apiose, and Quillajic acid, whereas DS-2 contained these same components plus an additional glucose. Byproducts of this deacylation produced multiple components including 3,5-dihydroxy-6-methyloctanoic acid, 3,5-dihydroxy-6-methyloctanic acid-5-0-α-L-arabinofuranoside and -5-O-α-L-rhamnopyranosyl-(1→2)-α-L-arabinofuranoside (Higuchi et al., *Phytochemistry* 26:2357 (August, 1987).

BRIEF DESCRIPTION OF THE FIGURES

FIGS. 3A–3B show the comparison of Superfos "Quil-A" and dialyzed methanol soluble bark extract by HPLC.

FIGS. 14A–14C demonstrate the comparison of the adjuvant effects of QA-7, QA-17, QA-18 and QA-21 at various antigen concentrations and with Freund's complete adjuvant on immunization with the antigen BSA FIG. 14A: antigen= 15 μg BSA; FIG. 14B: antigen=30 μg BSA; FIG. 14C: antigen=45 μg BSA.

FIGS. 16A–16C show the adjuvant effects of HPLC-purified adjuvants used in conjunction with $Al(OH)_3$, another adjuvant, on the immunization with the antigen gp70R-delta FIG. 16A—two weeks post-immunization, FIG. 16B—four weeks post-immunization, FIG. 16C—eight weeks post-immunization (boost at six weeks).

FIGS. 17A–17B smnmarize the effects of HPLC-purified Quillaja saponins alone and in combination with each other and with another adjuvant on the immunization with the antigen alkylated gp70R-delta FIG. 17A—two weeks post-immunization, FIG. 17B—four weeks post-immunization.

SUMMARY OF THE INVENTION

Figure 1:
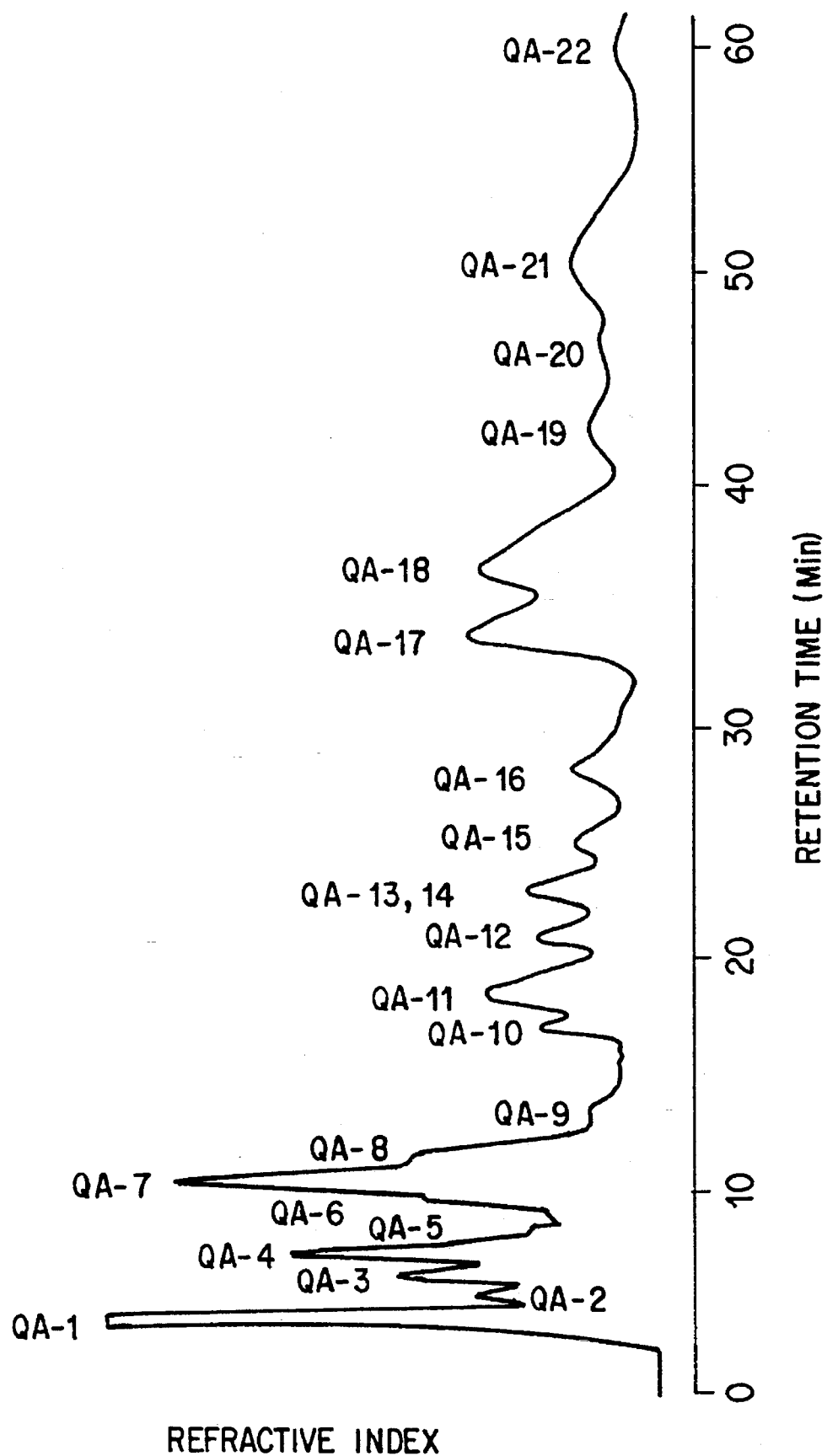
FIG. 1 shows the refractive index profile of dialyzed, methanol-solubilized Quillaja bark extract on reverse phase-HPLC.

Adjuvant saponins have been identified and purified from an aqueous extract of the bark of the South American tree, *Quillaja saponaria* Molina. At least 22 peaks with saponin activity were separable. The predominant purified Quillaja saponins have been identified as QA-7, QA-17, QA-18, and QA-21 (Also known as QS-7, QS-17, QS-18 and QS-21, respectively). These saponins have been purified by high pressure liquid chromatography (HPLC) and low pressure silica chromatography. These four saponins have adjuvant effect in mice. Unexpectedly, QA-21 was further purified using hydrophilic interaction chromatography (HILIC) and resolved into two peaks, QA-21-V1 and QA-21-V2, which have been shown to be different compounds. The substantially pure saponins of the present invention are useful as immune adjuvants and enhance immune responses in individuals at a much lower concentration than the previously available heterogeneous saponin preparations without the toxic effects associated with crude saponin preparations.

The present invention is directed to saponin/antigen conjugates which comprise a saponin linked to an antigen, wherein the linkage does not interfere substantially with the ability of the saponin to stimulate an immune response in an animal.

The invention is also directed to modified saponins which comprise a saponin modified with a linking molecule, wherein the modification does not interfere substantially with the ability of the saponin to stimulate an immune response in an animal.

The invention is also directed to saponin hydrolytic product/antigen conjugates which comprise a saponin hydrolytic product linked to an antigen, wherein the linkage does not interfere substantially with the ability of the saponin hydrolytic product to stimulate an immune response in an animal.

The invention also relates to a vaccine which comprises a saponin/antigen conjugate of the invention, a pharmaceutically acceptable carrier, and, optionally, one or more adjuvants. Preferably, the adjuvant is a saponin of the present invention.

The invention also relates to a vaccine which comprises a saponin hydrolytic product/antigen conjugate of the invention and a pharmaceutically acceptable carrier.

DESCRIPTION OF THE PREFERRED EMBODIMENTS

The saponins of the present invention may be obtained from the tree *Quillaja saponaria* Molina.

The term "saponin" as used herein includes glycosidic triterpenoid compounds which produce foam in aqueous solution, have hemolytic activity in most cases, and possess immune adjuvant activity. The invention encompasses the saponin per se, as well as natural and pharmaceutically acceptable salts and pharmaceutically acceptable derivatives. The term "saponin" also encompasses biologically active fragments thereof.

The invention also concerns compositions, such as immunologic compositions, comprising one or more substantially pure saponin fractions or hydrolytic products thereof which may be linked to an antigen, and methods of using these compositions as vaccines and immune adjuvants.

The term "immune adjuvant," as used herein, refers to compounds which, when administered to an individual or tested in vitro, increase the immune response to an antigen in the individual or test system to which said antigen is administered. Some antigens are weakly immunogenic when administered alone or are toxic to the individual at concentrations which evoke immune responses in said individual. An immune adjuvant may enhance the immune response of the individual to the antigen by making the antigen more strongly immunogenic. The adjuvant effect may also lower the dose of said antigen necessary to achieve an immune response in said individual.

It has now been discovered that saponins, when linked to an antigen, markedly enhances the immune response to the antigen, even when the antigen is weakly iinmunogenic. In addition, the saponin conjugates of the present invention stimulate the production of multiple subtypes of antibodies. Unexpectedly, when the saponin/antigen conjugates of the present invention are coadministered with a saponin adjuvant (not linked to the antigen), the immune response is enhanced to a much greater extent. Thus, the present invention is a great advance in the art in that it allows for the induction of active immunity to certain antigens which heretofore was not possible.

The immunogen activity of the saponin conjugates and saponin adjuvants of the present invention may be determined by any of a number of methods known to those of ordinary skill in the art. The increase in titer of antibody against a particular antigen upon administration of the vaccines and/or adjuvants of the invention may be used as a criteria for immunogenic activity (Dalsgaard, K. (1978) *Acta Veterinia Scandinavica* 69:1–40, Scott et al. *Int. Archs. Allergy Appl. Immun.* 77:409–412 (1985)). Briefly, one such test involves injecting CD-1 mice intradermally with a saponin/antigen conjugate which may be mixed with varying amounts of a potential adjuvant. Sera was harvested from the mice two weeks later and tested by ELISA for anti-immunogen antibody.

A comparison of the adjuvant effects of the dialyzed, methanolsoluble bark extract and "Quil A" showed that antibody titers were two orders of magnitude greater when the antigen BSA was administered in the presence of the saponin preparations than when BSA was administered in PBS alone. The bark extract possessed good adjuvant activity when administered at an adjuvant dose of 12 µg carbohydrate (assayed by anthrone) or more. The adjuvant response to "Quil-A" was lower than for the bark extract but was evident at doses ranging from 9–23 µg carbohydrate. Carbohydrate weight (determined by assay with anthrone using glucose as a standard) is approximately 30% of the dry weight of these crude adjuvant extracts.

The term "substantially pure" means substantially free from compounds normally associated with the saponin in its natural state and exhibiting constant and reproducible chromatographic response, elution profiles, and biologic activity. The term "substantially pure" is not meant to exclude artificial or synthetic mixtures of the saponin with other compounds.

Preferably, the substantially pure saponin is purified to one or more of the following standards: 1) appearing as only one major carbohydrate staining band on silica gel TLC (EM Science HPTLC Si60) in a solvent system of 40 mm acetic acid in chloroform/methanol/water (60/45/10, v/v/v), 2) appearing as only one major carbohydrate staining band on reverse phase TLC (EM Science Silica Gel RP-8) in a solvent system of methanol/water (70/30, v/v), 3) appearing as only one major peak upon reverse-phase HPLC on Vydac C4 (5 µm particle size, 330 Å pore, 4.6 mm ID×25 cm L) in 40 mM acetic acid in methanol/water (58/42, v/v).

"QA-21" designates the mixture of components QA-21-V1 and QA-21-V2 which appear as a single peak on reverse phase HPLC on Vydac C4 (5 µm particle size, 330 Å pore, 4.6 mm ID×25 cml) in 40 mM acetic acid in methanol/water (58/42, v/v). The component fractions are referred to specifically as QA-21-V1 and QA-21-V2 when describing experiments or results performed on the further purified components.

Figure 2A:
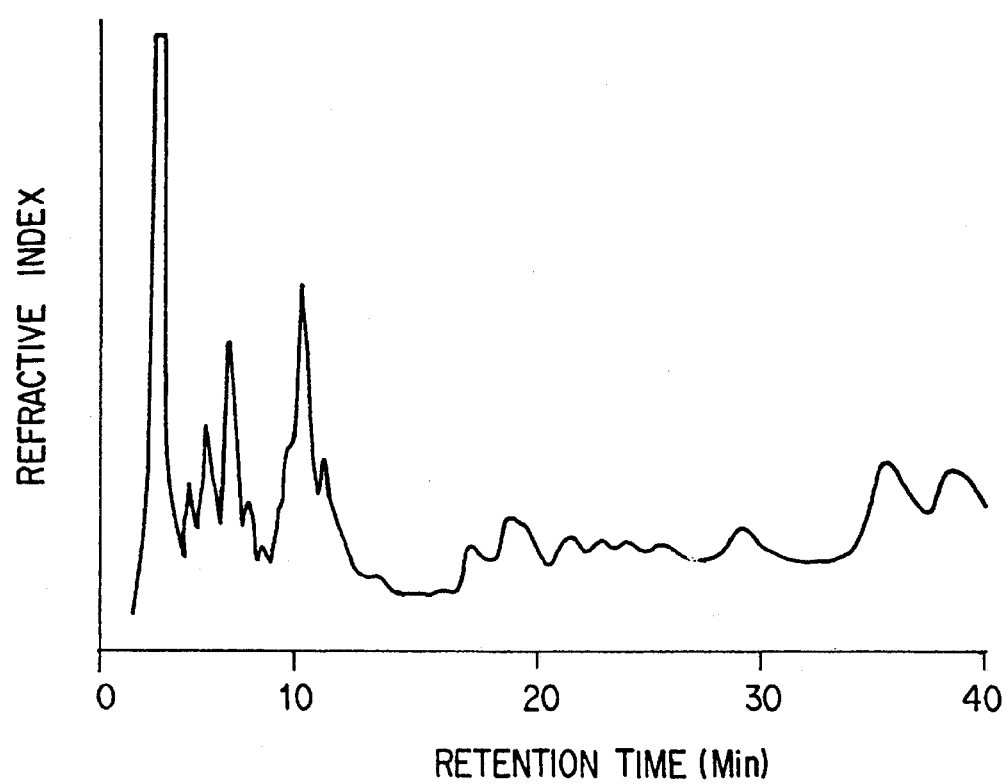
FIGS. 2A–2B show that the refractive index peaks of the above sample correspond to carbohydrate peaks.
Figure 2B:
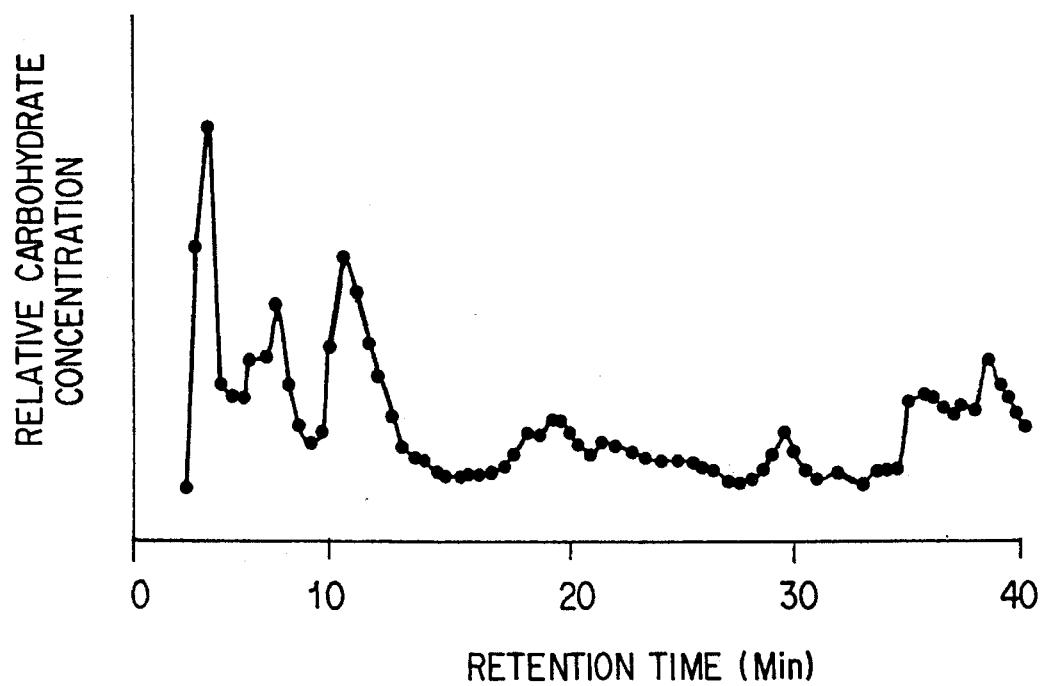

In the preferred embodiment, the saponins of the present invention are purified from *Quillaja saponaria* Molina bark. Aqueous extracts of the *Quillaja saponaria* Molina bark were dialyzed against water. The dialyzed extract was lyophilized to dryness, extracted with methanol and the methanol-soluble extract was further fractionated on silica gel chromatography and by reverse phase high pressure liquid chromatography (RP-HPLC). The individual saponins were separated by reverse phase HPLC as described in Example 1. At least 22 peaks (denominated QA-1 to QA-22) were separable. Each peak corresponded to a carbohydrate peak as demonstrated in FIG. 2 and exhibited only a single band on reverse phase thin layer chromatography. The individual components were identified by retention time on a Vydac $C_4$ HPLC column as follows:

| Peak | Retention Time (minutes) |
|------|--------------------------|
| QA-1 | solvent front |
| QA-2 | 4.6 |
| QA-3 | 5.6 |
| QA-4 | 6.4 |
| QA-5 | 7.2 |
| QA-6 | 9.2 |
| QA-7 | 9.6 |
| QA-8 | 10.6 |
| QA-9 | 13.0 |
| QA-10 | 17.2 |
| QA-11 | 19.0 |
| QA-12 | 21.2 |
| QA-13 | 22.6 |
| QA-14 | 24.0 |
| QA-15 | 25.6 |
| QA-16 | 28.6 |
| QA-17 | 35.2 |
| QA-18 | 38.2 |
| QA-19 | 43.6 |
| QA-20 | 47.6 |
| QA-21 | 51.6 |
| QA-22 | 61.0 |

Immune adjuvant activity was tested by measuring the ability of the purified saponins to enhance the immune response in mice to exogenously administered antigens. The purified saponins of the present invention demonstrated adjuvant effects at lower doses than the crude extracts. Particularly, the predominant saponins in bark extract (QA-7, QA-17, QA-18, and QA-21) demonstrated adjuvant activity at doses of 4.5 µg carbohydrate or less (assayed by anthrone). The purified saponins were further characterized by carbohydrate content, reverse phase and normal phase TLC, UV, infra red, NMR spectra, and fast atom bombardment—mass spectroscopy.

The approximate extinction coefficient determined for 1% (w/v) solutions in methanol at 205 nm of several of the more preferred purified saponins are as follows:

| | 1% $E_{205nm}$ |
|---|---|
| QA-7 | 34 |
| QA-17 | 27 |
| QA-18 | 27 |
| QA-21 | 28 |

Carbohydrate content was used to quantitate the saponins in some instances. The carbohydrate assay was the anthrone method of Scott and Melvin (*Anal. Chem.* 25:1656 (1953)) using glucose as a standard as described in Example 1. This assay was used to determine a ratio of extent of anthrone reaction (expressed in glucose equivalents) per mg of purified saponin (dry weight) so that dry weight of a particular preparation could be estimated by use of anthrone assay. It must be noted that differences in reactivity with anthrone for different saponins may be due to carbohydrate composition rather than quantity as different monosaccharides react variably in this assay.

The substantially pure QA-7 saponin is characterized as having immune adjuvant activity, containing about 35% carbohydrate (as assayed by anthrone) per dry weight, having a uv absorption maxima of 205–210 nm, a retention time of approximately 9–10 minutes on RP-HPLC on a Vydac $C_4$ column having 5 μm particle size, 330 Å pore, 4.6 mm ID×25 cm L in a solvent of 40 mM acetic acid in methanol/water (58/42; v/v) at a flow rate of 1 ml/min, eluting with 52–53% methanol from a Vydac $C_4$ column having 5 μm particle size, 330 Å pore, 10 mM ID×25 cm L in a solvent of 40 mM acetic acid with gradient elution from 50 to 80% methanol, having a critical micellar concentration of approximately 0.06% in water and 0.07% in phosphate buffered saline, causing no detectable hemolysis of sheep red blood cells at concentrations of 200 μg/ml or less, and containing the monosaccharide residues terminal rhamnose, terminal xylose, terminal glucose, terminal galactose, 3-xylose, 3,4-rhamnose, 2,3-fucose, and 2,3-glucuronic acid, and apiose (linkage not determined).

The substantially pure QA-17 saponin is characterized as having adjuvant activity, containing about 29% carbohydrate (as assayed by anthrone) per dry weight, having a UV absorption maxima of 205–210 nm, a retention time of approximately 35 minutes on RP-HPLC on a Vydac $C_4$ column having 5 μm particle size, 330 Å pore, 4.6 mm ID×25 cm L in a solvent of 40 mM acetic acid in methanol-water (58/42; v/v) at a flow rate of 1 ml/min, eluting with 63–64% methanol from a Vydac $C_4$ column having 5 μm particle size, 330 Å pore, 10 mm ID×25 cm L in a solvent of 40 mM acetic acid with gradient elution from 50 to 80% methanol, having a critical micellar concentration of 0.06% (w/v) in water and 0.03% (w/v) in phosphate buffered saline, causing hemolysis of sheep red blood cells at 25 μg ml or greater, and containing the monosaccharide residues terminal rhamnose, terminal xylose, 2-fucose, 3-xylose, 3,4-rhamnose, 2,3-glucuronic acid, terminal glucose, 2-arabinose, terminal galactose and apiose (linkage not determined).

The substantially pure QA-18 saponin is characterized as having immune adjuvant activity, containing about 25–26% carbohydrate (as assayed by anthrone) per dry weight, having a UV absorption maxima of 205–210 nm, a retention time of approximately 38 minutes on RP-HPLC on a Vydac $C_4$ column having 5 μm particle size, 330 Å pore, 4.6 mm ID ×25 cm L in a solvent of 40 mM acetic acid in methanol/water (58/42; v/v) at a flow rate of 1 ml/min, eluting with 64–65% methanol from a Vydac $C_4$ column having 5 μm particle size, 330 Å pore, 10 mm ID×25 cm L in a solvent of 40 mM acetic acid with gradient elution from 50 to 80% methanol, having a critical micellar concentration of 0.04% (w/v) in water and 0.02% (w/v) in phosphate buffered saline, causing hemolysis of sheep red blood cells at concentrations of 25 μg/ml or greater, and containing the monosaccharides terminal arabinose, terminal apiose, terminal xylose, terminal glucose, terminal galactose, 2-fucose, 3-xylose, 3,4-rhamnose, and 2,3-glucuronic acid.

The substantially pure QA-21 saponin is characterized as having immune adjuvant activity, containing about 22% carbohydrate (as assayed by anthrone) per dry weight, having a UV absorption maxima of 205–210 nm, a retention time of approximately 51 minutes on RP-HPLC on a Vydac $C_4$ column having 5 μm particle size, 330 Å pore, 4.6 mm ID×25 - 13 cm L in a solvent of 40 mM acetic acid in methanol/water (58/42; v/v) at a flow rate of 1 ml/min, eluting with 69 to 70% methanol from a Vydac $C_4$ column having 5 μm particle size, 330 Å pore, 10 mm×ID 25 cm L in a solvent of 40 mM acetic acid with gradient elution from 50 to 80% methanol, with a critical micellar concentration of about 0.03% (w/v) in water and 0.02% (w/v) in phosphate buffered saline, and causing hemolysis of sheep red blood cells at concentrations of 25 μg/ml or greater. The component fractions, substantially pure QA-21-V1 and QA-21-V2 saponins, have the same molecular weight and identical spectrums by FAB-MS. They differ only in that QA-21-V1 has a terminal apiose which is xylose in QA-21-V2 (which therefore has two terminal xyloses and no apiose). The two components additionally contain the monosaccharides terminal arabinose, terminal apiose, terminal xylose, 4-rhamnose, terminal galactose, 2-fucose, 3-xylose, and 2,3-glucuronic acid. The structures of the saponins are disclosed more fully in the Examples, below.

The conjugates of the invention are useful as vaccines which induce active immunity toward antigens in individuals. Preferably, such individuals are humans, however the invention is not intended to be so limiting. Any animal which may experience the beneficial effects of the vaccines of the invention are within the scope of animals which may be treated according to the claimed invention. The purified saponins exhibit adjuvant effects when administered over a wide range of dosages and a wide range of ratios to the antigen being administered. In one embodiment, the saponin is administered in a ratio of adjuvant to immunogen (w/w) of 3.0 or less, preferably 1.0 or less.

The purified saponins and saponin-antigen conjugates may be administered either individually or admixed with other substantially pure adjuvants to achieve the enhancement of the immune response to an antigen. Moreover, the saponin/antigen conjugates of the present invention may comprise a single saponin or mixtures of saponins linked to the antigen. The mixtures of the saponins linked to the antigen may be purified saponins or crude mixtures of saponins. While crude saponin mixtures are toxic and not normally administered to animals, the formation of saponin-antigen conjugates may serve to reduce the toxicity of the composition, such that the conjugates may be administered to an animal without causing any untoward effects.

Among the saponin mixtures effective in the present invention are fractions QA-7 and QA-17, QA-7 and QA-18, QA-17 and QA-18, or QA-7, QA-17, and QA-18 administered together. Purified saponins and conjugates thereof may also be administered together with non-saponin adjuvants. Such non-saponin adjuvants useful with the present invention are oil adjuvants (for example, Freund's Complete and Incomplete), liposomes, mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (for example, wax D from *Mycobacterium tuberculosis*, as well as substances found in *Corynebacterium parvum, Bordetella pertussis*, and members of the genus Brucella), bovine serum albumin, diphtheria toxoid, tetanus toxoid, edestin, keyhole-limpet hemocyanin, Pseudomonal Toxin A, choleragenoid, cholera toxin, pertussis toxin, viral proteins, and eukaryotic proteins such as interferons, interleukins, or tumor necrosis factor. Such proteins may be obtained frown natural or recombinant sources according to methods known to those skilled in the art. When obtained from recombinant sources, the non-saponin adjuvant may comprise a protein fragment comprising at least the immunogenic portion of the molecule. Other known immunogenic macromolecules which may be used in the practice of the invention include, but are not limited to, polysaccharides, tRNA, nomnetabolizable synthetic polymers such as polyvinylamine, polymethacrylic acid polyvinylpyrrolidone, mixed polycondensates (with relatively high molecular weight) of 4'4'-diaminodiphenyl-methane-3,3'-dicarboxylic acid and 4-nitro-2-aminobenzoic acid (See Sela, M., *Science* 166:1365–1374 (1969)) or glycolipids, lipids or carbohydrates.

The saponins of the present invention may be directly linked to the antigen or may be linked via a linking group. By the term "linker group" is intended one or more bifunctional molecules which can be used to covalently couple the saponin or saponin mixture to the antigen and which do not interfere with the production of antigen-specific antibodies in vivo. The linker group may be attached to any part of the saponin so long as the point of attachment does not interfere with the production of antigenspecific antibodies in vivo and thus interfere with the induction of active immunity.

Examples of linker groups which can be used to link the saponin to the antigen may comprise $$-NH-(CH_2)_q-NH-,$$
wherein q is 2–10;

$$-O-(CH_2)_r-NH-,$$
wherein r is 2–10;

$$-X-(CH_2)_s-X-\overset{O}{\underset{\|}{C}}-(CH_2)_t\overset{O}{\underset{\|}{C}}-,$$
wherein X = NH, S or O, s = 2–5, t = 2–12;

$$-\overset{O}{\underset{\|}{C}}-(CH_2)_u\overset{O}{\underset{\|}{C}}-,$$
wherein u = 2–12;

$$-Y-(CH_2)_v-\overset{O}{\underset{\|}{C}}-,$$
wherein Y is NH or S, v = 1–3.

Typically, the saponins are linked to the antigen by the preparation of an active ester of glucuronic acid, a component of the saponins, followed by reaction of the active ester with a nucleophilic functional group on the antigen. Examples of the active esters which may be used in the practice of the invention include the glucuronate of N-hydroxysuccinimide, sulfo-N-hydroxysuccinimide, hydroxybenzotriazole, and p-nitrophenol. The active esters may be prepared by reaction of the carboxy group of the saponin with an alcohol in the presence of a dehydration agent such as dicyclohexylcarbodiimide (DCC), 1-(3-dimethylaminopropyl)-3-ethylcarbodiimide (EDC), and 1-(3-dimethylaminopropyl)-3-ethylcarbodiimide methiodide (EDCI). The use of EDC to form conjugates is disclosed in U.S. Pat. No. 4,526,714 to Feijen et al. and PCT application publication no. WO91/01750, and Arnon, R et al., *Pros. Natl. Acad. Sci. (USA)* 77:6769–6772 (1980), the disclosures of which are fully incorporated by reference herein. The antigen is then mixed with the activated ester in aqueous solution to give the conjugate.

Where a linker group between the saponin and the antigen is desired, the active ester of the saponin glucuronate is prepared as described above and reacted with the linker group, e.g. 2-aminoethanol, an alkylene diamine, an amino acid such as glycine, or a carboxy-protected amino acid such as glycine tert-butyl ester. If the linker contains a protected carboxy group, the protecting group is removed and the active ester of the linker is prepared (as described above). The active ester is then reacted with the antigen to give the conjugate. Alternatively, the antigen may be derivatized with succinic anhydride to give an antigensuccinate conjugate which may be condensed in the presence of EDC or EDCI with a saponin-linker derivative having a free amino or hydroxyl group on the linker. See WO91/01750.

Once derivatized at the glucuronate carboxyl with a linker group, the saponins retain adjuvant activity. Those saponin derivatives prepared by reductive alkylation at the triterpene aldehyde do not appear to retain adjuvant activity at doses less than 40 μg. However, derivatives in which the saponin triterpene aldehyde was reduced to an alcohol by sodium borohydride reduction did retain some activity.

It is also possible to prepare a saponin conjugate comprising a linker with a free amino group (derived from an alkylene diamine) and crosslink the free amino group with a heterobifunctional cross linker such as sulfosuccinimidyl 4-(N-maleimidocyclohexane)-1-carboxylate which will react with the free sulfhydryl groups of protein antigens.

The saponin may also be coupled to a linker group by reaction of the aldehyde group of the quillaic acid residue with an amino linker to form an intermediate imine conjugate, followed by reduction with sodium borohydride or sodium cyanoborohydride. Examples of such linkers include amino alcohols such as 2-aminoethanol and diamino compounds such as ethylenediamine, 1,2-propylenediamine, 1,5-pentanediamine, 1,6-hexanediamine, and the like. The antigen may then be coupled to the linker by first forming the succinated derivative with succinic anhydride followed by condensation with the saponin-linker conjugate with DCC, EDC or EDCI.

In addition, the saponin may be oxidized with periodate and the dialdehyde produced therefrom condensed with an amino alcohol or diamino compound listed above. The free hydroxyl or amino group on the linker may then be condensed with the succinate derivative of the antigen in the presence of DCC, EDC or EDCI.

The ratio of saponin molecules per antigen molecule may vary considerably according to the molecular weight of the antigen, the number of binding sites on the antigen capable of being coupled to the saponin, and the antigenic characteristics of the particular saponin. In general, the ratio of saponin molecules to antigen molecule may be about 0.1:1 to about 10:1. Preferably, the ratio may range from about 1:1 to about 3:1.

The saponins of the present invention may be utilized to enhance the immune response to any antigen. Typical antigens suitable for the immune-response provoking compositions of the present invention include antigens derived from any of the following: viruses, such as influenza, feline leukemia virus, feline immunodeficiency virus, HIV-1, HIV-2, rabies, measles, hepatitis B, or hoof and mouth disease; bacteria, such as anthrax, diphtheria, Lyme disease, or tuberculosis; or protozoans, such as *Babeosis bovis* or Plasmodium. The antigens may be proteins, peptides or polysaccharides. The proteins and peptides may be purified from a natural source, synthesized by means of solid phase synthesis, or may be obtained means of recombinant genetics.

A particular example is the use of the purified saponins of the present invention to enhance the immune response to gp70 recombinant protein. One gp70 recombinant protein is an antigen which contains the polypeptide portion of FeLV gp70 envelope protein. This recombinant antigen is termed "gp70R," "rec-gp70" or "Rgp70." Another antigen preparation which contains the polypeptide portion of FeLV gp70 together with the 40 amino-terminal amino acids (termed "Rgp70-delta") or with the entire amino acid sequence (termed "Rgp90") of the p15e envelope protein of FeLV subgroup A is produced using recombinant DNA techniques. These recombinant gp70-containing polypeptides, gp70R, gp70R-delta, and gp90R, are hereinafter referred to collectively as gp70-containing protein. The term gp70-containing protein is intended to include polypeptides having the same amino acid sequence of the naturally occurring gp70-containing protein, and analogs thereof. The term "analogs" is intended to include proteins or polypeptides which differ from gp70, gp70-delta, or gp90 by addition, deletion or substitution of one or more amino acids providing that said polypeptide demonstrate substantially the biological activity of gp70 protein.

Administration of the compounds useful in the method of present invention may be by parenteral, intravenous, intramuscular, subcutaneous, intranasal, or any other suitable means. The dosage administered may be dependent upon the age, weight, kind of concurrent treatment, if any, and nature of the antigen administered. In general, the saponin/antigen conjugates may be administered at a dosage of about 0.01 to about 1.0 mg/kg of conjugate per weight of tile individual. The initial dose may be followed up with a booster dosage after a period of about four weeks to enhance the immunogenic response. Further booster dosages may also be administered.

The effective compound useful in the method of the present invention may be employed in such forms as capsules, liquid solutions, suspensions or elixirs for oral administration, or sterile liquid forms such as solutions or suspensions. Any inert carrier is preferably used, such as saline, or phosphate-buffered saline, or any such carrier in which the compounds used in the method of the present invention have suitable solubility properties for use in the methods of the present invention.

The saponin/antigen conjugates of the present invention may also be encapsulated within liposomes according to U.S. Pat. No. 4,235,877 to Fullerton.

The invention also provides for a kit for the immunization of an individual comprising a carrier compartmentalized to receive in close confinement therein one or more container means wherein a first container contains a saponin/antigen conjugate of the invention. The kit may also include at least one other container means which contain a saponin adjuvant or other adjuvant as described herein.

Having now generally described the invention, the same may be further understood by reference to the following examples, which are not intended to be limiting unless so expressly stated.

EXAMPLE 1

PRELIMINARY PREPARATION OF *QUILLAJA SAPONARIA* MOLINA BARK EXTRACT

*Quillaja saponaria* Molina bark was stirred with an excess of water (10% w/v) to extract the saponins. The aqueous extract was then filtered and stored in 0.1% $NaN_3$. 150 ml of this extract was centrifuged at 20,000× g for 30 minutes to remove residual bark fragments. The supernatant, which was light brown, was lyophilized and redissolved in 16 ml of water and the pH was adjusted to less than 4 with the addition of 160 µl of 1N acetic acid. This solution was placed in dialysis tubing having a 12,000 MW cut off and dialyzed against 1 liter of water. The water was changed after 8 hours of dialysis, and the dialysis was allowed to proceed overnight. Samples of the dialysate were removed after the first and second dialysis cycles. The dialyzed extract was lyophilized and extracted with 40 ml methanol at 60° C. for 15 minutes followed by centrifugation at 1,000× g for 10 minutes to sediment the undissolved material. This material was subjected to two additional extractions with methanol. The methanol extracts were pooled, evaporated on a rotoevaporator to dryness, redissolved in 5.5 ml methanol, and filtered through a 0.2 µ nylon 66 mesh to remove residual undissolved material. Fractions were analyzed by reverse phase thin-layer chromatography (RP-TLC) on C8 plates (E.M. Science RP-TLC, C8) in a solvent system of 70% methanol/30% water or by normal phase thin layer chromatography on silica gel 60 TLC plates in a solvent system of n-butanol, ethanol, water, and ammonia (30/60/29/21, v/v/v/v). The carbohydrate bands were visualized with Bial's reagent which detected all major bands detectable by sulfuric acid charring with an increased sensitivity over the sulfuric acid charring method. The Bial's reagent carbohydrate stain was routinely used as a detection reagent on TLC plates. All major bands were glycosylated.

Dialysis removed a major carbohydrate-containing band ($R_F$=0.82 on EM Science RP TLC, C8 in methanol/water (70/30, v/v)), as well as some minor components. In addition, dialysis removed components with strong absorption maxima at 280 and 310 nm. Approximately 80% of the carbohydrate (assayed by anthrone) was removed by dialysis, but about 95% of the hemolytic activity was retained during dialysis.

Most saponin adjuvants are known to have detergent properties, such as hemolysis of red blood cells, so the retention of hemolytic activity is a rough indication of the retention of adjuvant saponins. Several bands were retained by dialysis, indicating their detergent nature. Methanol solubilized all TLC bands present in the dialyzed extract except one TLC band ($R_F$=0 on both reverse-phase and silica TLC plates). The methanol-insoluble material was reddish-brown. The material which was methanol-soluble appeared white after lyophilization.

Carbohydrate concentration was determined by the method of Scott and Melvin (Scott et al. *Anal. Chem.* 25:1656 (1953)). Briefly, an aqueous sample to be tested or glucose as a standard carbohydrate solution (450 µl) was mixed with 900 µl of 0.2% anthrone (w/v) in sulfuric acid and incubated for 16 min at 90–100 C. The absorbance was read at 625 nm. Glucose was used as a standard.

The hemolytic activity of the samples was determined as follows: Briefly, samples were diluted in a round bottom microtiter plate with 1:2 dilutions in phosphate buffered saline in successive rows (100 µl/well). 10 µl normal rabbit blood in Alsevers solution (Hazelton) was added to each well and mixed. Plates were incubated for one hour at room temperature followed by centrifugation of the plates in a Sorvall RT6000 to sediment unhemolyzed cells. Absence of hemolysis was determined by the presence of a pellet of unhemolyzed cells in the bottom of the well.

EXAMPLE 2

COMPARISON OF DIALYZED, METHANOL-SOLUBLE BARK EXTRACT AND SUPERFOS "QUIL-A" BY TLC AND HPLC

Superfos "Quil-A" and dialyzed, methanol-soluble components of bark extract prepared as in Example 1 were compared by reverse phase TLC as described in Example 1. All bands present in the bark extract after dialysis and solubilization with methanol were present in "Quil-A." In addition, "Quil-A" contained a band with $r_f$=0 on reverse-phase TLC plates; this component was removed by methanol-solubilization as described above. The similarity in composition of dialyzed, methanolsoluble bark extract and "Quil-A" was continued by HPLC. The individual components of bark extract were separable by reverse-phase HPLC on Vydac C4 (5 µm particle size, 330 Å pore, 4.6 mm ID×25 cm L) in 40 mM acetic acid in methanol/water (58/42, v/v).

The refractive index of the individual fractions was determined. FIG. 1 represents the refractive index profile of the peaks (labeled QA-1 to QA-22 in order of increasing retention times) from the RP-HPLC. The relative proportion of each peak in bark extract and Superfos "Quil-A" is shown on Table 1, below.

TABLE 1

Relative proportion of HPLC fractions of crude saponin extract and Superfos "Quil-A" (refractive index) % of Total (peaks 2–21)

| HPLC Fraction | Dialyzed, methanol-soluble bark extract | Superfos "Quil-A" |
|---|---|---|
| QA-2 | 3.1 | 1.2 |
| QA-3 | 4.8 | 2.4 |
| QA-4, 5 | 10.1 | 7.1 |
| QA-6, 7 | 17.5 | 12.7 |
| QA-8 | 6.8 | 10.5 |
| QA-9 | 1.0 | 2.1 |
| QA-10 | 2.7 | 1.3 |
| QA-11 | 6.8 | 6.2 |
| QA-12 | 3.5 | 5.6 |
| QA-13, 14, 15 | 4.8 | 7.7 |
| QA-16 | 2.8 | 1.4 |
| QA-17 | 11.4 | 9.9 |
| QA-18 | 13.5 | 21.8 |
| QA-19 | 2.2 | 4.5 |
| QA-20 | 3.2 | 2.2 |
| QA-21 | 5.6 | 3.7 |

The individual peaks correspond to single thin-layer chromatography bands on reverse-phase TLC plates. Another representative experiment shown on FIGS. 2A–2B demonstrate that the refractive index peaks also correspond to carbohydrate peaks, confirming that all major bark extract components are glycosides (HPLC fractions assayed for carbohydrate by the anthrone assay).

Dialyzed, methanol-soluble bark extract and "Quil-A" were compared directly in this HPLC system. The individual components were identified by retention time. All peaks present in dialyzed, methanolsoluble bark extract were also present in "Quil-A" in similar proportions with the exception of a higher proportion of component QA-8 and a lower proportion of component QA-17 in Superfos "Quil-A" compared to bark extract. FIG. 3 shows a comparison of dialyzed, methanol-soluble bark extract and Superfos "Quil-A" using a semipreparative Vydac $C_4$ (10 mm ID×25 cm L, 330 Å pore size, 5 µm particle size). The sample is loaded in 50% methanol in 40 mM acetic acid and a methanol gradient in 40 mM acetic acid (shown in FIG. 3A–3B) is used to elute the samples. The absorbance was monitored at 214 nm.

Various samples of Quillaja bark were extracted and analyzed by HPLC. There was some variability in the relative proportions of the peaks, but the same peaks were always present. It is not presently known whether the variability in proportions is due to variability in the efficiency of the extraction process or in bark from different sources.

Due to the ready availability of "Quil-A" and the similar composition to bark extract, "Quil-A" was utilized to produce mg quantities of material. Adjuvant activity in mice, using BSA as antigen, was found to be associated with peaks 4, 7, 11, 12, 15, 16, 17, 18, 19, and 20 (Table 2) at doses of 3.0 µg carbohydrate (determined by the anthrone assay). The absorbance due to antigen-specific antibody binding (two weeks post-immunization, determined by ELISA) at a sera dilution of 1:10 provides a semi-quantitative estimate of adjuvant activity (ranging frown 0.07 in mice immunized in the absence of adjuvant to 1.24 in mice immunized in the presence of QA-20).

TABLE 2

| | Adjuvant Activity in Mice | |
|---|---|---|
| HPLC Fraction | Adjuvant Dose µg carbohydrate) | Absorbance* (410 nm) |
| QA-2 | 3.0 | .34 |
| QA-3 | 3.0 | .27 |
| QA-4 | 3.0 | .60 |
| QA-7 | 3.0 | .49 |
| QA-10 | 3.0 | .13 |
| QA-11 | 3.0 | .46 |
| QA-12 | 3.0 | .76 |
| QA-13, 14 | 3.0 | .20 |
| QA-15 | 3.0 | 1.17 |
| QA-16 | 3.0 | .66 |
| QA-17 | 3.0 | 1.13 |
| QA-18 | 3.0 | .75 |
| QA-19 | 3.0 | .93 |
| QA-20 | 3.0 | 1.24 |
| — | — | 0.07 |

*Absorbance due to antigen-specific antibody binding at sera dilution of 1:10.

Due to the predominance of peaks QA-7, QA-17, QA-18, and QA-21 in bark extract, these four components were purified on a larger scale, as described in Examples 3 and 4, below.

EXAMPLE 3

PURIFICATION BY SILICA CHROMATOGRAPHY 1 gram "Quil-A" was suspended in 75 ml methanol and heated at 60° for 15 minutes and filtered. The undissolved material was extracted a second time with 50 ml methanol at 60° C. and filtered. The filtrates were evaporated to dryness on the rotoevaporator. A Lichropep Silica Si60 column (E.M. Science, 25 mm ID×310 mm L, 40–63 µm particle size) was pre-equilibrated in 40 mM acetic acid in chloroform/methanol/water (62/32/6, v/v/v).

The dried "Quil-A," a crude mixture of saponins, was dissolved in 5 ml of column solvent and eluted through the silica isocratically in this solvent system at a flow rate of 1 ml/min. Carbohydrate analysis, thinlayer chromatography, and HPLC were used to monitor the fractions for QA-7, QA-17, QA-18, and QA-21. Fractions 19–30 were enriched in QA-21 and were pooled for further purification of QA-21. Fractions 31–60 were enriched in QA-8 and QA-18 and were pooled for further purification of these components. Fractions 85–104 were enriched with QA-7 and QA-17 and were pooled for further purification of these components. These pools were flash evaporated prior to further purification.

EXAMPLE 4

FURTHER PURIFICATION BY REVERSE PHASE HPLC

Figure 4A:
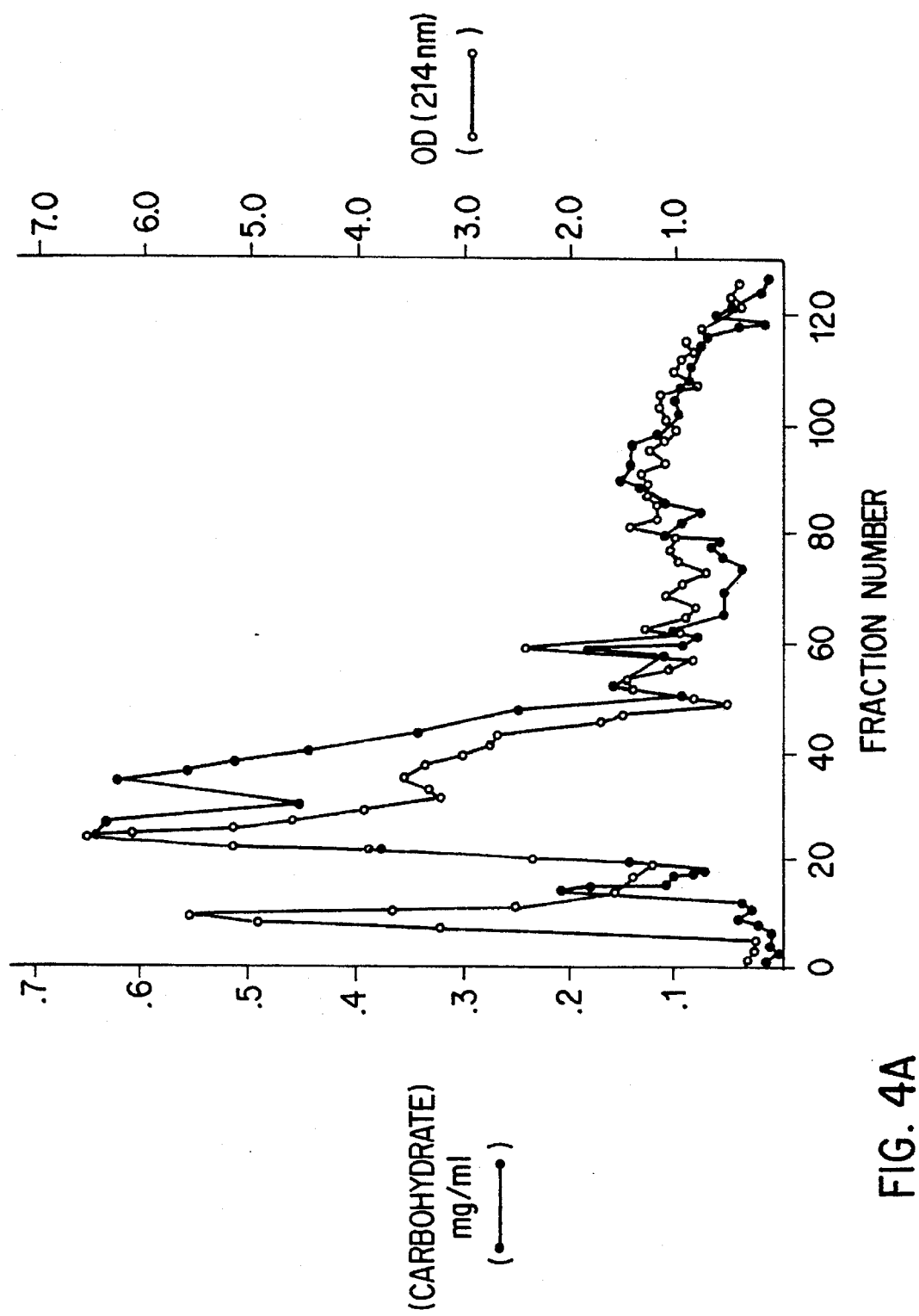
FIGS. 4A–4D show the purification of QA-7, QA-17, QA-18, QA-19, and QA-21 from "Quil-A,", a crude saponin mixture, by silica chromatography (FIG. 4A) and subsequent reverse phase chromatography (FIGS. 4B–4D).
Figure 4B:
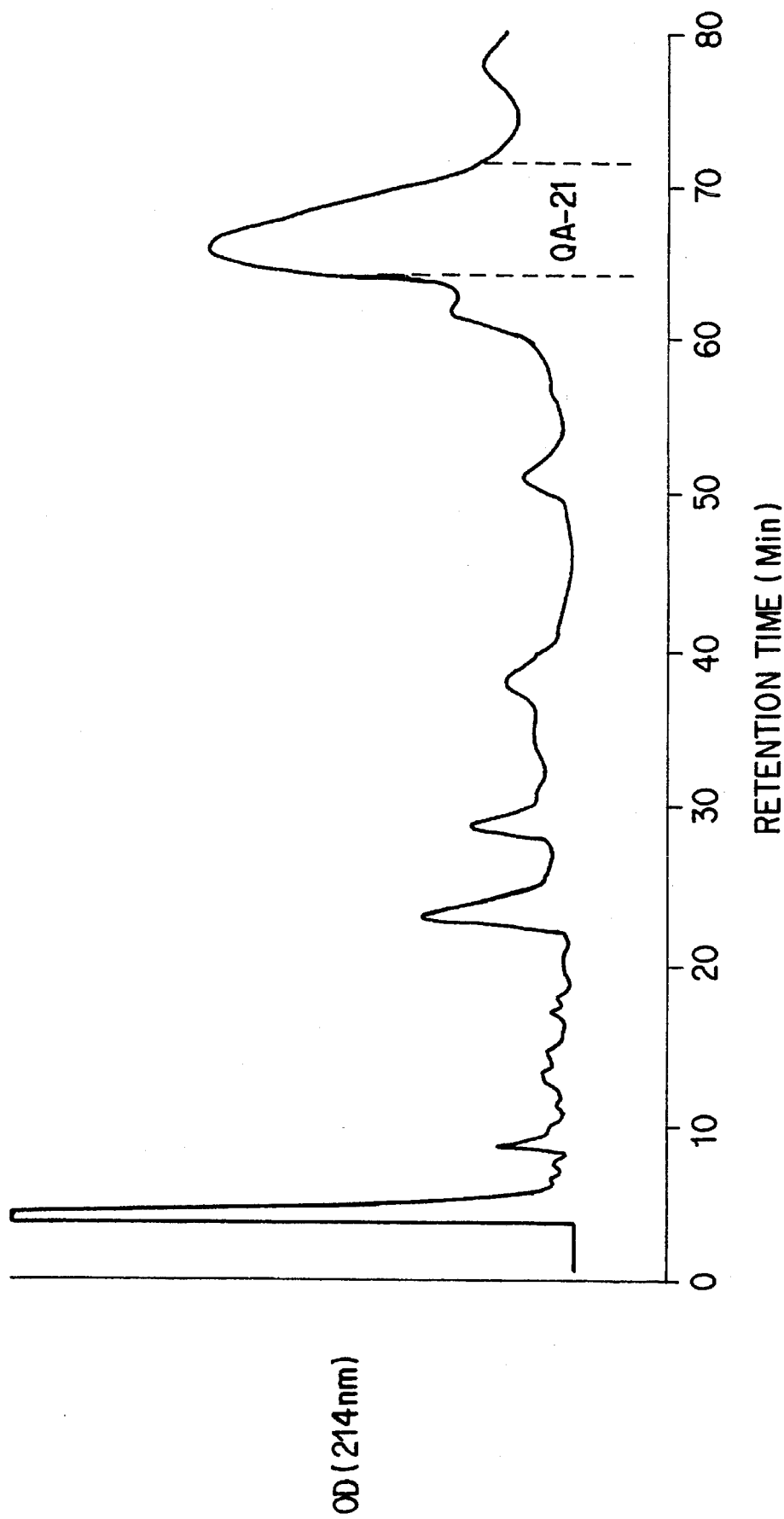
Figure 4C:
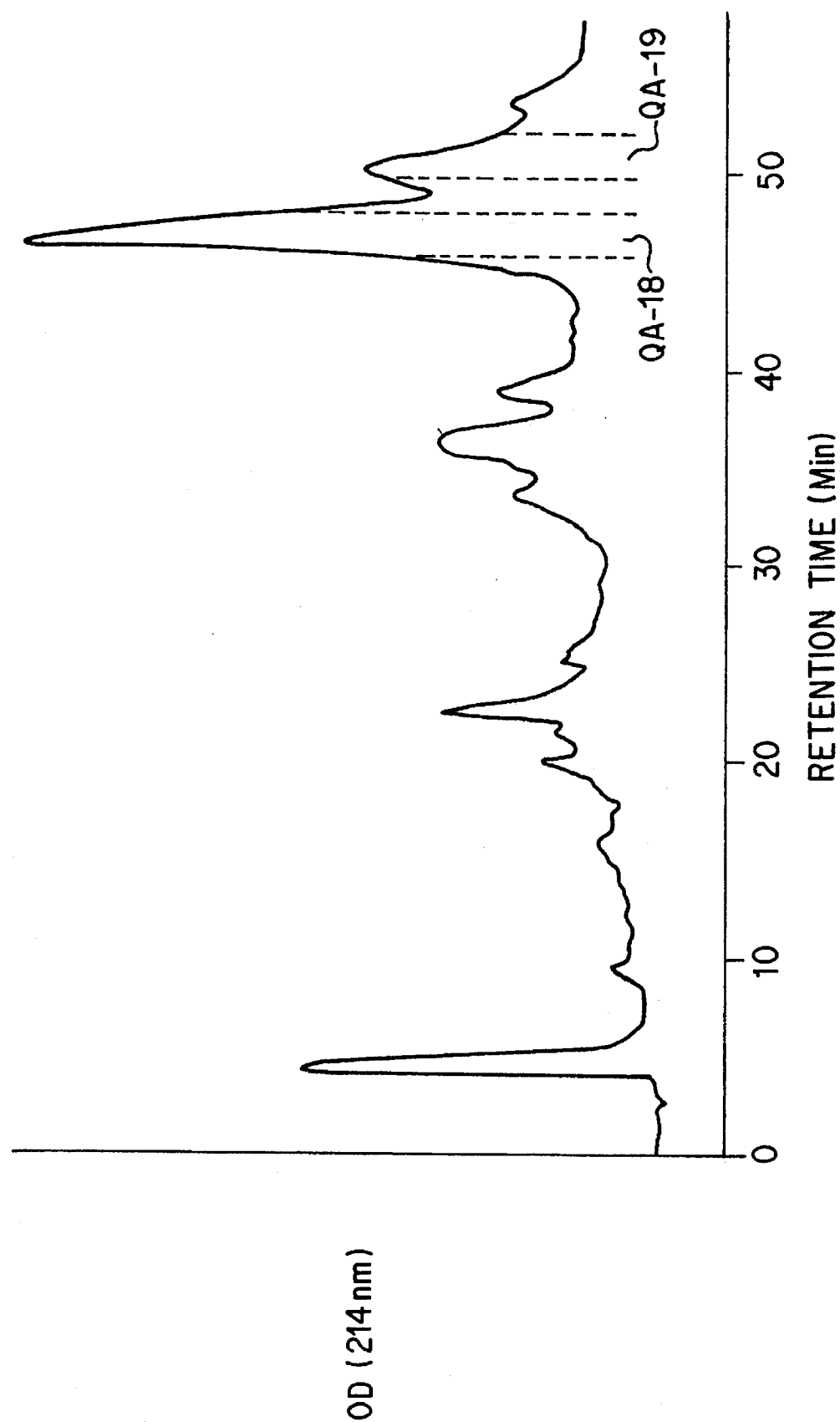
Figure 4D:
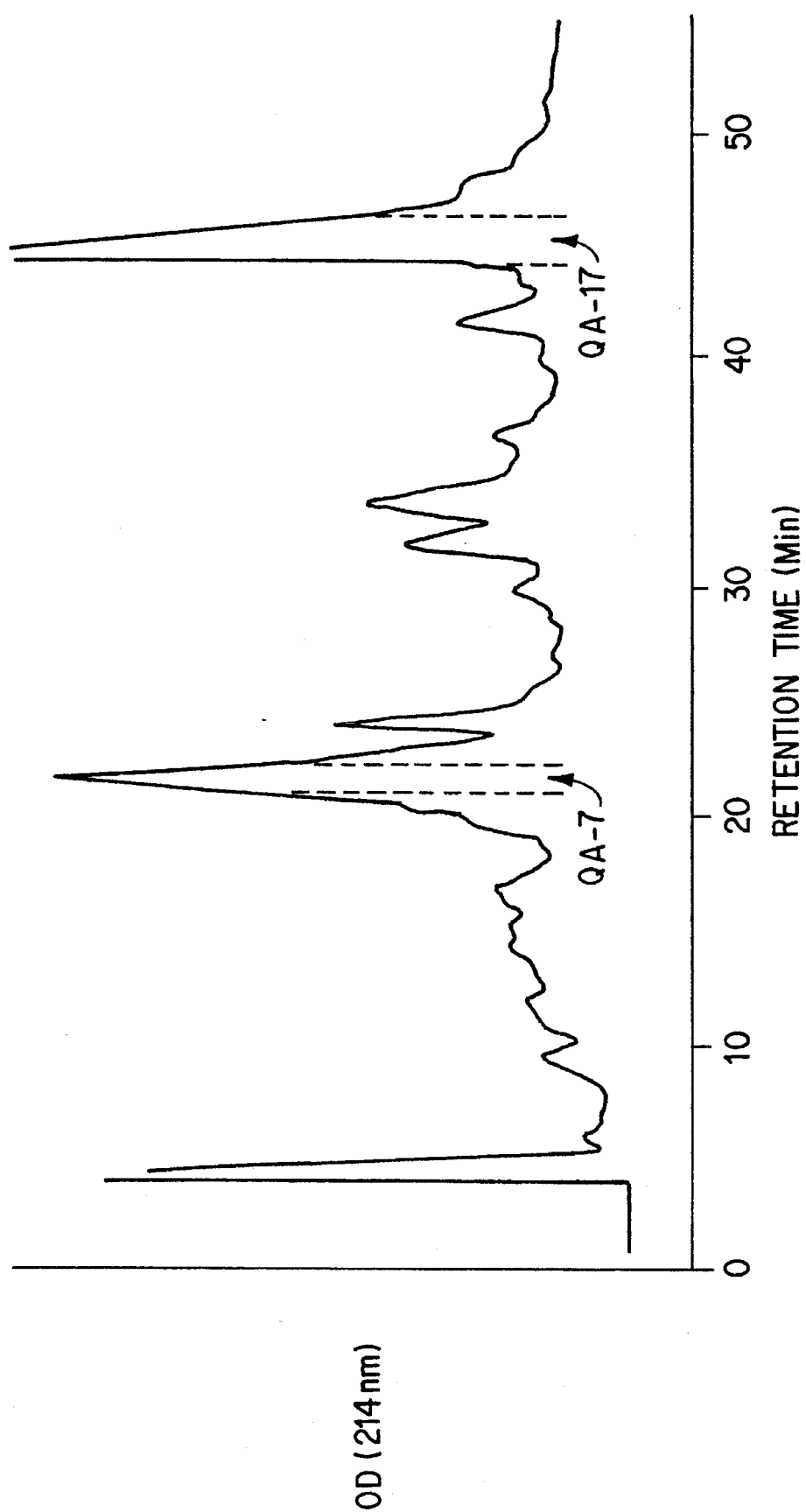

Silica fractions were further purified by semipreparative reverse phase HPLC on Vydac $C_4$ (10 mm ID×25 cm L), FIG. 4A–4D. Silica fractions (10–20 mg) were dissolved in the appropriate solvent and loaded on Vydac $C_4$. A methanol gradient was used to elute the fractions. The flow rate was 3 ml per minute. The fractions were monitored by absorbance at 214 nm. FIG. 4B shows the purification of QA-21 from silica fractions 19–30 using isocratic separation in 40 mM acetic acid in 58% methanol/42% water. Fractions eluting with a retention time between 65–72 minutes were identified as QA-21 by reverse phase TLC and pooled for further characterization. FIG. 4C shows the purification of QA-18 from silica fractions 31–60 using a methanol gradient in 40 mM acetic acid (50–56% methanol/0–10 min, 56–69% methanol/10–79 min). Fractions eluting with a retention time between 46–48 minutes were identified as QA-18 by reverse phase TLC and pooled for further characterization. FIG. 4D shows the purification of QA-7 and QA-17 from silica fractions 85–104 using the same gradient used in FIG. 4C. Fractions eluting with a retention time between 21–23 minutes were identified as QA-7 by reverse phase TLC and pooled for further characterization. Fractions eluting with a retention time between 44–46 minutes were identified as QA-17 by reverse phase TLC and were pooled for further characterization.

EXAMPLE 5

FURTHER PURIFICATION OF QA-21 BY HILIC

Figure 5A:
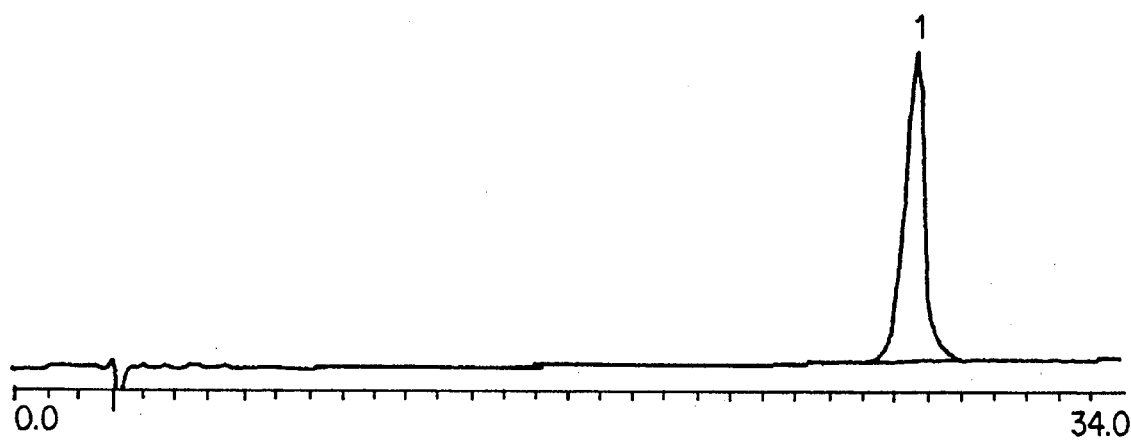
FIGS. 5A–5B show the reverse phase HPLC of QA-21 as a single peak (FIG. 5A) and the resolution into two peaks, QA-21-V1 and QA-21-V2, with hydrophilic interaction chromatography ("HILIC") (FIG. 5B).
Figure 5B:
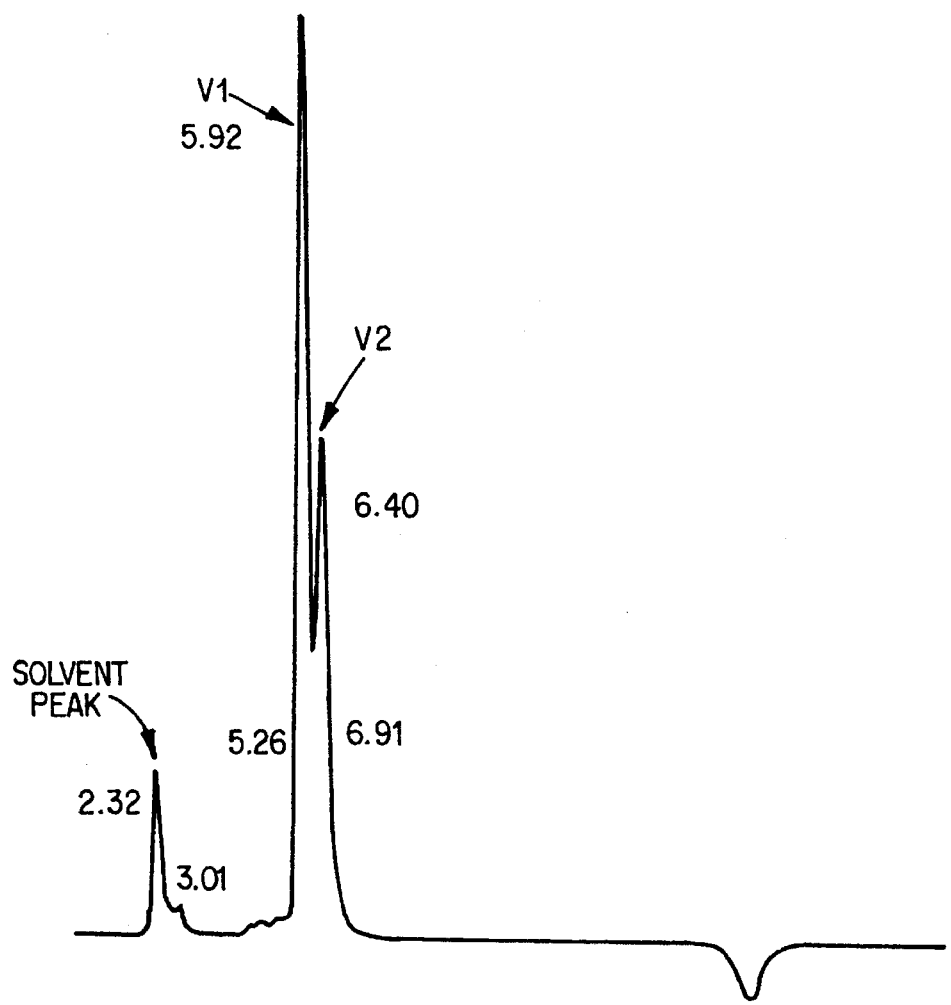

QA-21, which appeared pure by HPLC (FIG. 5A), was solubilized at 3 mg/ml in 10 mM triethylamine phosphate ("TEAP"), pH 6.0, in water/acetonitrile (15/85%, v/v). A 50 µl aliquot was loaded onto a PolyLC PHEA column (5 µm particle size, 4.6 mm ID×20 mm L) equilibrated in the same solvent (10 mM TEAP in 15% H20/85% acetonitrile). The sample was eluted isocratically at a flow rate of 1 ml/min and monitored by absorbance at 214 nm. Two peaks resulted, the first at 6.4 minutes (designated QA-21-V1) and the second at 6.9 minutes (QA-21-V2); ratios of the first peak to the second were typically 3:2 (FIG. 5B). Samples were prepared for analysis using a semipreparative scale PHEA column.

EXAMPLE 6

PURIFY AND CHARACTERIZATION OF ADJUVANTS PURIFIED BY SILICA AND REVERSE PHASE CHROMATOGRAPHY

Purity

Figure 6A:
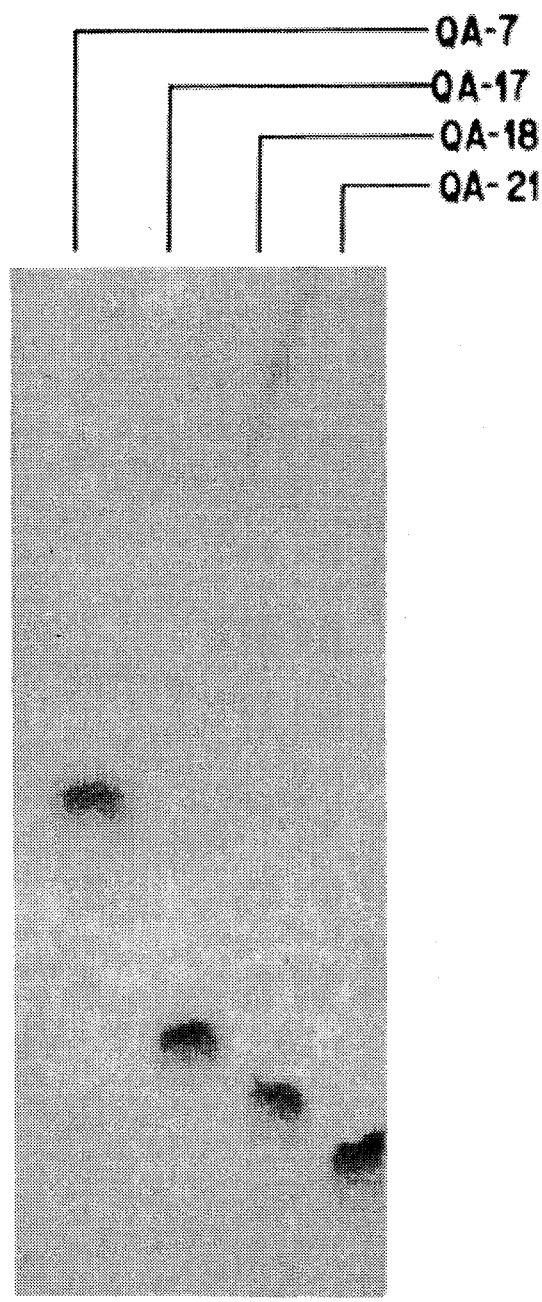
FIGS. 6A–6B demonstrate the purity of QA-7, QA-17, QA-18, and QA-21 by reverse phase (FIG. 6A) and normal phase (FIG. 6B) thin layer chromatography.

FIG. 6A represents a reverse-phase TLC (E.M. Science RP-TLC, C8 (Solvent=70% methanol, visualization spray= Bial's reagent)). 5 µg each of QA-7, QA-17, QA-18, and QA-21 purified as described in Example 3 and 4, were chromatographed. The adjuvants each appeared as single bands in this TLC system.

Figure 6B:
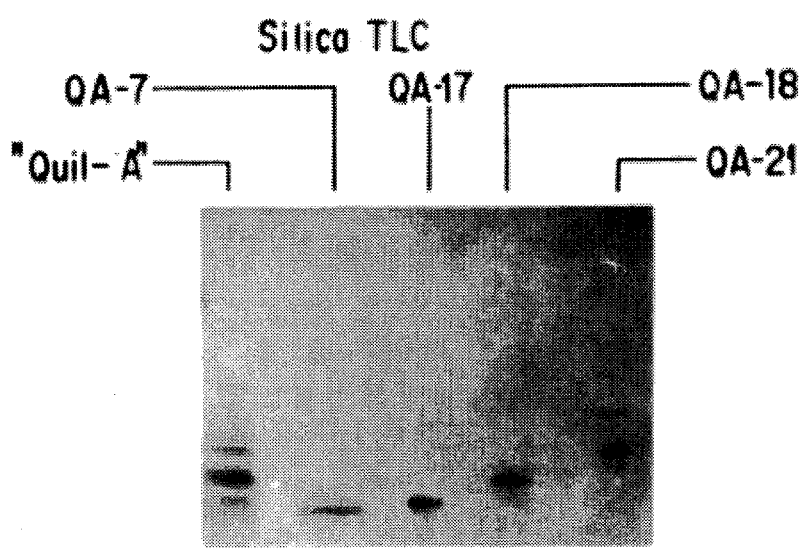
Figure 7:
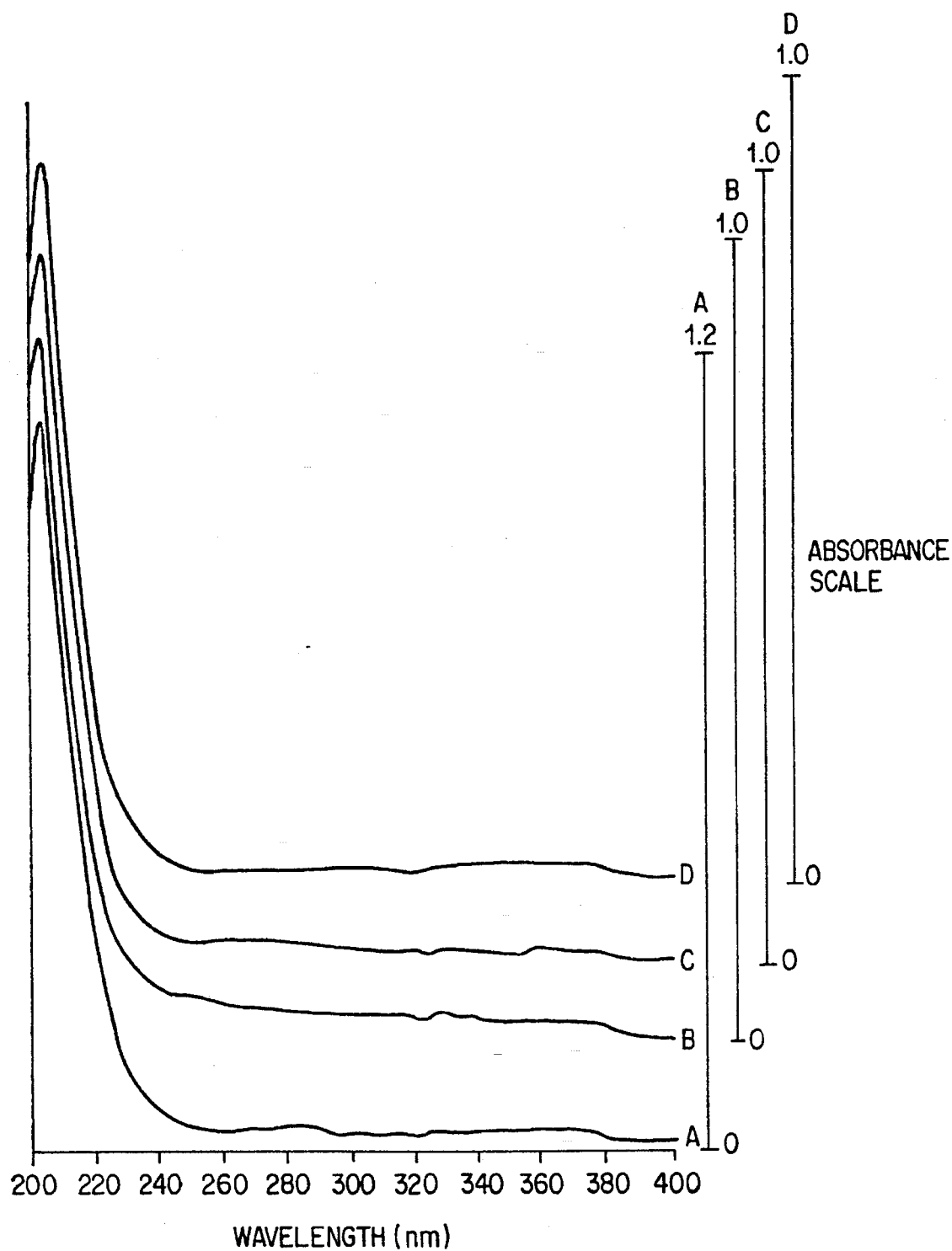
FIG. 7 shows the UV spectrum of QA-7 (A), the UV spectrum of QA-17 (B), the UV spectrum of QA-18 (C), and the UV spectrum of QA-21 (D).

FIG. 6B demonstrates fractions QA-7, QA-17, QA-18, QA-21 and "Quil-A" on EM Si60 HPTLC plate (solvent=40 mM acetic acid in chloroform/methanol/H$_2$O (60/45/10, v/v/v), visualization spray=Bial's reagent). 2/µg each of QA-7, QA-17, QA-18 and QA-21, purified as described in Examples 3 and 4, and 20 µg of "Quit-A," a crude saponin extract, were chromatographed. The HPLC-purified material appeared predominantly as a single band, although QA-21 was subsequently separated into two components, as described in Example 5.

Spectroscopy

The UV spectra of QA-7, QA-17, QA-18 and QA-21 in methanol are shown on FIGS. 7A–D respectively. Dalsgaard's (Dalsgaard, K.,*Acta Veterinaria Scandinavica Supp.* 69:1–40 (1978)) adjuvant fraction had an absorbance peak at 280 nm; however, the HPLC-purified fractions of the present invention do not have a peak at 280 nm but have a major peak in the region between 200–220 nm with a shoulder centered at 260 nm.

Fourier Transform-Infrared Resonance ("FT-IR") spectra showed little difference between the adjuvants, suggesting that they all have the same functional groups. Although identification of the structure cannot be made from the IR, the spectral data is consistent with the presence of a carboxyl group as was suggested by Dalsgaard (Dalsgaard, K., supra).

Figure 8A:
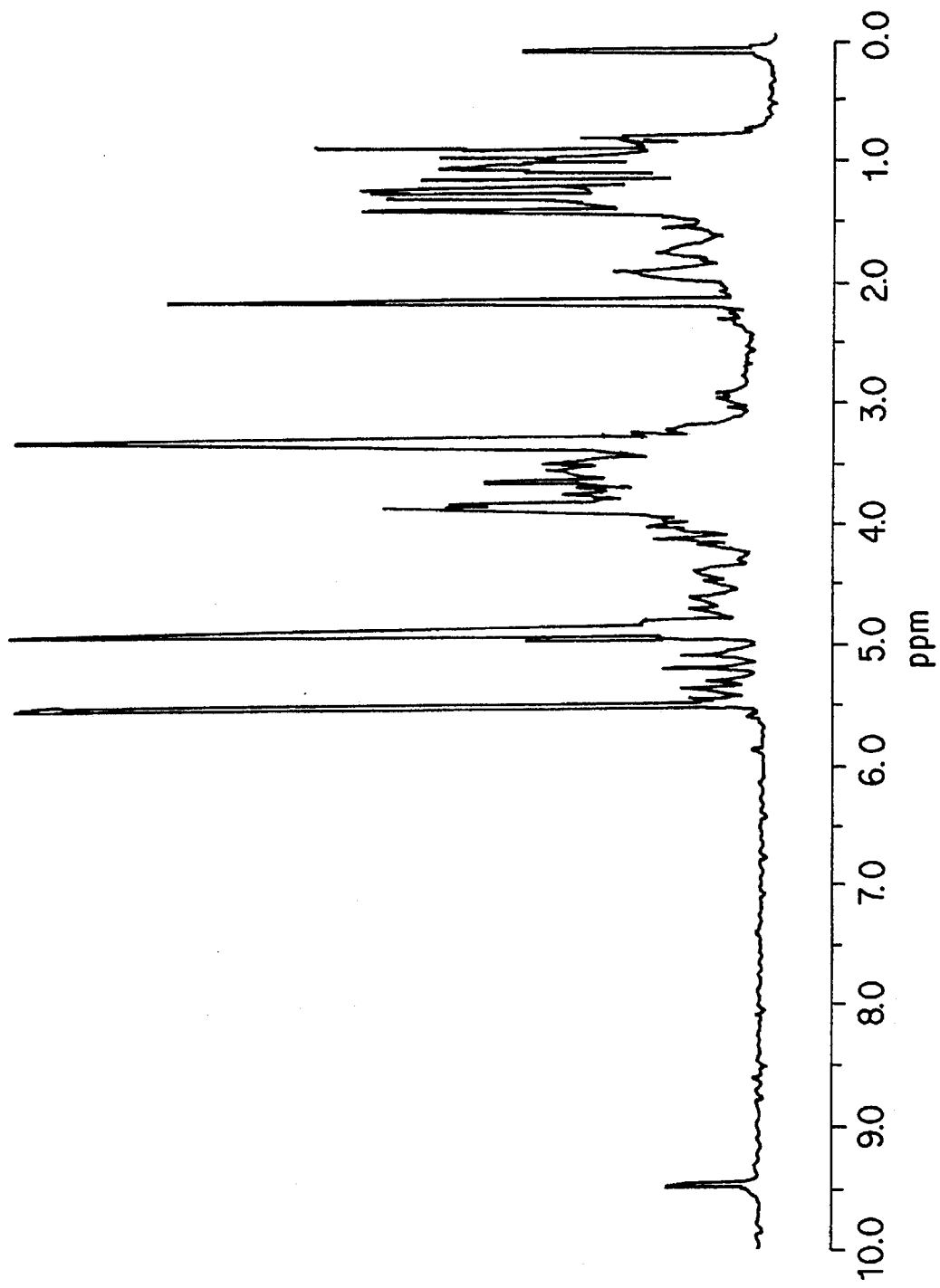
FIG. 8A shows $^1H$ Nuclear Magnetic Resonance ("NMR") of QA-7.
Figure 8B:
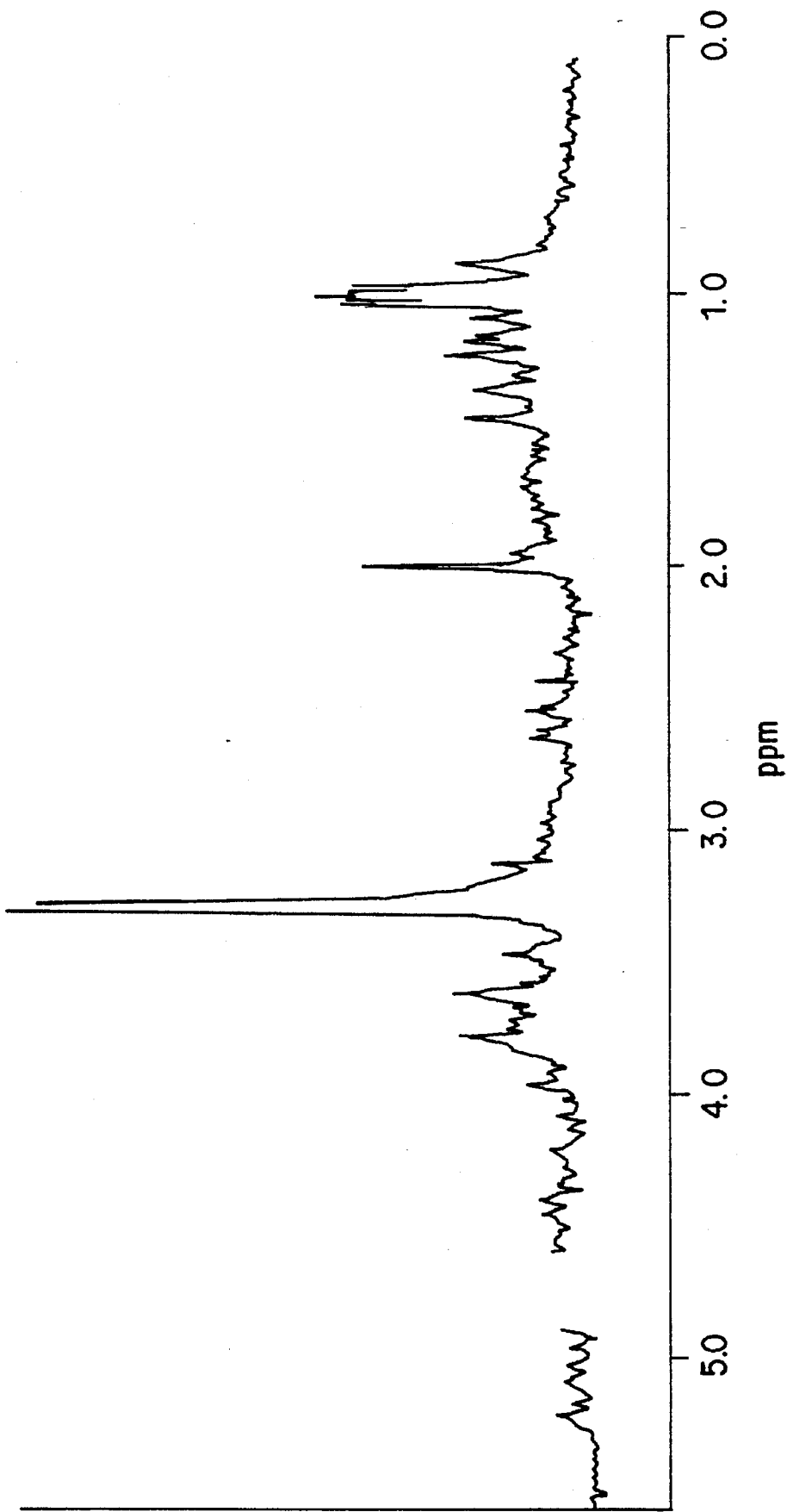
FIG. 8B shows $^1H$ NMR of QA-18.
Figure 8C:
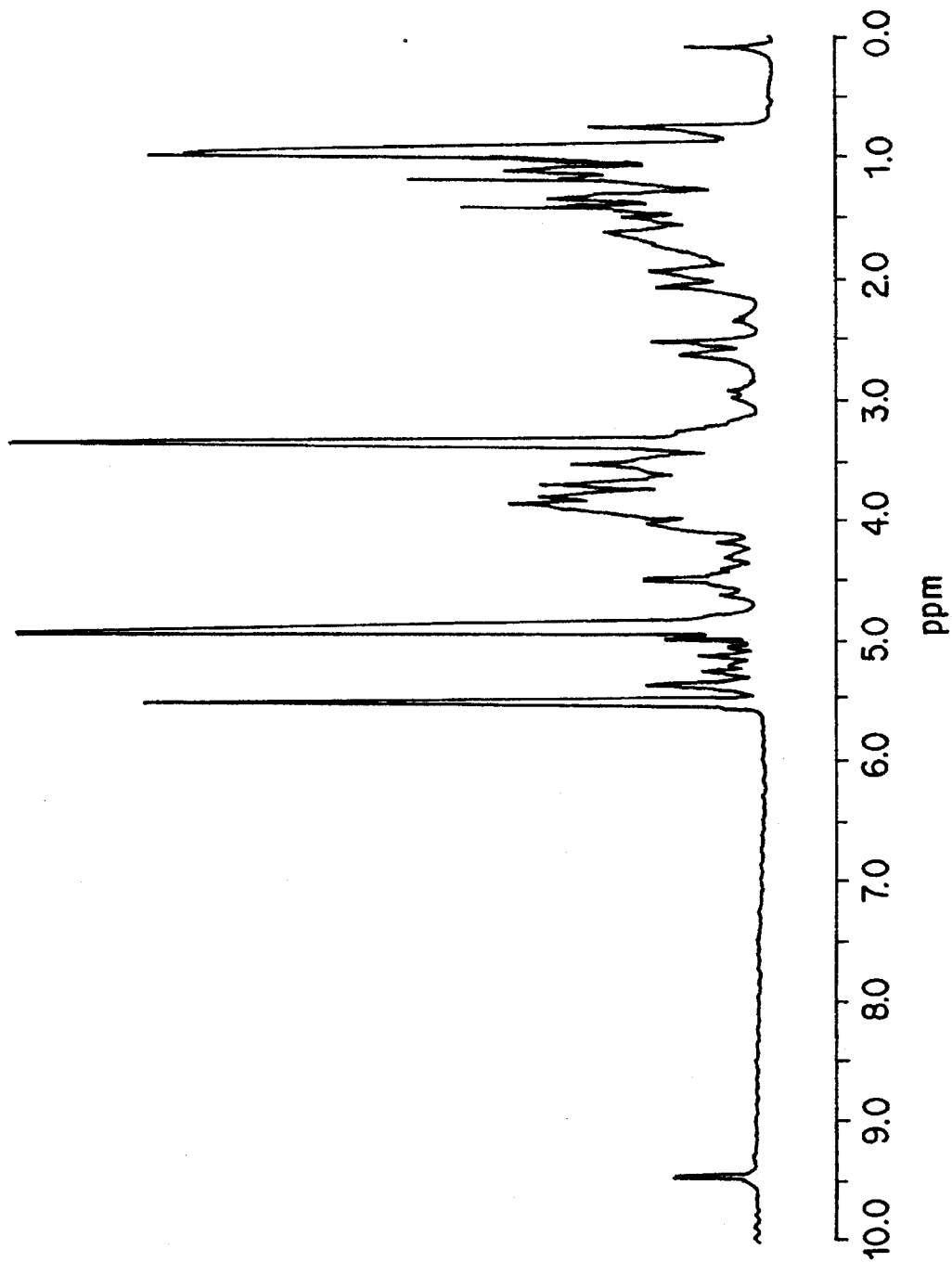
FIG. 8C shows $^1H$ NMR of QA-21.

$^1$H-NMR at 250 MHz of the purified saponins in CD$_3$OD demonstrates the complex nature of the purified saponins QA-7 (FIG. 8A), QA-18 (FIG. 8B), and QA-21 (FIG. 8C). The signals in the region between 4.1 to 5.4 ppm clearly demonstrate the presence of multiple signals from the anomeric protons of the monosaccharides, indicating a multiplicity of monosaccharide resides. However, the NMR spectra of the saponins are too complex to allow structural determination.

Figure 9A:
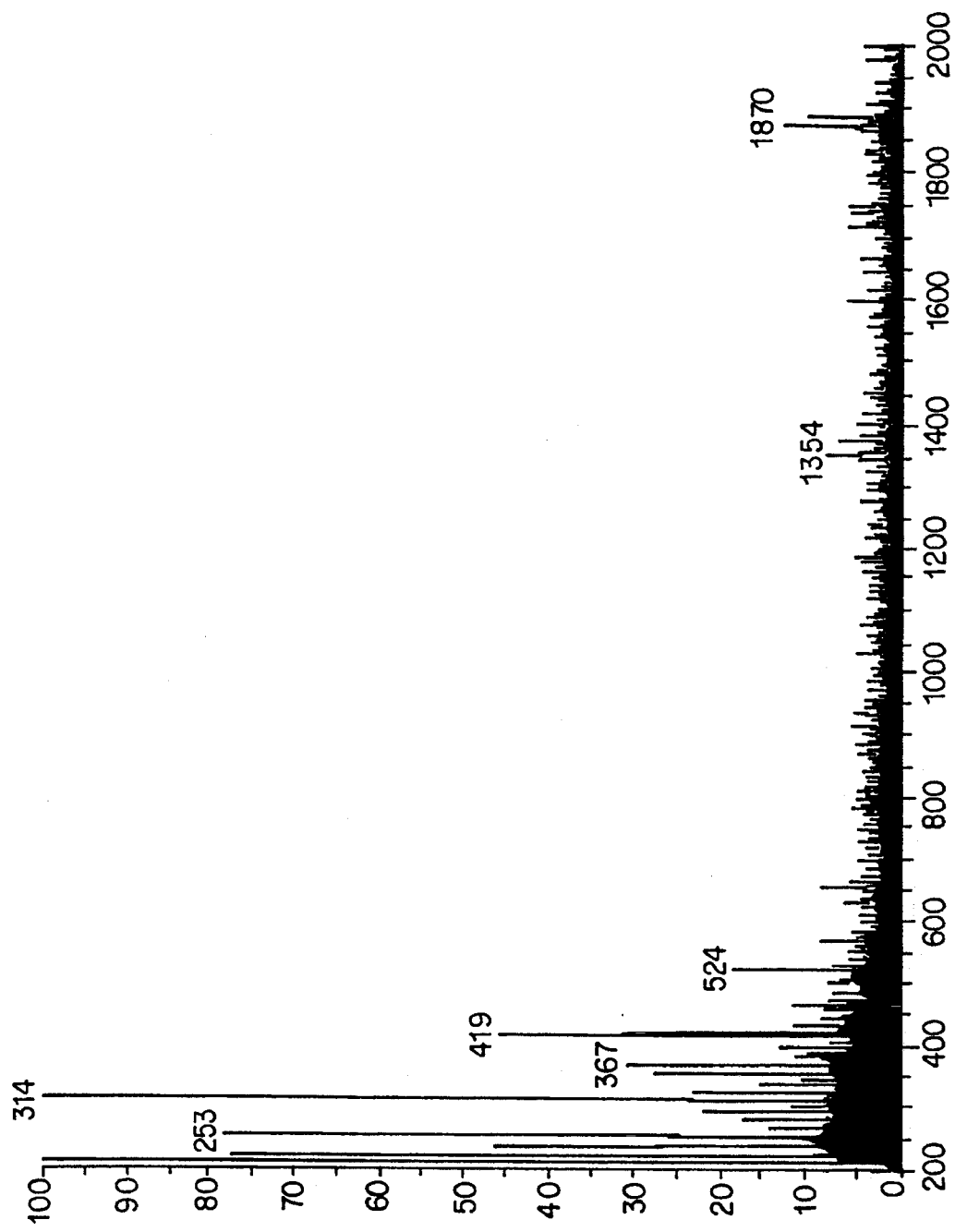
FIGS. 9A–9F show the mass spectroscopy-fast atom bombardment ("MS-FAB") spectrum of QA-7 (FIG. 9A), QA-17 (FIG. 9B), QA-18 (FIG. 9C), QA-21 (FIG. 9D), QA-21-V1 (FIG. 9E) and QA-21-V2 (FIG. 9F).
Figure 9B:
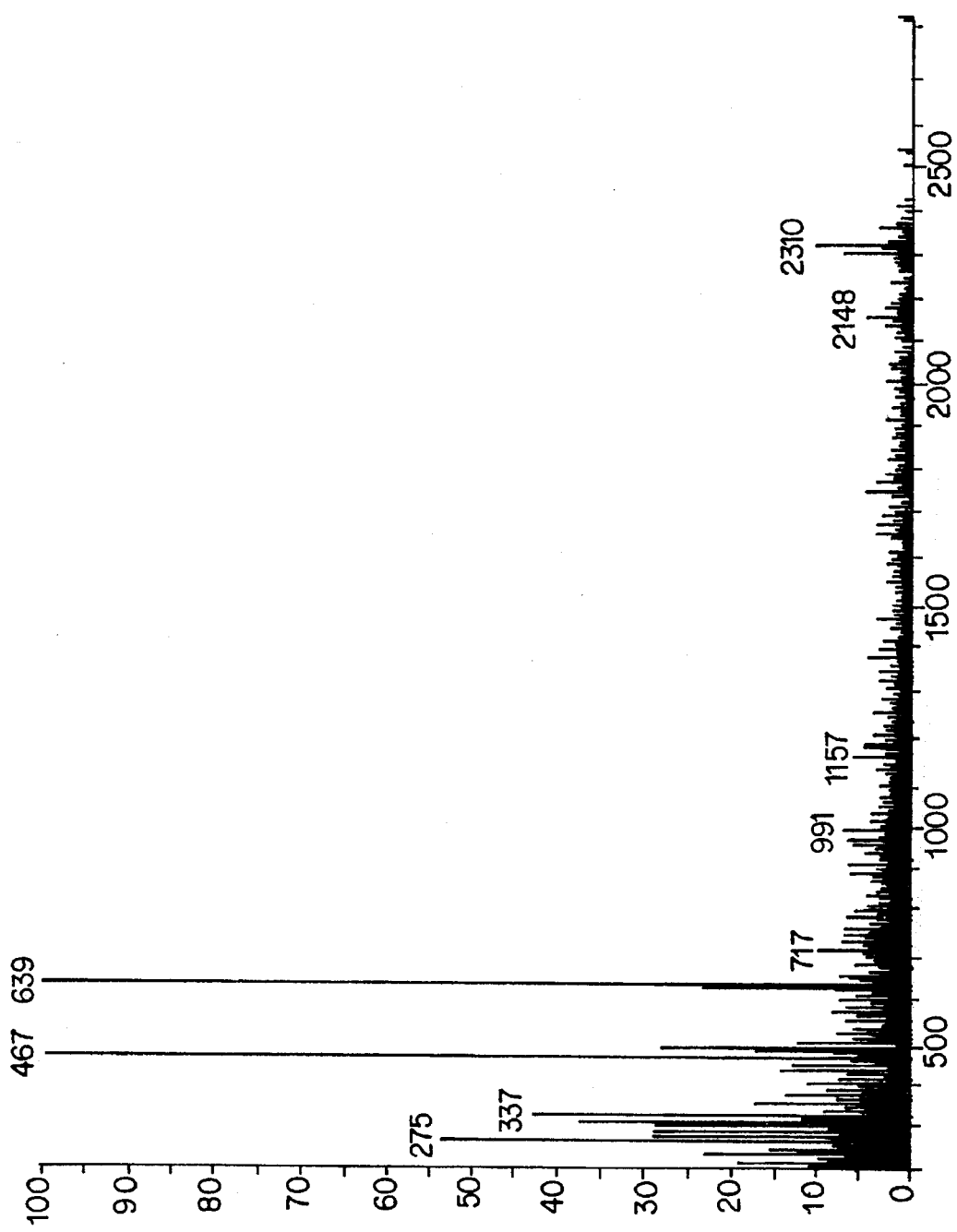
Figure 9C:
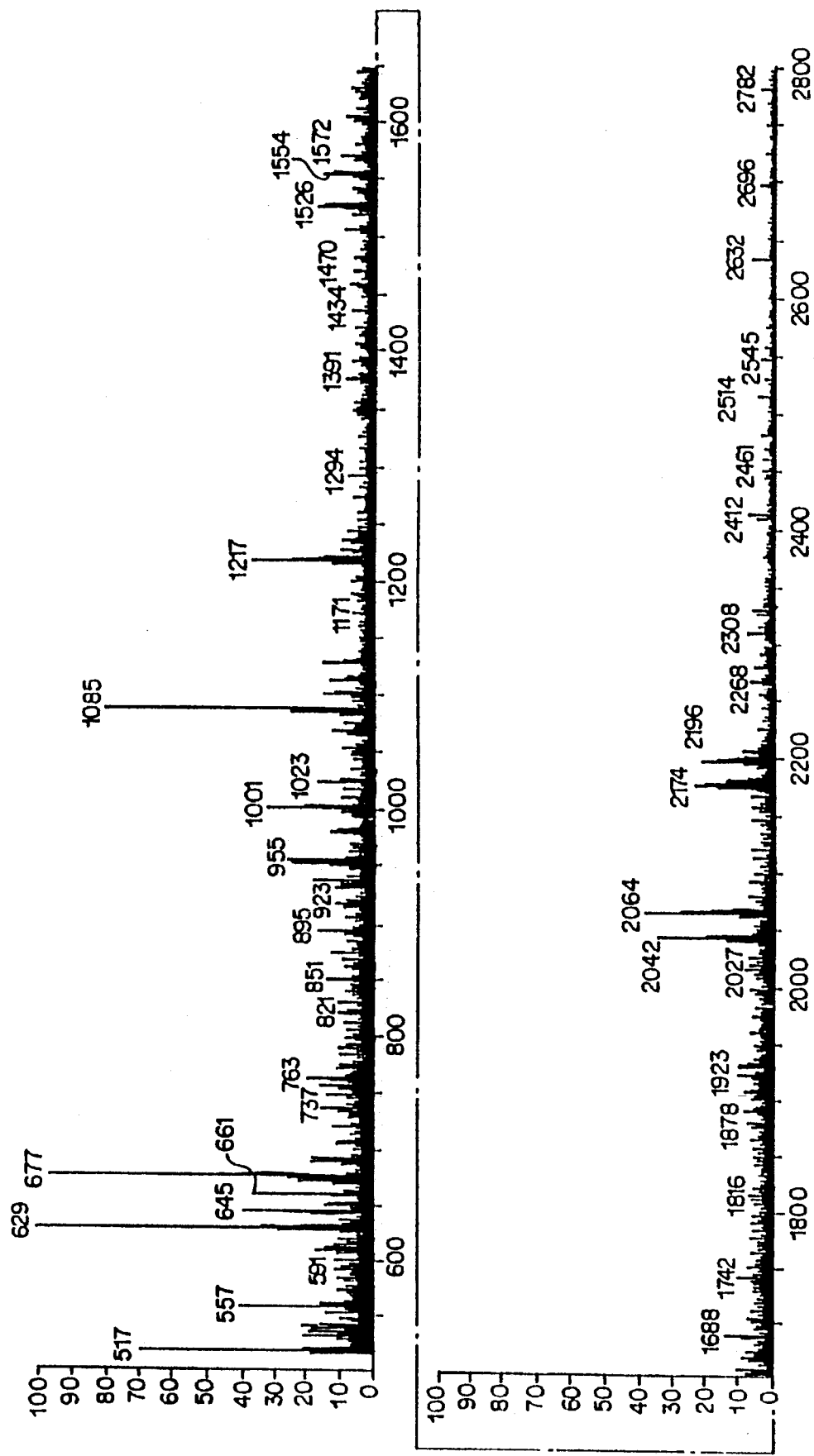
Figure 9D:
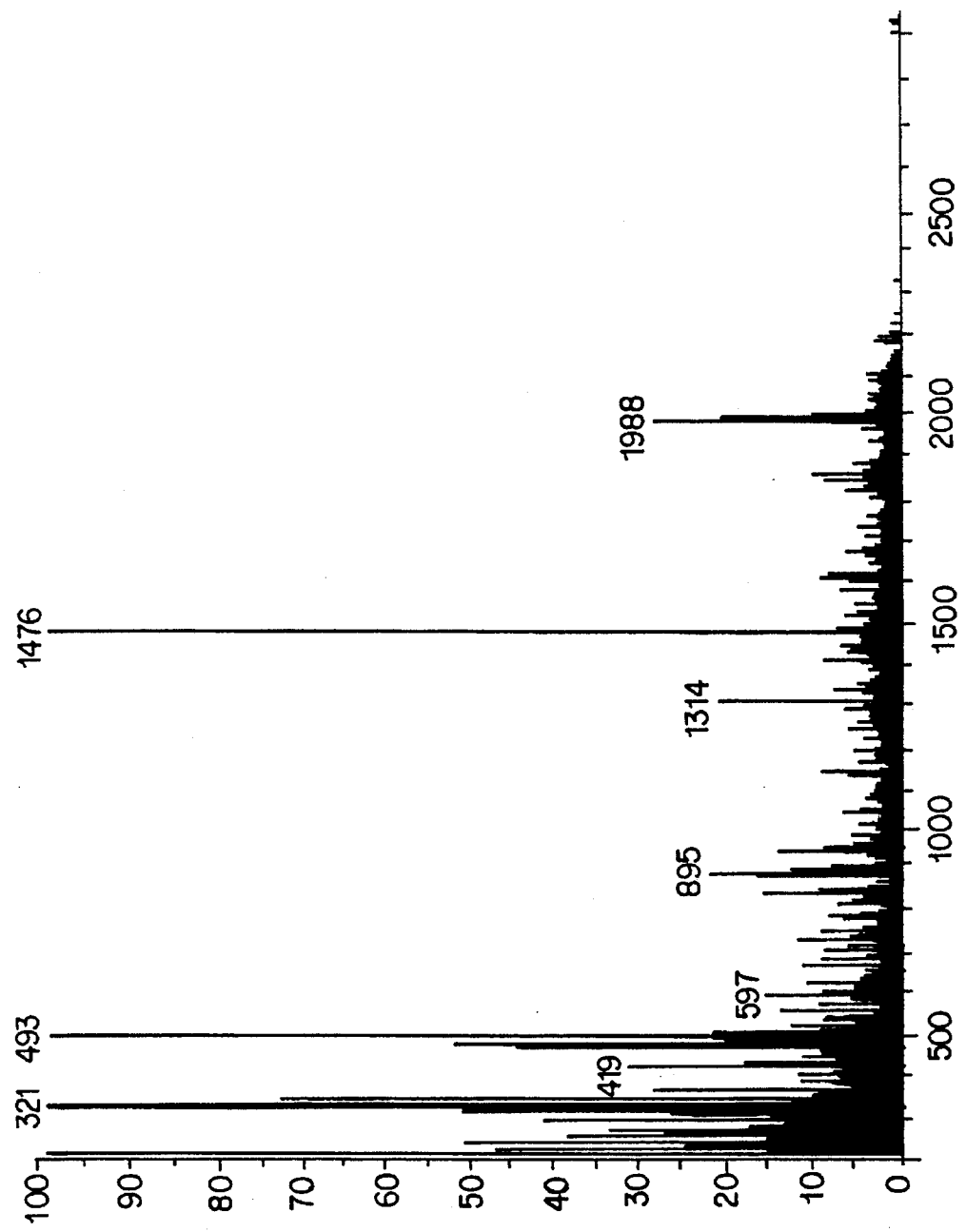
Figure 9E:
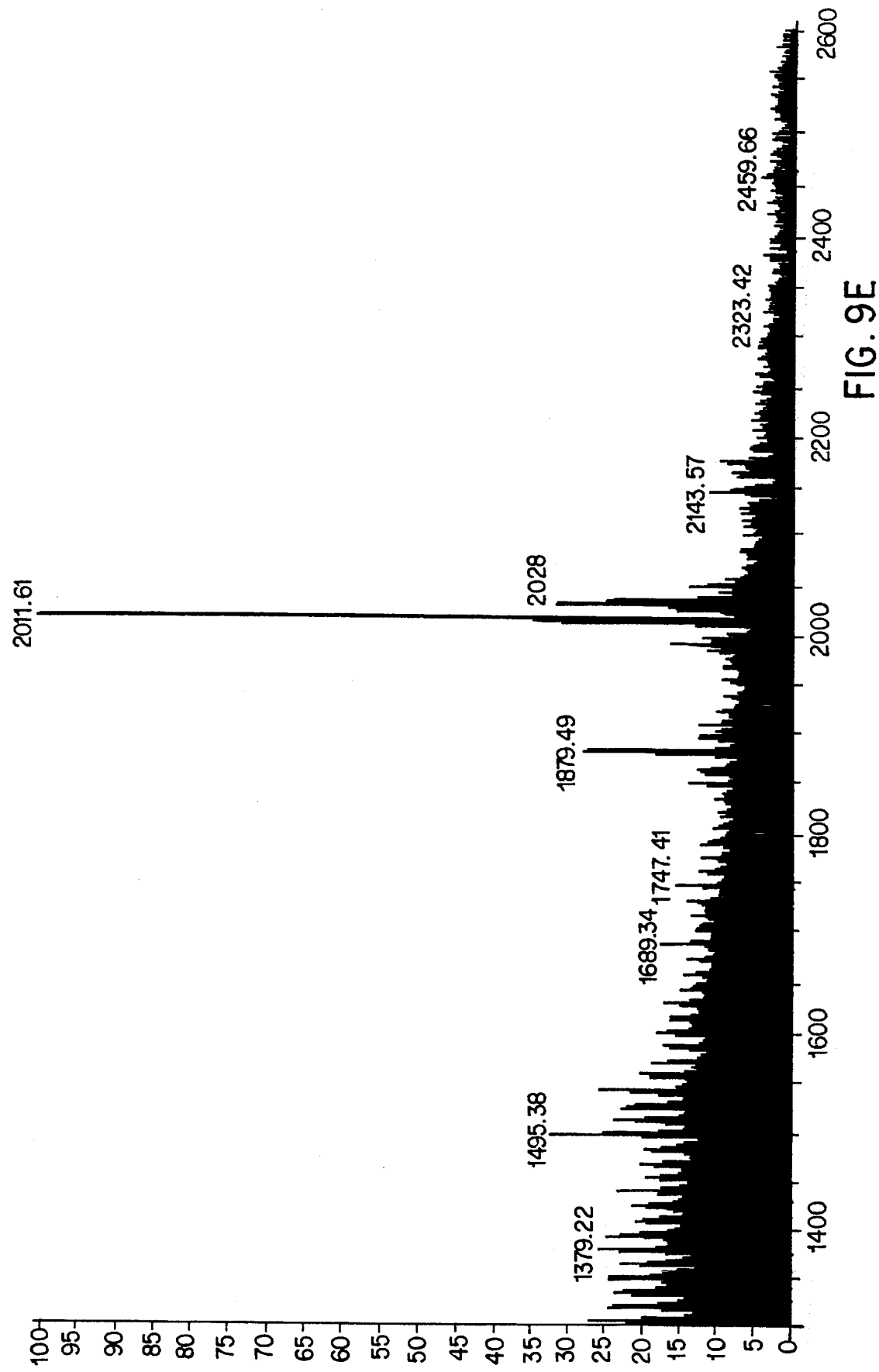
Figure 9F:
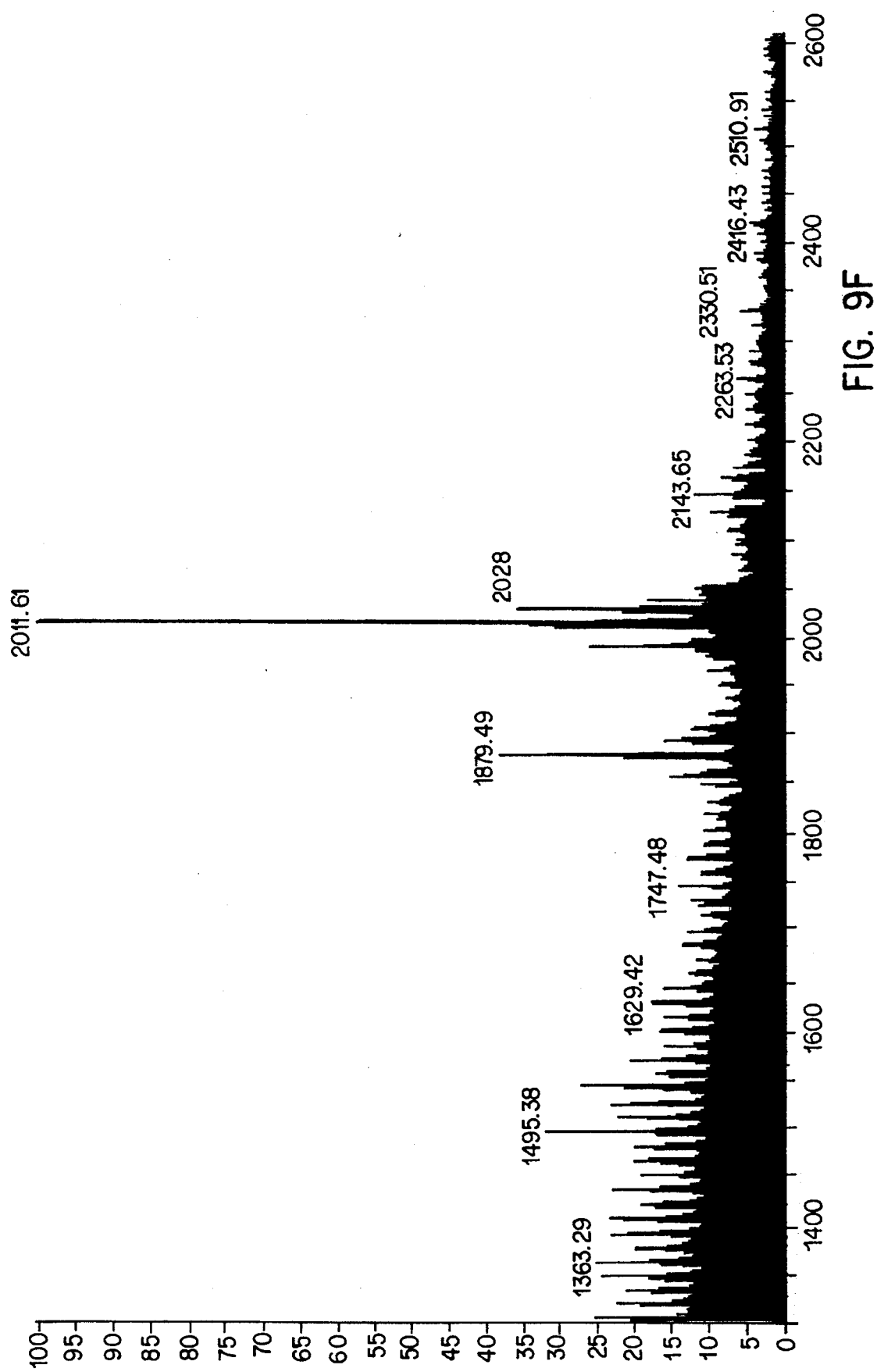

MS-FAB of the purified saponins QA-7, QA-17, and QA-21 (FIGS. 9A, 9B, and 9D, respectively) indicated approximate pseudo-molecular ion masses of 1870, 2310, and 1988, respectively. Repeated MS-FAB of QA-7, QA-17 and QA-21 (data not shown) indicated ion masses of 1885, 2321 and 2012, respectively, which may be the true ion masses. MS-FAB was also carried out on further purified saponins QA-21-V1 and QA-21-V2 (FIGS. 9E and 9F, respectively) indicating an approximate pseudomolecular ion mass of 2012 for each. This result is expected since the two structures differ only in the identity of a terminal pentose—apiose and xylose, respectively. MS-FAB of the purified saponin QA-18 (FIG. 9C) indicated an ion mass of 2174. These molecular weights are consistent with those expected for a triterpene linked to eight to ten monosaccharide residues and were in the same range as monomer molecular weights determined by size exclusion HPLC of purified saponins in methanol (Zorbax PSM 60 Si column, 25 cm×6.2 mm, 1 ml/min flow rate, molecular weight standards =18-β-glycyrrhetinic acid and ginenoside Rb$_1$) which indicated approximate molecular weights of 2600, 2400, 1800, and 2400 for QA-7, QA-17, QA-18, and QA-21, respectively. The difference between FAB-MS and size exclusion HPLC are most likely due to variation in shape between the saponins and the molecular weight standards.

Carbohydrate Composition

Table 3 below shows the carbohydrate composition and linkage analysis of purified saponins QA-7, QA-17, QA-18, QA-21, and QA-19. Table 4 below shows the carbohydrate composition and linkage analysis of further purified saponins QA-21-V1 and QA-21-V2. The carbohydrate in saponins was converted to alditol acetates by heating 0.2 mg saponin in 0.3 ml 2N trifluoroacetic acid containing 0.1 mg/ml inositol at 120° C. for two hours. The acid was removed under a flow of air, and residual acid removed by the addition of isopropanol (2×0.25 ml), followed by blowing to dryness with air. The dry residue obtained was dissolved in 1M ammonium hydroxide (0.25 ml) containing 10 mg/ml sodium borodeuteride and kept for one hour at room temperature. Glacial acetic acid (0.1 ml) was added, and the solution was blown to dryness. Residual borate was removed by co-distilling with 10% acetic acid in methanol (3×0.25 ml) and finally with methanol (2×0.25 ml). The dry residue in acetic anhydride (0.1 ml) and pyridine (0.1 ml) was heated for 20 minutes at 120° C. Toluene (9.02 ml) was added to the cooled solution, and the solvents removed under a flow of air. This procedure of adding toluene and removing pyridine and acetic anhydride was repeated twice. The residue obtained was taken up in dichloromethane (0.5 ml) and extracted with water (0.5 ml). The organic phase was transferred to a clean tube and dried. Prior to analysis by GLC (gas-liquid chromatography), the residue was dissolved in acetone (0.1 ml). Alditol acetates were analyzed on an SP2330 capillary GLC column (30 m×0.25 min) at 235° C.) with flame ionization detection. The carbohydrate in saponins was converted to trimethylsilated methylglycosides by heating 0.1 mg of sample in methanolic HCl (0.3 ml) containing 50 μg/ml inositol for 16 hours at 80° C. The sample was blown to dryness, and residual acid removed by the addition of t-butyl alcohol (2×0.25 ml) followed by drying with a flow of air. The dry residue was dissolved in a solution (0.2 ml) containing pyridine, hexamethyldisilazane, and trimethylchlorosilane (5:1:0.5 v/v, "Tri-Sil") and heated for 20 minutes at 80° C. The silylating reagent was evaporated at room temperature, and the residue dissolved in hexane (1 ml). After removal of the insoluble residue by filtration using glass wool plug, the filtrate was transferred to a clean tube and evaporated. The residue was dissolved in hexane (0.2 ml) prior to analysis by GLC. The trimethylsilated methyl glycosides were analyzed on a GLC column of fused silica DB1 (25 m×0.25 μm) for 3 min at 160° C. followed by a 2°/min increase to 200° C. and then a 10°/min increase to 260° C. with flame ionization detection.

solution. The clear solution was applied to the cartridge which was washed with water (8 ml) and 20% acetonitrile (5 ml). The methylated material was eluted from the cartridge with 100% acetonitrile (4 ml) and ethanol (4 ml). The solvents were removed with a flow of air. The dried methylated material was treated with 0.3 ml of "super deuteride" solution at room temperature for one hour in order to reduce the uronic acid residues to the corresponding hexoses. After destroying the excess reagent with glacial acetic acid (0.1 ml), the reaction mixture was blown to dryness with 10% acetic acid/methanol and blown to dryness two more times. The resulting reduced methylated material in methanol was passed through a column of Dowex—50 W($H^+$) and the effluent obtained was dried. The reduced methylated material was converted to methylated alditols as described in section 1 above and analyzed by GLC (SP2330 fused silica column (30 m×0.25 mm), 3 min at 170° C. followed by 4°/min to 240° C.) and GLC-MS (SP2330 fused silica column (30 m×0.25 mm), 2 min at 80° C. followed by 30°/min to 170° C. followed by 4° /min to 240° C. followed by holding at 240° C. for 10 min, mass spectral analysis on Hewlett-Packard MSD).

Despite the similarity in the carbohydrate composition, subtle differences distinguish the individual saponins, such as the absence of arabinose in QA-7 compared to the other saponins.

TABLE 3

Carbohydrate Composition and Linkage Analysis of Purified Saponins

| | QA-7 | | | QA-17 | | | QA-18 | | | QA-19A | | | QA-21 | | |
|---|---|---|---|---|---|---|---|---|---|---|---|---|---|---|---|
| | AA[a] | TMS[b] | Linkage | AA | TMS | Linkage | AA | TMS | Linkage | AA | TMS | Linkage | AA | TMS | Linkage |
| rhamnose | 191.4 | 1.57 | T[c] 3, 4 | 184.8 | 1.9 | T 3, 4 | 132.0 | 0.99 | T[f] 3, 4 | 32.7 | 1.69 | T 3, 4 | 131.9 | 1.07 | T[f] 4 |
| fucose | 86.7 | 0.67 | 2, 3 | 77.9 | 0.78 | 2 | 95.6 | 0.76 | 2 | 26.6 | 0.88 | 2 | 99.8 | 0.76 | 2 |
| arabinose | trace | trace | | 65.4 | 0.80 | 2 | 80.1 | 0.64 | T | 31.1 | 0.94 | T | 71.0 | 0.65 | T |
| xylose | 98.1 | 0.95 | T 3 | 81.8 | 1.08 | T 3 | 117.8 | 1.16 | T 3 | 49.9 | 2.07 | T 3 | 114.3 | 1.21 | T 3 |
| galactose | 81.2 | 0.74 | T | 69.4 | 0.81 | T | 88.1 | 0.86 | T | trace | 1.11 | T | 88.1 | 0.84 | T |
| glucose | 81.2 | 1.0 | T | 85.7 | 1.0 | T | 89.2 | 1.00 | T | trace | 1.0 | T | 19.6 | 0.30 | T |
| glucuronic acid | N.T.[d] | 0.48 | 2, 3 | N.T. | 0.52 | 2, 3 | N.T. | 0.62 | 2, 3 | 29.2 | 0.62 | 2, 3 | N.T. | 0.62 | 2, 3 |
| apiose[e] | 22.5 | N.T. | | 24.5 | N.T. | | 25.7 | N.T. | T | 27.7 | | T | 20.0 | N.T. | T |

[a]Alditol acetate (ug/mg saponin)
[b]Trimethylsilated methyl glycosides (relative proportions)
[c]T-terminal glycosyl residue, that is, attached through C-1 but with no other residues attached to it. 3, 4 = a glycosyl residue attached through C-1 with other glycosyl residues glycosidically attached to it through C-3 and C-4.
[d]Not tested
[e]Poor recovery as alditol acetates
[f]Present in trace amounts Glycoside linkage analysis was carried out by the following method: To the sample (≈1 mg) dissolved in dry dimethylsulfoxide (0.2 ml), 0.2 ml of potassium dimethylsulphinyl union (2M) was added, and the mixture stirred for 12 hours under argon. The reaction mixture was cooled in ice, and methyl iodide (0.2 ml) was added drop wise. The resulting mixture was sonicated and stirred at room temperature for one hour. The methylated material was isolated using Sep-Pak $C_{18}$ cartridges conditioned with ethanol (20 ml), acetonitrile (8 ml), and water (10 ml). Water (1 ml) was added to the methylation reaction mixture, and the excess methyl iodide removed by passing nitrogen through the

TABLE 4

Carbohydrate Analysis and Linkage Analysis of Purified Saponins

| | QA-21-V1 | | | QA-21-V2[d] | | |
|---|---|---|---|---|---|---|
| | weight %[a] | mol ratio[b] | linkage[c] | weight % | mole ratio | linkage |
| rhamnose | 14 | 1.0 | 4 | 14 | 1.0 | 4 |
| fucose | 13 | 1.0 | 2 | 15 | 1.0 | 2 |
| arabinose | 12 | 1.0 | T | 13 | 1.0 | T |
| xylose | 27 | 2.2 | T, 3 | 43 | 3.4 | T, 3 |

TABLE 4-continued

Carbohydrate Analysis and Linkage Analysis of Purified Saponins

| | QA-21-V1 | | | QA-21-V2[d] | | |
|---|---|---|---|---|---|---|
| | weight %[a] | mol ratio[b] | linkage[c] | weight % | mole ratio | linkage |
| galactose | 13 | 0.9 | T | 15 | 1.0 | T |
| glucuronic acid | 16 | 1.1 | 2, 3 | N.D.[f] | N.D. | 2, 3 |
| apiose[g] | 4.6 | 0.4 | T | 0 | 0 | N.D. |

[a]Relative weight percent of total carbohydrates in the samples.
[b]Mol ratio normalized to rhamnose.
[c]T = terminal glycosyl residue; number indicates position of linkage to other glycosyl residue.
[d]Results based only on alditol acetate analysis.
[e]Trace.
[f]Not determined.
[g]Poor recovery as alditol acetate.

Figure 10:
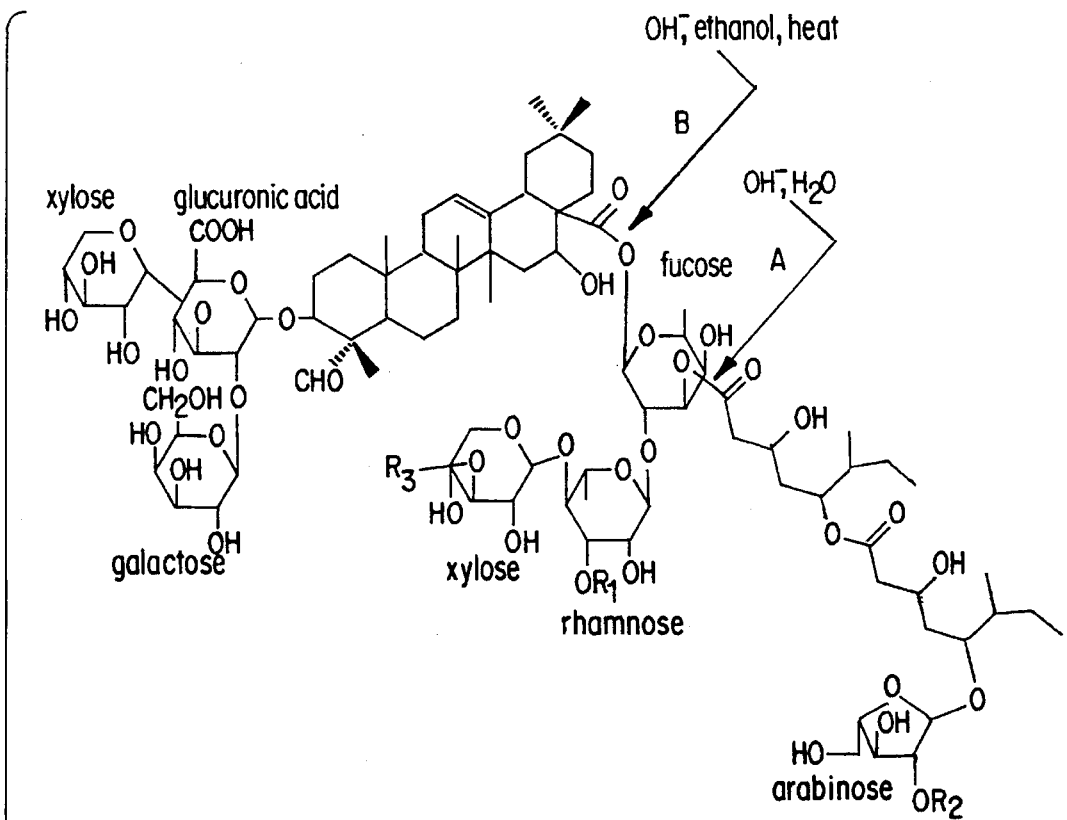
FIG. 10 shows the proposed structure of QA-17, QA-18, QA-21-V1 and QA-21-V2.

FIG. 10 shows a proposed structure and the relationship between three of these compounds. The basic structure is taken from Higuchi (*Phytochemistry* 27:1165–1168 (1988)) who determined the structure of a compound (which he designated QSIII) from *Quillaja saponaria* that matches the carbohydrate composition and molecular weight of QA-17 reported here. Variations to this structure for QA-18 and QA-21 were determined by carbohydrate composition and linkage analysis, molecular weights as determined by FAB-MS, and comparative analysis of common hydrolytic byproducts. The predominant changes in glycoside composition are in the terminal monosaccharides. QA-18 and QA-21 contain t-arabinose whereas QA-17 contains 2-arabinose. QA-17 contains t-rhamnose (not present in QA-18 and QA-21), suggesting t-rhamnose is linked to 2-arabinose in QA-17 whereas arabinose is a terminal residue in QA-18 and QA-21. In addition, QA-17 and QA-18 contain 3,4-rhamnose and t-glucose whereas QA-21 contains 4-rhamnose and no glucose. This is indicative of glucose substitution at the 3 position of 3,4-rhamnose in QA-17 and QA-18. Molecular weights, determined by fast atom bombardment mass spectroscopy, are consistent with these structures. Further support is provided by analysis of hydrolytic byproducts. Higuchi demonstrated that mild alkaline hydrolysis of QSIII resulted in cleavage at the ester bond linking the fatty acid moiety to fucose. Cleavage of QA-17 -18, and -21 at this site theoretically yields a triterpene glycoside fragment (A) that is identical for QA-17 and -18 and is more hydrophobic for QA-21 (due to absence of glucose); this is confirmed experimentally by analysis of reverse phase HPLC retention times of the fragments from these compounds. These compounds can be hydrolyzed under more severe conditions to cleave the ester bond linking fucose to the quillajic acid backbone; the limiting triterpene glycoside fragment (B) resulting from this cleavage is theoretically identical for all 3 compounds (confirmed by HPLC analysis).

All three compounds augment humoral immune responses in mice with similar dose response curves. Hence, it would appear that the terminal residues rhamnose and glucose are not critical to this facet of the adjuvant function of these compounds.

Characterization of Saponins as Detergents

The critical micellar concentration of adjuvants QA-7, QA-17, QA-18, and QA-21 was determined by the method of DeVendittis et al. (DeVendittis et al. *Anal. Biochem.* 115:278–286 (1981)) as follows: The emission spectrum of 1-anilinonapthalene-8-sulfonic acid (ANS) in water was determined at dry weight concentrations of adjuvant ranging from 0.01 to 0.10% (w/v) to cover the range below and above the critical micellar concentration. Above the critical micellar concentration, the fluorescence yield of ANS increases and the wavelength of maximum emission decreases due to partitioning of the fluorescent dye into the micelles. Similar critical micellar concentrations were found for QA-7, QA-17, QA-18, and QA-21 in water (0.06%, 0.06%, 0.04%, and 0.03%, respectively) with slightly lower concentrations determined in phosphate buffered saline (0.07% 0.03%, 0.02%, and 0.02%, respectively).

Figure 11:
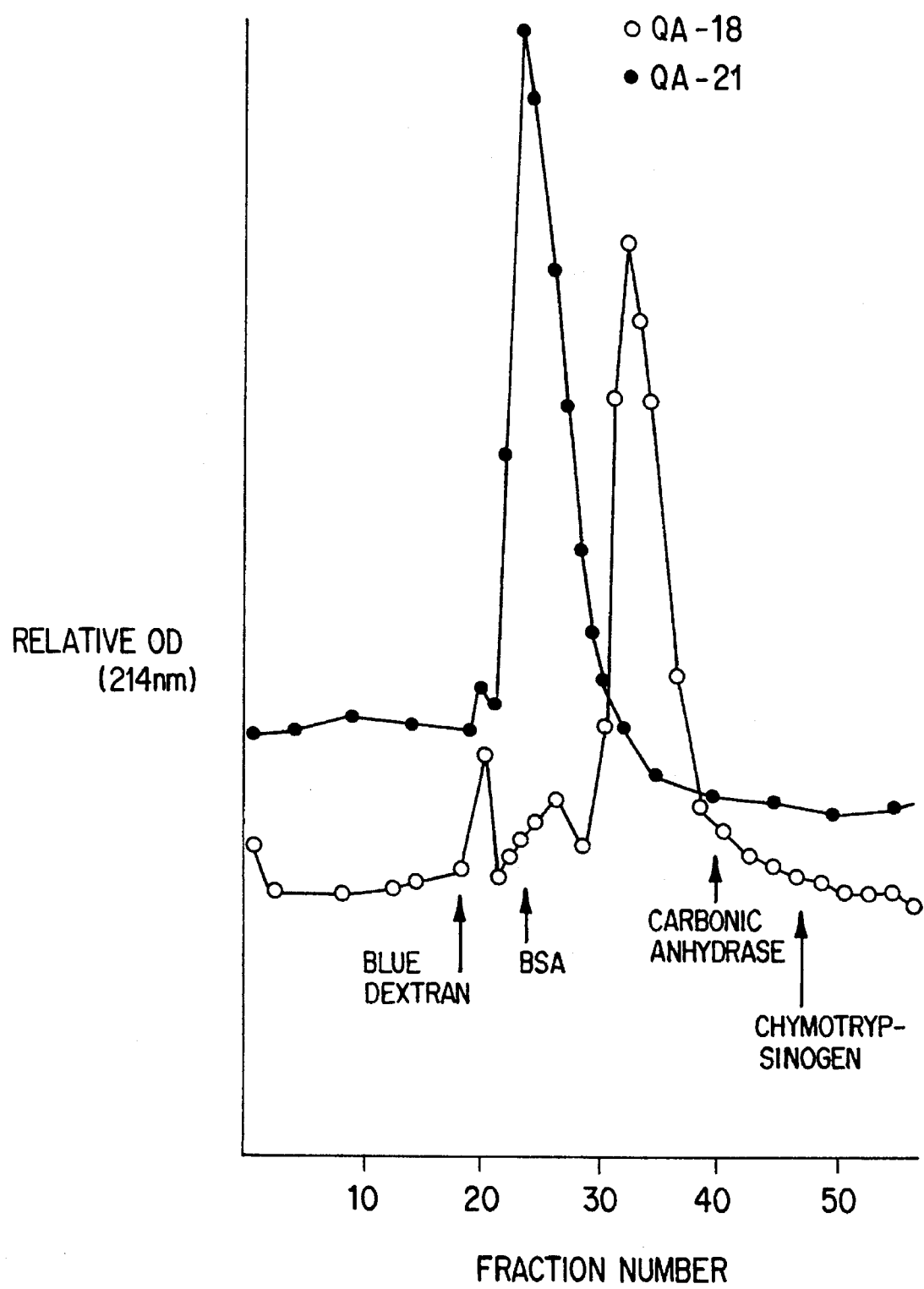
FIG. 11 shows the elution profile of pure QA-18 micelles and pure QA-21 micelles by gel filtration on BioGel P-200 in PBS equilibrated with the critical micellar concentration of the same saponin and a comparison with the elution position of standard proteins.
Figure 12:
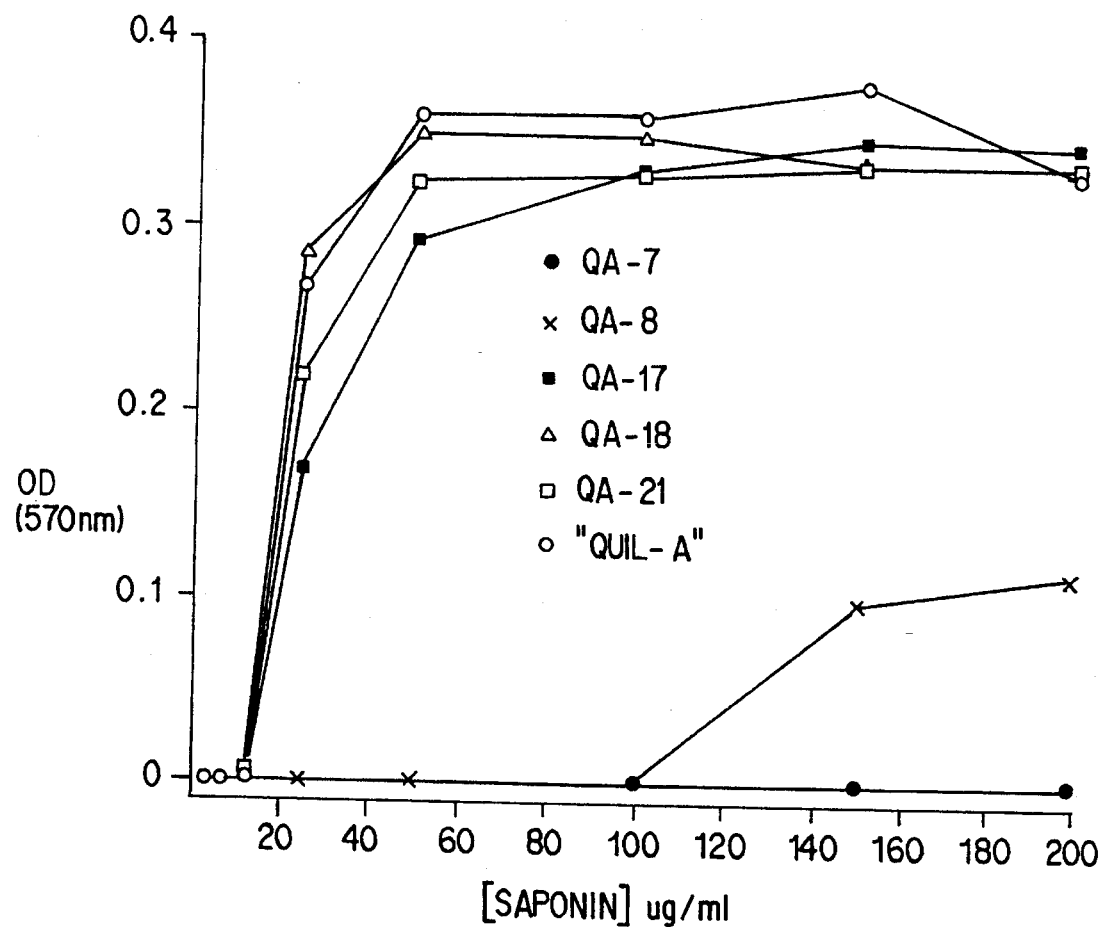
FIG. 12 shows the hemolysis of sheep red blood cells by QA-7, QA-8, QA-17, QA-18, QA-21, and Superfos "Quil-A."

FIG. 11 shows the gel filtration chromatograph for micelles formed by purified QA-18 and QA-21 (on Bio-Gel P-200 (6.6 mm ID×90 cm ht)), pre-equilibrated in a concentration of purified saponin equivalent to the critical micellar concentration of that saponin in phosphate buffered saline to prevent the monomer-micelle equilibrium from reducing the apparent radius of the micelles). QA-18 and QA-21 micelles elute with a size that is similar to that of the protein bovine serum albumin.

The hemolytic activity of the adjuvants was determined by the following method: Dilutions of adjuvants QA-7, QA-8, QA-17, QA-18, QA-21, and Superfos "Quil-A" were made on a round bottom microtiter plate (75 μl per well). Sheep red blood cells (SRBC), washed three times with PBS, were diluted to 4% with PBS. SRBC (25 μl) were added to each well and mixed with adjuvant. After incubation at room temperature 30 min, the plates were spun at 1000 rpm 5 min in a Sorvall RT6000, H-1000 rotor, to sediment unhemolyzed cells. 50 μl of the supernatant from each well was transferred to the same well of a flat bottom microtiter plate and diluted to 200 μl with $H_2O$. Absorbance was determined at 570 nm with a Dynatech microtiter plate reader. (FIG. 11) Hemolysis increased the absorbance at 570 nm due to release of hemoglobin from the lysed cells. Significant differences in hemolysis were observed between adjuvants. QA-17, QA-18, QA-21, and Superlos "Quil-A" caused partial hemolysis at concentrations as low as 25 μg/ml whereas partial hemolysis was observed with QA-8 at 150 μg/ml. No hemolysis was observed with QA-7 at the concentrations tested (200 μg/ml and less).

EXAMPLE 7

ISOLATION OF TOXIC COMPONENT QA-19

The toxic component QA-19 co-chromatographs with QA-18 on silica and is enriched in silica fractions 31–60. These fractions were pooled and flash evaporated prior to further purification. FIG. 4C shows the separation of QA-19 from QA-18 by reverse phase HPLC on Vydac $C_4$ (10 mm ID×25 cm L) using a methanol gradient. Fractions eluting with a retention time between 50–52 minutes were identified as QA-19 by reverse phase TLC and analytical HPLC and pooled for further characterization. QA-19 could be further separated into two peaks by repurification in a shallower methanol gradient, with the peak with shorter retention time designated QA-19a and the peak with longer retention time designated QA-19b. Carbohydrate analysis of peak QA-19a which is more toxic in mice than QA-19b, shows a carbohydrate composition which is similar to that of the other saponins (Table 3).

EXAMPLE 8

ISOLATION OF ALKALINE HYDROLYSIS PRODUCT

Treatment of QA-18 by brief alkaline hydrolysis yielded one major carbohydrate-containing alkaline hydrolysis product (designated QA-18 H; shown as Fragment A in FIG. 10). Purified QA-18 H was prepared from QA-18 and isolated in the following manner:

One ml QA-18 (5 mg/ml) was incubated with 25 μl 1N NaOH for 15 minutes at room temperature. The reaction was stopped with the addition of 100 μl 1N acetic acid. Using these hydrolysis conditions, QA-18 was completely converted to a major hydrolysis product (QA-18 H) eluting in a peak with retention time of 8.0 min compared to 66.8 min for unhydrolyzed QA-18, indicating the increased hydrophilicity of QA-18 H. (Chromatography on Vydac $C_4$ (4.6 mm ID×25 cm L) in 0.1% trifluoroacetic acid in 55/45 methanol/water v/v) and eluted in a gradient to 64/36 methanol/water (v/v) over 180 minutes, flow rate of 1 ml/minute). The peak containing pure QA-18H (retention time 8.0 min) was pooled for further characterization. The hydrolysis product of QA-21, designated QA-21H, was prepared and purified in the same manner. QA-21H had a retention time of 9.3 minutes compared to 80.4 minutes for unhydrolyzed QA-21. These hydrolysis products were shown by retention time on HPLC and by reverse phase thin layer chromatography to be identical to the major hydrolysis products generated using the method of Higuchi et al., *Phytochemistry* 26:229 (1987) using mild alkaline hydrolysis in $NH_4HCO_3$ (Table 5). In addition, these products, QA-18H and QA-21H, were shown to be the major breakdown products from hydrolysis of "Quil-A", a crude saponin mixture containing QA-7, QA-17, QA-18, and QA-21 as well as other saponins, indicating that the hydrolysis products QA-21H and QA-18H are the same hydrolysis products isolated by Higuchi et al., supra, for structural characterization. QA-18H and QA-21H were saved for further characterization of adjuvant activity.

TABLE 5

| Retention Time of Major Alkaline Hydrolysis Products | |
|---|---|
| QA-17 H | 8.0[a] |
| QA-18 H | 8.0[a] |
|  | 8.2[b] |
| QA-21 H | 9.3[a] |
|  | 9.5[b] |
| Hydrolyzed - "Quil-A" | 8.2[a], 9.3[a] |

[a]Cambridge Biotech hydrolysis conditions: 5 mg/ml saponin, pH 13, reaction time = 15 minutes at room temperature
[b]Higuchi et al. hydrolysis conditions: 5 mg/ml saponin, 6% $NH_4HCO_3$, methanol/$H_2O$ (1/1, v/v), reaction time = 60 minutes at 100° C.
HPLC Conditions: Vydac C4, 5 μm particle size, 300 Å pore size, .46 × 25 cm
Solvent A = 0.1% trifluoroacetic acid in water
Solvent B - 0.1% trifluoroacetic acid in methanol
Gradient = 55–64% B/180 minutes
Flow rate - 1 ml/min

EXAMPLE 9

TESTING FOR ADJUVANT EFFECT USING BSA AS ANTIGEN

Briefly, adjuvant effect is assessed by increase in antigen-specific antibody titers due to addition of potential adjuvant in the immunization formulation. Increased titers result from increased antibody concentrations and/or increased antigen/antibody affinity. Adjuvant effects of saponins have previously been measured by increase in titer of neutralizing antibodies to foot-and-mouth disease vaccines in guinea pigs (Dalsgaard, K., *Archiv. fur die gesamte Virusforschung* 44:243–254 (1974)), increase in titer of precipitating antibodies to BSA (as measured by radial immunodiffusion) in guinea pigs vaccinated with BSA/saponin mixtures (Dalsgaard, K. *Acta Veterinaria Scandinavica* 69:1–40 (1978)), as well as by the increase in titer of anti-keyhole limpet hemocyanin (KLH) antibody (measured by ELISA) in mice immunized with KLH/saponin (Scott et al. *Int. Archs. Allergy Appl. Immun.* 77:409–412 (1985)).

Figures 13A, 13B, 13C:
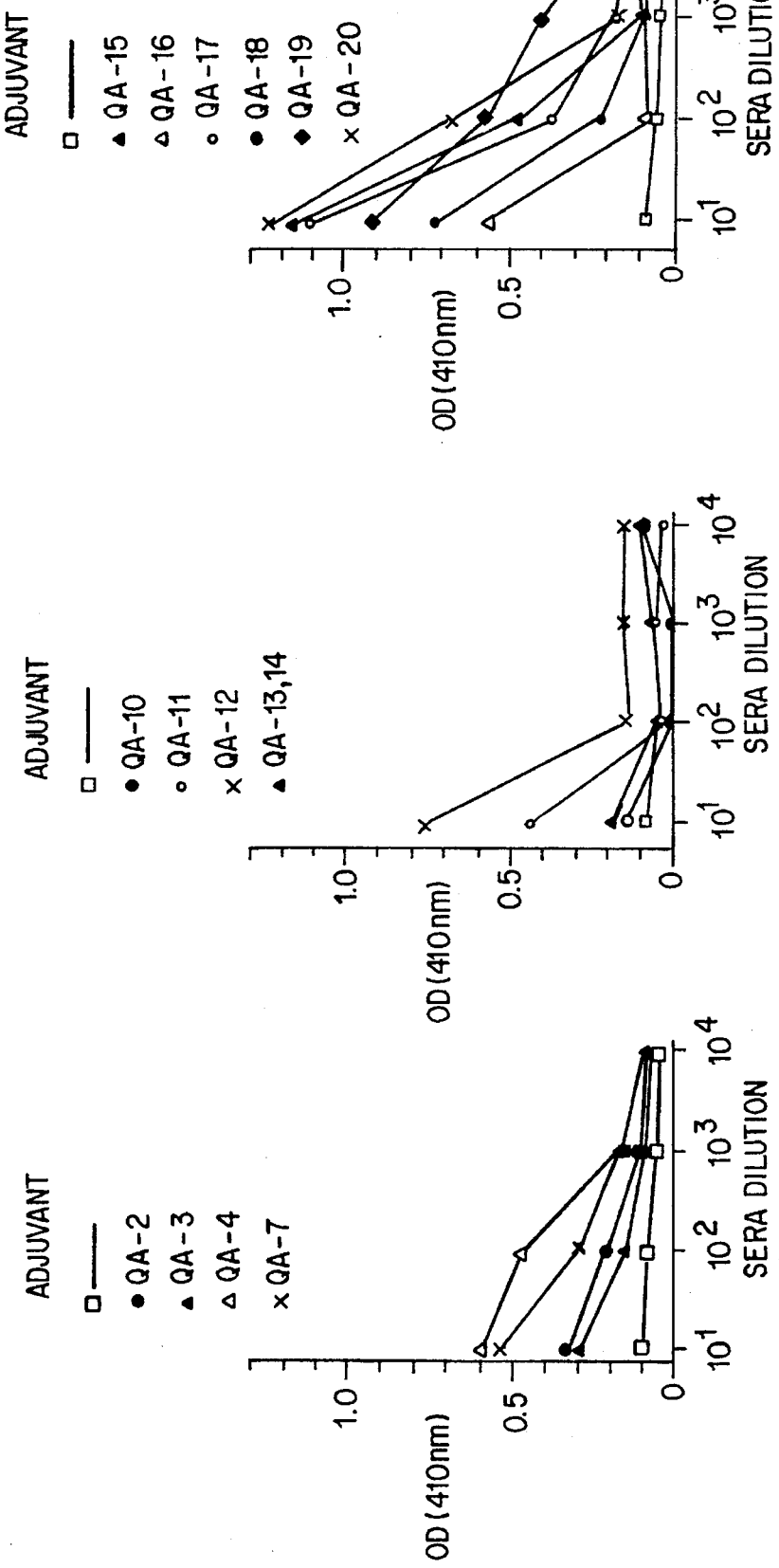
FIGS. 13A–13C show the typical endpoint titers for immunization with BSA antigen in the presence of HPLC-purified fractions of bark extract. Absorbance due to antigen-specific antibody binding was plotted as a function of the logarithm of the sera dilution.

Assessment of adjuvant effect in this study was determined by increase in anti-BSA antibody following immunization with BSA/saponin compared with immunization with BSA in the absence of saponin. The adjuvant activity in the purified fraction was measured as follows: CD-1 mice (8–10 weeks old) were immunized intradermally with the following formulation: 10 μg BSA (Sigma 7030, fatty acid free) and Quillaja adjuvant (at doses ranging from 1.5–45 μg carbohydrate as measured by anthrone) in 200 μl PBS. Sera was harvested two weeks post immunization. Anti-BSA antibody was determined by ELISA: Inmulon II plates were coated overnight at 4° C. with 100 μl fatty acid free BSA (10 μg/ml in PBS) in rows, A, C, E, and G. Plates were washed twice with PBS. Nonspecific binding was prevented by incubating for 1.5 h at 37° C. with 100 μl diluent (2% Casein acid hydrolysate (Oxoid, w/v) in PBS) per well in all wells. Plates were washed four times with 0.05% Tween 20 in distilled water. Sera at dilutions of 10, $10^2$, $10^3$, and $10^4$ were incubated in rows A+B, C+D, E+F, and G+H, respectively (100 μl/well) for 1 h at room temperature. Plates were washed as described above. Boehringer-Mannheim horse radish peroxidase conjugate goat anti-mouse antibody (1/5000 in 5% BSA in diluent) was incubated for 30 min at room temperature (100 μl per well, all wells). Plates were washed as described above. The extent of peroxidase reaction was determined by reaction with 2,2'-azino-bis(3-ethylbenzthiazoline)-6-sulfonate (30 minute reaction at room temperature, absorbance measured at 410 nm) or with 3,3', 5,5'-tetramethylbenzidine (10 min reaction at room temperature, absorbance measured at 450 nm). The contribution of nonspecific antibody binding to the total antibody binding was removed by subtraction of the absorbance of the antigen-negative well frown the absorbance of the antigen-positive well for each sera dilution. The absorbance due to antigen-specific binding was plotted as a function of the logarithm of the sera dilution. (FIGS. 13A–13C) Typical endpoint titers were typically at a sera dilution of 10 or less for immunization in the absence of adjuvant and were as high as $10^3$ in the presence of saponin adjuvant. Dialyzed, methanol-soluble bark extract at an adjuvant dose of 12 μg carbohydrate or greater (carbohydrate assayed by anthrone) increased titers by 2 orders of magnitude compared to BSA in PBS. A good adjuvant effect was observed at doses of "Quil-A" between 9–23 μg carbohydrate.

EXAMPLE 10

ADJUVANT TESTING OF HPLC-PURIFIED EXTRACT COMPONENTS

By the criteria described in Example 9, peaks QA-7, QA-11, QA-12, QA-15, QA-16, QA-17, QA-18, QA-19, and QA-20 have varying degrees of adjuvant effect with QA-15, QA-17, QA-18, QA-19, and QA-20 being particularly effective at a dose of 3.0 μg carbohydrate in this particular experiment. Due to the small number of mice used per immunization (2) and the natural variation in immune response between individual mice, this experiment cannot be used to quantitatively assess the relative adjuvant effect of these peaks. However, it provides a qualitative assessment of the presence of adjuvant activity. It must also be noted that the absence of apparent effect with QA-2, QA-3, QA-10, QA-13, and QA-14 does not rule out an adjuvant effect at different adjuvant doses or adjuvant/protein ratio.

Further adjuvant studies were carried out with QA-7, QA-17, and QA-18 at different protein/adjuvant ratios. In general, a good adjuvant effect was observed for QA-7, QA-17, and QA-18 when used at protein/adjuvant ratios (protein weight/carbohydrate weight) of approximately 3:1 to 9:1 (FIGS. 14A–C). QA-21 (tested in this study only at protein/carbohydrate weight of 6:1) also showed an adjuvant effect. However, it should be noted that the proper adjuvant to protein ratio for optimum immune response is a function of both the particular saponin adjuvant and the particular antigen used. Adjuvant association with antigen plays an important role in the mechanism of action of the saponin adjuvant effect. In the case of saponin binding to protein, hydrophobic interactions are the predominant factor. Hence, differences in hydrophobicity of the HPLC-purified adjuvants will affect the binding constant to hydrophobic proteins. In addition, the number of hydrophobic binding sites on the protein will also affect tile ability to associate with saponin adjuvants. Hence, it is necessary to determine the optimum adjuvant dose for each individual adjuvant and antigen. Such optimization is within the skill of the art.

HPLC-purified adjuvants were also compared with Freund's complete adjuvant and were found to result in a similar level of immune response (FIG. 14b).

EXAMPLE 11

ADJUVANT TESTING OF QA-21-V1 AND QA-21-V2

Figure 15A:
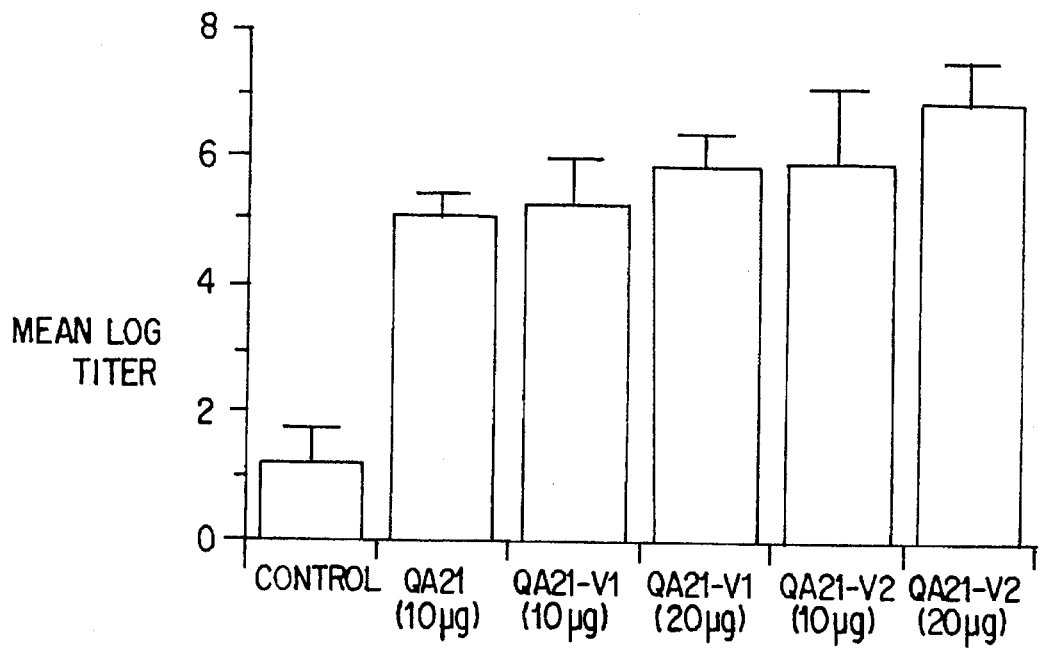
FIGS. 15A–15D show the adjuvant effect of QA-21 (mixture), QA-21-V1 and QA-21-V2 in boosting the IgG titers in subclasses IgG1 (FIG. 15A), IgG2b (FIG. 15B), and IgG2a (FIG. 15C), as well as total IgG (FIG. 15D).
Figure 15B:
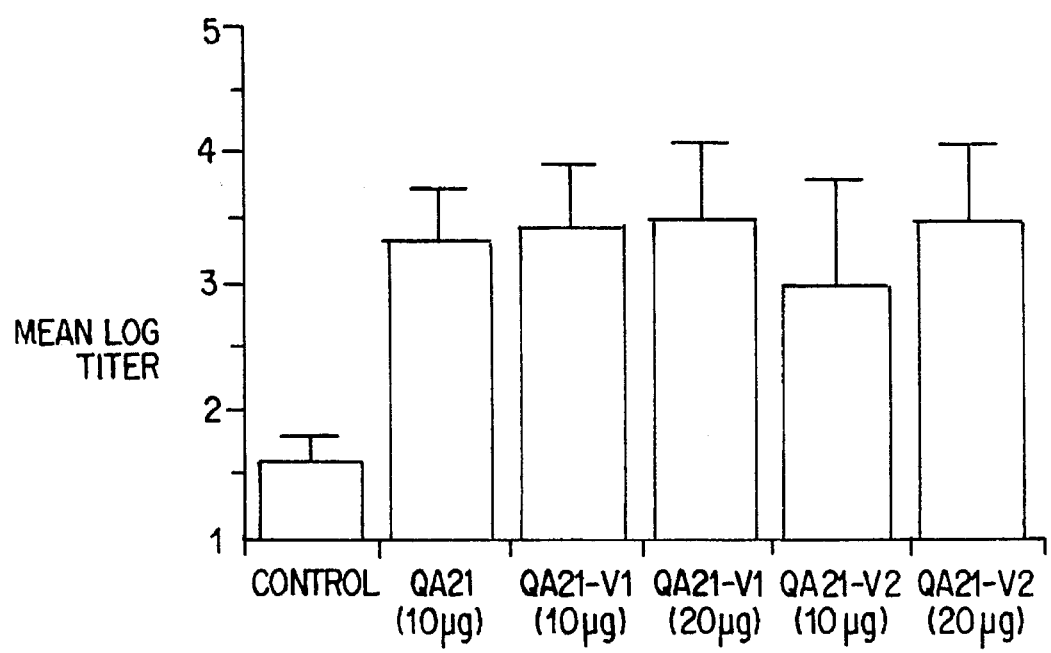
Figure 15C:
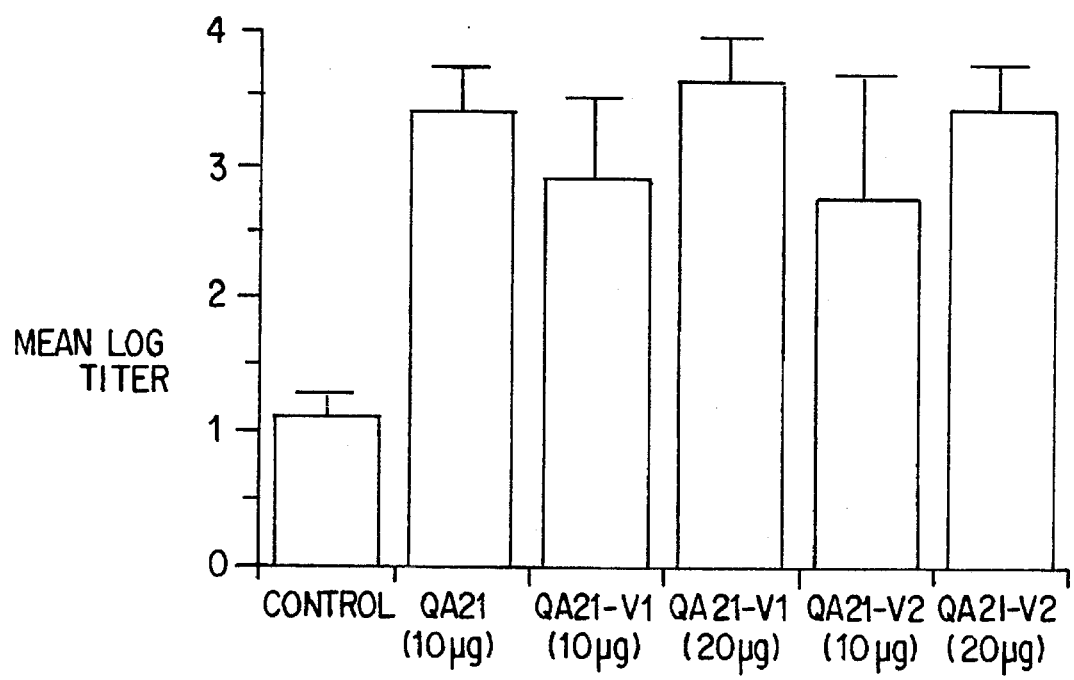
Figure 15D:
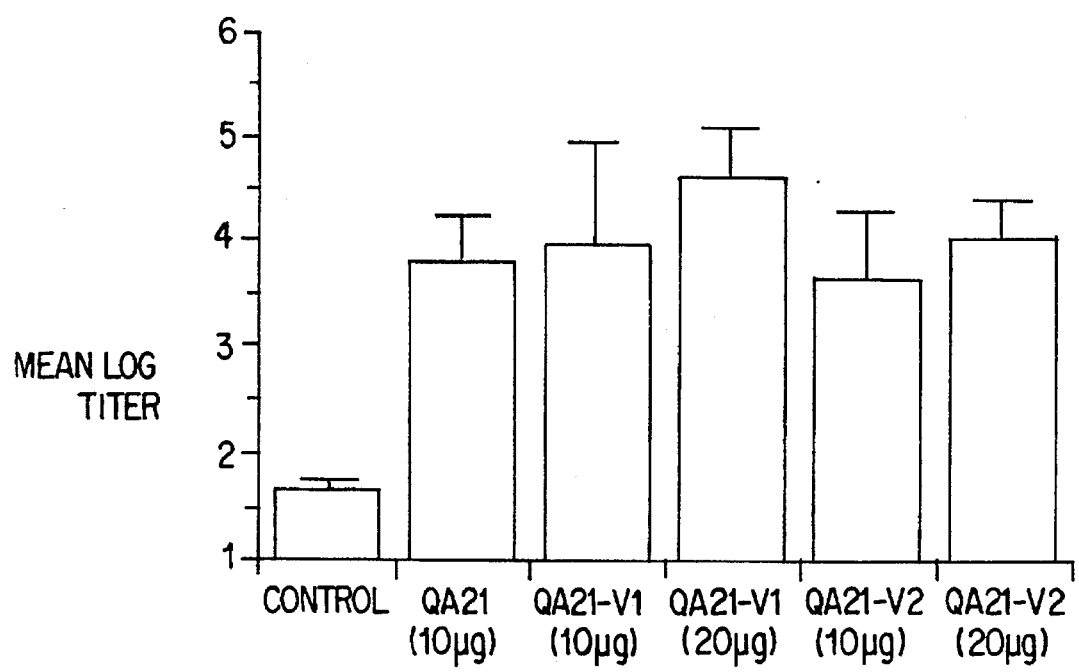

C57bl/6 mice (8 weeks of age, 5 per group) were immunized subcutaneously with 25 μg chicken egg albumin (ovalbumin) in saline with and without QA-21 (10 μg) or the individual components (at 10 and 20 μg doses). A booster immunization was given two weeks later and the serum was analyzed at a week after the booster immunization. Analysis was carried out by enzyme immunoassay of ovalbumin-specific IgG subclasses. Both QA-21-V1 and QA-21-V2 are comparable in adjuvant effect to the original QA-21 peak (containing a mixture of 3:2 QA-21-V1:QA-21-V2) for boosting the IgG subclasses IgG1 (FIG. 15A), IgG2b (FIG. 15B), and IgG2a (FIG. 15C) as well as the total IgG titer (FIG. 15D). Thus, both QA-21-VI and -V2 are adjuvants for stimulating antibody responses to the antigen ovalbumin, as is the mixture QA-21.

Figure 15E:
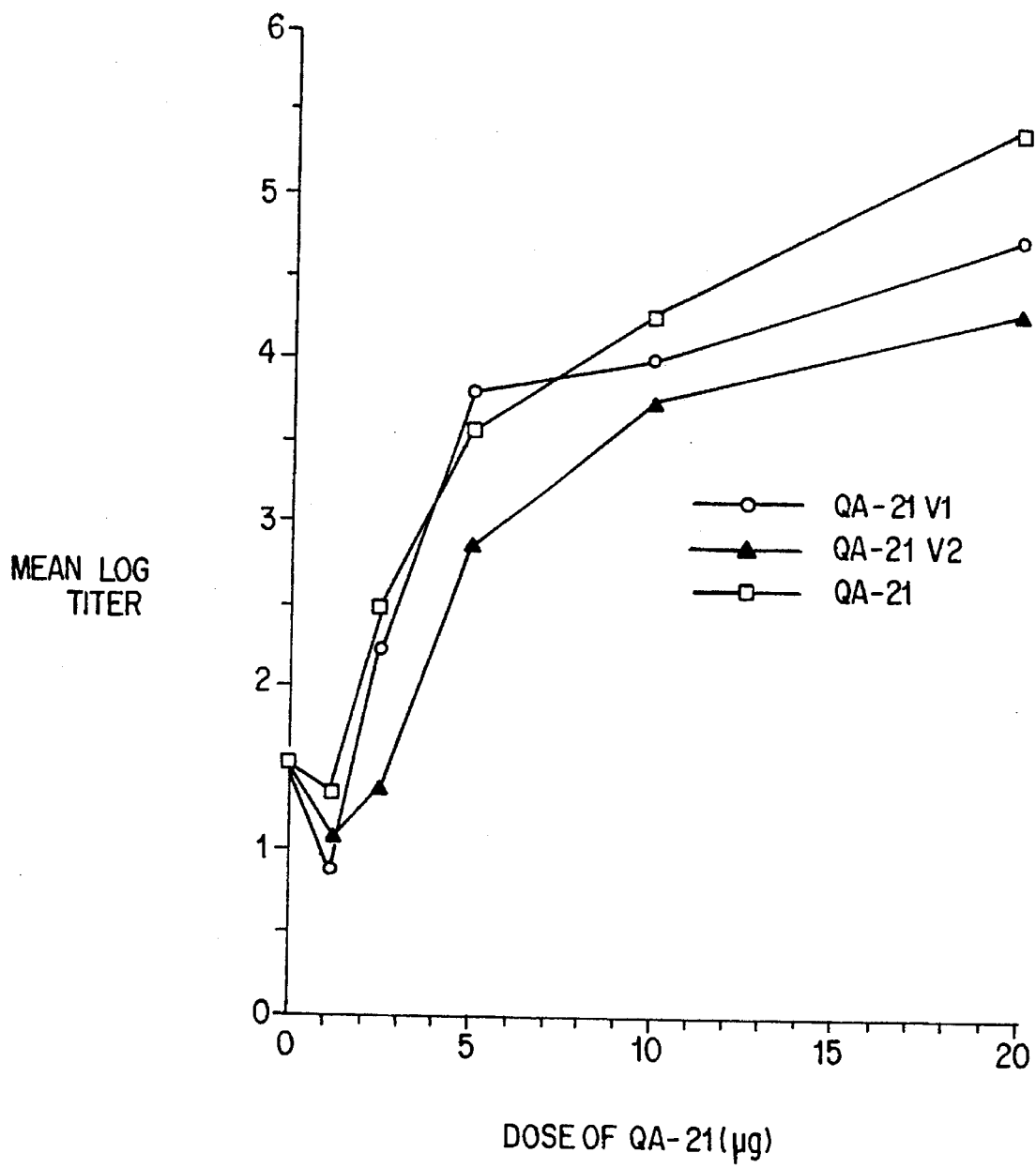
FIG. 15E shows the dose response curves for QA-21, QA-21-V1 and QA-21-V2 in boosting the total IgG titer.

The experiment was repeated with a second booster given at two weeks and the serum analyzed at three weeks, using varying amounts of saponin to produce a dose curve (FIG. 15E). Only total IgG titer was included in the curve.

EXAMPLE 12

PREPARATION OF FELV RECOMBINANT GP70R-DELTA

Inclusion Body preparation

Recombinant *E. coli* clone R16-38 was grown in LB medium supplemented with 1% glucose and 0.1% casamino acids at 32° C. to an optical density (560 nm) of 0.4–0.6. The culture was then shifted to 42° C. and incubated for an additional 2 hours. At the end of this time the cells were collected by centrifugation at 4,000 g for 30 minutes, washed with 50 mM Tris HCl, pH 7.5, and finally resuspended in 200 ml 50 mM Tris HCl to which is added 1 ml 0.1M phenyhmethylsulfonylfluoride in isopropanol (final concentration=0.5) and 0.4 ml of 5 mg/ml aprotinin (final concentration=10.0 ug/ml). The cells were lysed by enzymatic digestion with lysozyme (final concentration=0.5 mg/ml) in the presence of 0.2% Triton X-100. After stirring for 30 minutes, 2 ml $MgCl_2$ (0.5M), 5 ml DNaseI (1 mg/ml) and 1 ml 0.1M phenyhmethylsulfonylfluoride were added. After stirring for 30 additional minutes, 40 ml EDTA (0.25M, pH 7.5) and 4 ml Triton X-100 (10% w/v) were added. The preparation was centrifuged at 10,000×g for 30 minutes at 4° C., and the pellet was resuspended in 50 ml 50 mM Tris HCl, pH 7.5. The pellet was homogenized at low speed for 15 seconds. Lysozyme was added to a concentration of 0.5 mg/ml and 0.6 ml of 10% Triton X-100 were added. After stirring for 15 minutes, 10 ml of $MgCl_2$ (0.5M) and 1 ml DNase I (1 mg/ml) were added and stirring was continued for an additional 15 minutes. After adjusting the volume to 300 ml with 50 mM Tris, pH 9.0, 40 ml of 10% Triton X-100 and 51.2 ml of EDTA (0.25M, pH 7.5) were added and the final volume adjusted to 400 ml with 50 mM Tris, pH 9.0. After stirring for 30 minutes, the suspension was centrifuged at 10,000×g for 30 minutes at 4° C., and the pellet was resuspended in 400 ml 50 mM Tris HCl, pH 7.5, containing 4M urea, 50 mM EDTA, and 1% Triton X-100. After stirring for 15 minutes, the suspension was centrifuged at 10,000×g for 30 minutes at 4 ° C., and the pellet was resuspended in 400 ml 50 mM Tris HCl, pH 7.5, containing 1.0M NaCl. After stirring for 15 minutes, the suspension was centrifuged at 10,000×g for 30 minutes at 4° C., and the pellet was resuspended in 400 ml 50 mM Tris HCl, pH 7.5, containing 6M urea, and 50 mM EDTA. After stirring for 15 minutes, the suspension was centrifuged at 10,000×g for 30 minutes at 4° C. At this point the pellet of inclusion bodies was either frozen for future use or solubilized in 50 mm Tris HCl, pH 9.5, containing 6M guanidine HCl, 50 mM EDTA, and 0.5% beta-mercaptoethanol. The gp70R-delta polypeptide was then purified by either of the methods of Example 13, below.

EXAMPLE 13

PURIFICATION OF FeLV RECOMBINANT GP70R-DELTA

Procedure I

The solubilized protein of Example 12 was dialyzed against 6M urea, 50 Tris-Cl, pH 8.0, 5 EDTA, and 1 dithiothreitol (DTT). Approximately 120 mg of the protein was applied to a CM-TSK column (EM Science, 1.5 cm ID×4 cm) equilibrated with the same buffer. The protein was eluted with a linear gradient of NaCl (0–1.0M in 150 ml) in the same buffer. The fractions were collected and analyzed by electrophoresis on 10% SDS-polyacrylamide gels. Coomassie-staining was used to identify the gp70R-delta protein. Fractions 25–31, eluting at approximately 0.1M NaCl, were pooled and used for immunization.

Procedure II

In order to decrease the hydrophobicity of gp70R-delta, the sulfhydryl groups were alkylated with iodoacetamide and the lysine residues were N-acylated with citraconic anhydride. The protein prepared as in Example 8 was solubilized in 6M guanidine-HCl in 50 mM borate, pH 9.0, 0.5% beta-mercaptoethanol (v/v). Iodoacetamide is added at a molar ratio of 1:1 (iodoacetamide: total sulfhydryl groups). The alkylation was carried out in the dark for 1 hour at room temperature. The alkylation of all sulfhydryl groups (in the protein and beta-mercaptoethanol) was monitored with DTNB (Ellman's reagent) to ensure complete alkylation. The protein concentration was adjusted to 2 mg/ml.

The protein was citraconylated in the dark by the addition of citraconic anhydride (0.0022 ml per mg protein; approximately 50 molar excess over free lysines). The preparation was dialyzed several times in the dark against 50 mM borate, pH 9.0. The completion of the acylation of the protein lysine groups was determined by reaction with trinitrobenzene sulfonic acid (TNBS) which measures residual free lysine groups. TNBS (200 μl of 10 mM) was added to 200 μg alkylated, citraconylated, dialyzed gp70R-delta in 1 ml 50 mM sodium borate, pH 9.0. The mixture was incubated for 2 hours in the dark at 40° C., the reaction quenched with 0.5 ml of 1N HCl and 0.5 ml 1% SDS, and the absorbance was read at 340 nm. The concentration of TNP-lysine was determined using a molar extinction coefficient of 10,400.

The purification of the alkylated, citraconylated gp70R-delta was performed at pH 9.0 to prevent deblocking of lysine groups. Urea at a final concentration of 4M was added to the modified protein. The protein was concentrated to 3 mg/ml by ultrafiltration and applied to a Sepharose 6B-Cl column (1.5×86 cm). The gp70R-delta protein was eluted at a flow rate of 6.6 ml/hr with 4M urea, 50 mM sodium borate, pH 9.0. Fractions (5.3 ml/fraction) were collected and the gp70R-delta was determined by protein assay and SDS-polyacrylamide electrophoresis to be in fractions 13–15.

The citraconylation of gp70R-delta was reversed by dialyzing 5 ml of alkylated, citraconylated gp70R-delta (1.0 mg/ml) against 6M urea in 50 mM sodium citrate, pH 5.5 for 48 hours at room temperature. The gp70R-delta was dialyzed against 6M urea in 100 mM sodium bicarbonate, pH 8.0 and the protein concentration adjusted to 0.8 mg/ml prior to absorption to aluminum hydroxide.

Procedure III

A modification of the above purification of alkylated, citraconylated gp70R-delta was developed. Briefly, alkylated, citraconylated gp70R-delta is modified and dialyzed against 50 mM sodium borate, pH 9.0 as described above. Urea was added to a final concentration of 8.0M. The protein was concentrated by ultrafiltration with a PM-30 membrane to yield 2.5 mg protein/ml. The protein solution was applied to a Sephacryl S-400 column (1.5×90 cm) in a 50 mM sodium borate buffer, pH 9.0 containing 8M urea and eluted with the same buffer. Fractions (2.9 ml/fraction) were collected and fractions 34–37 containing gp70R delta were pooled. Twenty-one mg of the protein from these fractions were diluted to a final concentration of 4M urea with 50 mM sodium borate, pH 9.0 and applied to a DEAE-TSK column (1.5×11 cm). The protein was eluted with a linear gradient of NaCl (0–0.5M) in 50 mM sodium borate, pH 9.0 containing 4M urea. Three ml fractions were collected. Fractions 89–95 containing gp70R-delta were pooled and 15 mg of gp70R-delta was recovered.

EXAMPLE 14

IMMUNIZATION WITH ALUMINUM HYDROXIDE-ABSORBED GP70R-DELTA

Aluminum hydroxide which has been found to have an adjuvant effect for many proteins and is commonly used in vaccines was used as a carrier for gp70R-delta. gp70R-delta prepared by procedure I of Example 13 above absorbs tightly to 10% aluminum hydroxide in the presence of 50 mM Tris-Cl, pH 8.0 containing 6M urea. Approximately 3 μg gp70R-delta were absorbed per 100 μg aluminum hydroxide. The gp70R-delta absorbed to the aluminum hydroxide was washed with phosphate buffered saline (PBS), resuspended in PBS and used for immunization of animals.

CD-1 mice (8–10 weeks old) were immunized intradermally with gp70R-delta absorbed to Al(OH)$_3$ in a total volume of 200 μl PBS in the presence and absence of HPLC-purified saponins QA-17 or QA-18 or a mixture of QA-17 and QA-18. Twenty to twenty-five μg of gp70R-delta were injected per dose. HPLC-purified saponins QA-17 or QA-18 or a mixture of QA-17 and QA-18 were used at a dry weight dose of 10 μg. Two mice were injected for each formulation. Mice were given a booster injection of gp70R-delta/aluminum hydroxide six weeks after the initial injection. Mouse sera was analyzed for reactivity to FEA, a FeLV subgroup A, at 2, 4, and 8 weeks post-immunization by an ELISA immunoassay. Four weeks following immunization, an anti-FeLV response elicited by the recombinant gp70-delta was observed. HPLC-purified saponin adjuvants QA-17 and QA-18 boost this response. The response was two orders of magnitude greater at four weeks postimmunization in the presence of QA-17 compared to immunization in the absence of saponin adjuvant. The results of this experiment are shown in FIGS. 16A–16C.

Anti-FEA antibody was assayed by an ELISA assay. FEA virus (10 μg/ml in PBS) was absorbed to Immulon II plates overnight at 4° C. (100 μl/well). The plates were washed with PBS and nonspecific antibody binding was blocked by incubation for 1 hour with 10% normal goat serum in PBS (100 μl/well) at room temperature. Plates were then washed with 0.05% Tween-20 in distilled water. Sera was diluted in 10% normal goat serum in PBS and incubated for 1 hour at room temperature on the plate at serum dilutions of 10, $10^2$, $10^3$, and $10^4$ (100 μl/well). After washing the plates with 0.05% Tween-20 in distilled water, they were incubated for 30 minutes at room temperature with 100 μl/well of peroxidase-conjugated goat anti-mouse IgG (Boehringer-Mannheim) diluted 1/5000 in PBS. After washing the plates with 0.05% Tween-20 in distilled water, the amount of IgG-binding was determined by peroxidase reaction with 3,3',5,5'-tetramethylbenzidine from the absorbance at 450 nm determined on a Dynatech microtiter plate reader.

EXAMPLE 15

IMMUNIZATION WITH ALUMINUM HYDROXIDE-ABSORBED ALKYLATED GP70R-DELTA

CD-1 mice (8–10 weeks old) were immunized intradermally with 15 μg/dose of alkylated gp70R-delta purified by procedure II of Example 13 (absorbed to aluminum hydroxide as described in Example 14) in 200 ul PBS. HPLC-purified adjuvants QA-7, QA-17, QA-18 and mixtures of the three adjuvants were used at a dry weight dose of 10 μg. Three mice were injected for each formulation. Mouse sera was analyzed by ELISA at 2 and 4 weeks post-immunization for reactivity to FEA as described in Example 14. As with immunization with unmodified gp70R-delta shown in Example 12, immunization with alkylated gp70R-delta elicits an antiFeLV viral response by four weeks post-immunization. HPLC-purified adjuvants QA-7, QA-17, QA-18 all increase the immune response as compared to immunization in the absence of the saponin adjuvants. QA-17 and mixtures of QA-17 and QA-18 induced the highest response, inducing endpoint titers almost two orders of magnitude greater than immunization in the absence of saponin adjuvants. The results of these experiments are summarized on FIGS. 17A–17B.

EXAMPLE 16

TOXICITY OF QA-7, QA-17, QA-18, QA-19, QA-21, "QUIL-A"

With crude Quillaja saponins, a major symptom of toxicity in mice appears as necrosis of the liver. Purified saponins were injected into mice to determine effects on the liver. Mice were injected intradermally with 150 µg each QA-7, QA-17, QA-18, QA-21 and "Quil-A", the crude saponin extract used as the raw material for the purification of the other components. Animals injected with QA-7, QA-17, and QA-21 appeared mildly ill initially but appeared to recover fully within a few hours after injection. "Quil-A" caused severe symptoms which continued for 48 hours. All mice were sacrificed at 48 hours for post-mortem examination of the liver. "Quil-A" caused severe damage of the liver with multifocal areas of acute necrosis evident. QA-7, QA-17, and QA-21 did not seem to significantly affect the liver. QA-17 was also tested in kittens with subcutaneous injection of 100 µg each at 8 and 10 weeks, with no toxicity observed clinically or in the blood chemistry. In contrast, "Quil-A" induced a pyrogenic response which persisted for several hours in kittens. Hence, the purified saponins appear to be less toxic than "Quil-A" in both mice and kittens indicating that the purification process separates these saponins from one or more toxic components present in a crude Quillaja extract. One such toxic component has tentatively been identified as QA-19; dosages of 50 µg or greater were lethal in mice within a few days of injection. Further purification of QA-19 indicated that it could be separated into two peaks, QA-19a and QA-19b. QA-19a was lethal in mice at doses of 100 µg or greater whereas QA-19b was apparently nonlethal up to dose of 150 µg; hence, a synergistic effect to produce increased toxicity in the mixture of QA-19a and QA-19b cannot be ruled out. New data also shows that QA-18 is also toxic (not shown). Preliminary screening of other minor peaks isolated from "Quil-A" indicates that other fractions may also be toxic. Hence, the purification protocols allow the separation of adjuvant-active saponins from similar but distinct compounds which are more toxic or which cochromatograph with toxic contaminants.

EXAMPLE 17

INFLUENCE OF STRUCTURAL MODIFICATIONS ON ADJUVANT ACTIVITY

Modification of the saponins was carried out to determine effect on adjuvant activity. QA-18 was treated with periodate oxidation to cleave between vicinal hydroxyl groups in t-galactose and t-apiose to form dialdehydes, to assess effect of destruction of these monosaccharides on adjuvant activity.

Periodate oxidation of QA-18 caused a reduction in antibody titers of 5 fold compared to unmodified QA-18. Residual activity may be due to the low proportion (approximately 10%) of unmodified QA-18 in this material, prepared under relatively mild oxidation conditions. Hence, either galactose or apiose (or both), which are residues common to all adjuvant-active compounds from *Quillaja saponaria*, may be essential for adjuvant effect.

Figure 18:
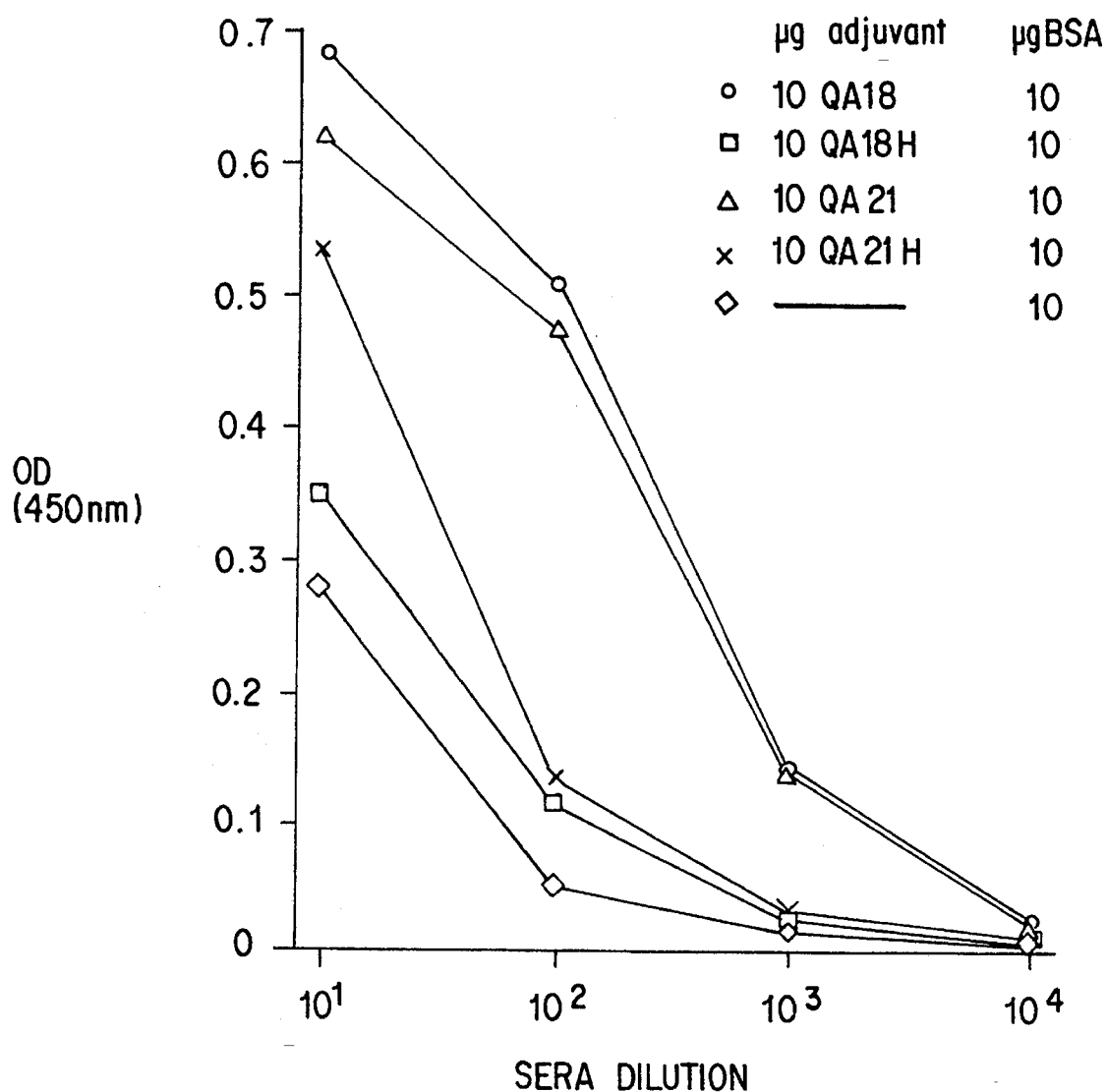
FIG. 18 shows a comparison of the adjuvant effects of QA-18, QA-18H, 0A-21, and QA-21H on immunization with the antigen BSA.

QA-18H (fragment A of QA-18; FIG. 10) and QA-21H (fragment A of QA-21; FIG. 10), prepared as described in Example 8, were tested for adjuvant effect with BSA in direct comparison with the unhydrolyzed original products QA-18 and QA-21 prepared as described in Examples 3 and 4. QA-18 and QA-21 increase the humoral immune response to BSA in mice by at least an order of magnitude by two weeks post-immunization. However, the hydrolysis products QA-18H and QA-21H at the same weight dosage do not increase the response significantly (FIG. 18). Hence, optimal adjuvant effect is observed with the intact saponins; the essential structure required for adjuvant activity is lost or altered when QA-18 and QA-21 are hydrolyzed to QA-18H and QA-21H, respectively.

Thus, removal of the fatty acid and arabinose reduces adjuvant activity substantially. However, it is unclear whether this is due to a requirement for this specific structure in receptor binding or due to the considerable increase in hydrophilicity of fragment A compared to the intact moiety, a change which could substantially affect hydrophobic interactions of QA-18 or QA-21 with cellular membranes or with antigen. This reduced hydrophobicity may also alter induction of CMI, currently being tested.

TABLE 6

| Adjuvant | Antigen-specific IgG Titers |
|---|---|
| PBS[a] | 1000 |
| Periodate Oxidized QA-18 (10 ug)[a] | 10000 |
| QA-18 (10 ug)[a] | 50000 |

[a]CD-1 mice (5/group) were immunized intradermally with 10 ug BSA and the indicated adjuvant on days 1 and 14. IgG titers were determined by EIA on day 21.

EXAMPLE 18

CONJUGATION OF SAPONIN QA-21 TO LYSOZYME

Lysozyme, a poorly immunogenic, very hydrophilic protein was selected for conjugation to the saponin QA-21. The glucuronic acid residue of saponin QA-21 was activated with dicyclohexylcarbodiimide (DCC) and sulfo-N-hydroxysuccinimide (NHS) and coupled to lysozyme as follows.

The following solutions in DMSO were prepared:

| Solution | Reactant | DMSO |
|---|---|---|
| A | QA-21 (10 mg) | 800 µl |
| B | DCC (51.5 mg) | 500 µl |
| C | NHS (58.0) | 1 ml |

Solution A was combined with 100 µl of solution C and 50 µl of solution B was added. After 15 minutes, 90 minutes and 260 minutes, the reaction was monitored by HPLC (detector set at 280 nm). After 320 minutes, another 50 µl of solution B was added and the reaction continued to give a solution of the NHS ester of QA-21.

A solution of lysozyme (72 mg, MW=14,400 g/mol) in a 0.1M sodium phosphate buffer (5 ml, pH=7) was prepared. The lysozyme solution should be fairly concentrated to limit hydrolysis of the activated ester. The crude NHS ester (approximately 5 µmol) was then added to the lysozyme solution (5 µmol) in 200 µl aliquots. The solution became cloudy after the addition of the first aliquot. The reaction was monitored by HPLC after 80 and 135 minutes. The reaction mixture was then filtered, dialyzed against water and freeze dried to give the crude lysozyme-QA-21 conjugate.

The freeze dried powder was then dissolved in about 1 ml of 10 mM sodium phosphate buffer (pH 7) and the solution filtered to give about 800 μl. Purification was accomplished by injecting about 300 μl on a semiprep C4 column using a gradient elution (10% to 80% buffer B over 60 minutes; buffer A=0.15% trifluoroacetic acid in water, buffer B =0.15% trifluoroacetic acid in acetonitrile). Fractions (2 ml) were collected after 22 minutes Fractions 11–17 were pooled, dried under nitrogen, and freeze dried. This procedure was then repeated with 400 μl of the crude lysozyme-QA-21 conjugate.

Figure 19:
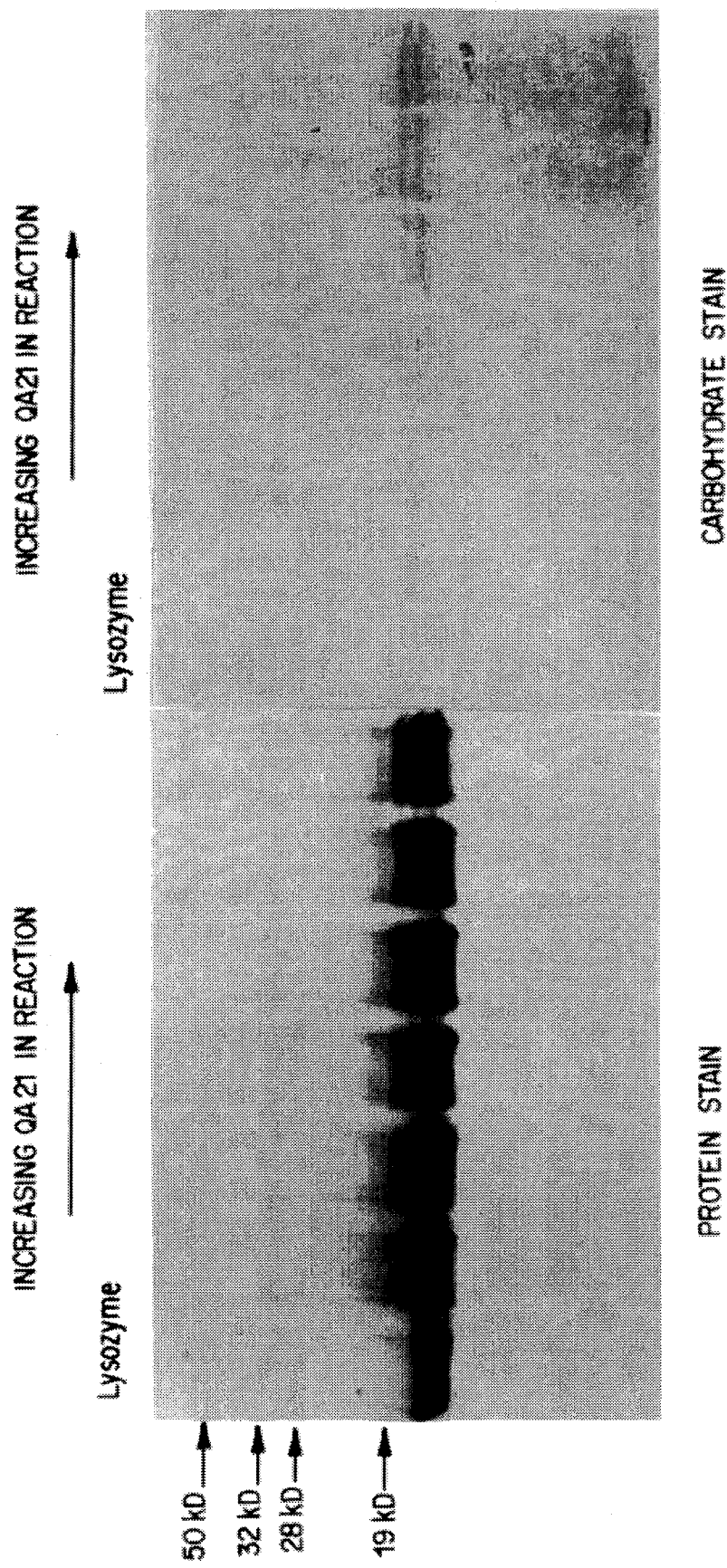
FIG. 19 shows an SDS-polyacrylamide gel electrophoresis of the reaction of lysozyme with QA-21.

The lysozyme-QA-21 conjugate showed an increase in molecular weight by SDS-polyacrylamide gel electrophoresis which corresponds to a 1:1 molar ratio of lysozyme and QA-21. The conjugate also showed a positive response to a carbohydrate stain PAS due to the addition of the carbohydrate QA-21 to the lysozyme. An example of a conjugation reaction in which increasing amounts of the active ester of QA-21 is added to lysozyme is shown in FIG. 19.

EXAMPLE 19

IMMUNIZATION OF MICE WITH QA-21-LYSOZYME CONJUGATE

The QA-21-lysozyme from Example 18 conjugate was used to immunize mice (C57bl/6), with and without added QA-21 as adjuvant. Ten nice (9 weeks of age at the beginning of the immunization) were immunized per group. Immunizations were made intradermally at day 0 and day 14 with a total volume of 0.2 ml (PBS buffer, pH 7). The vaccines contained the following dosages of antigen and adjuvant:

| Group | Lysozyme | Conjugate | QA-21 |
|---|---|---|---|
| 1 | 10 μg | — | — |
| 2 | 10 μg | — | 1.6 μg |
| 3 | — | 10 μg lysozyme/ 1.6 μg QA-21 | — |
| 4 | 10 μg | — | 10 μg |
| 5 | — | 10 μg lysozyme/ 1.6 μg QS21 | 10 μg |

The mice were bled on day 21 and the anti-lysozyme IgG titers were determined. Microtitre plates (in the alternative, Co-bind® plates from Micromembranes may be used) were incubated at 4° C. overnight with 10 μg/ml of lysozyme in about 100 μl of PBS. The plates were then washed two times with PBS and blocked for one hour with 150 μl/well of 10% normal goat serum at room temperature. The plates were then washed two times with 0.05% Tween-20 in water.

The mice sera were incubated with the lysozyme coated plates as follows. The individual serum samples (10μl) diluted with 10% normal goat serum in PBS to make 100 μl, as well as serial dilutions thereof (1:10) were added to the wells and incubated for 1 hour at room temperature. The wells were then washed four times with 0.05% Tween-20. The wells were then incubated with anti-mouse IgG linked to horse radish peroxidase (BioRad)in 100 μl of diluent (10% normal goat serum in PBS) for two hours at room temperature, washed four times with 0.05% Tween-20, and two times with water. The conjugate was then detected by tetramethylbenzidine substrate (Bos, E.S. et al., *J. Immunoassay* 2:187 (1981)). After incubation, the $OD_{450}$ was read.

Figure 20:
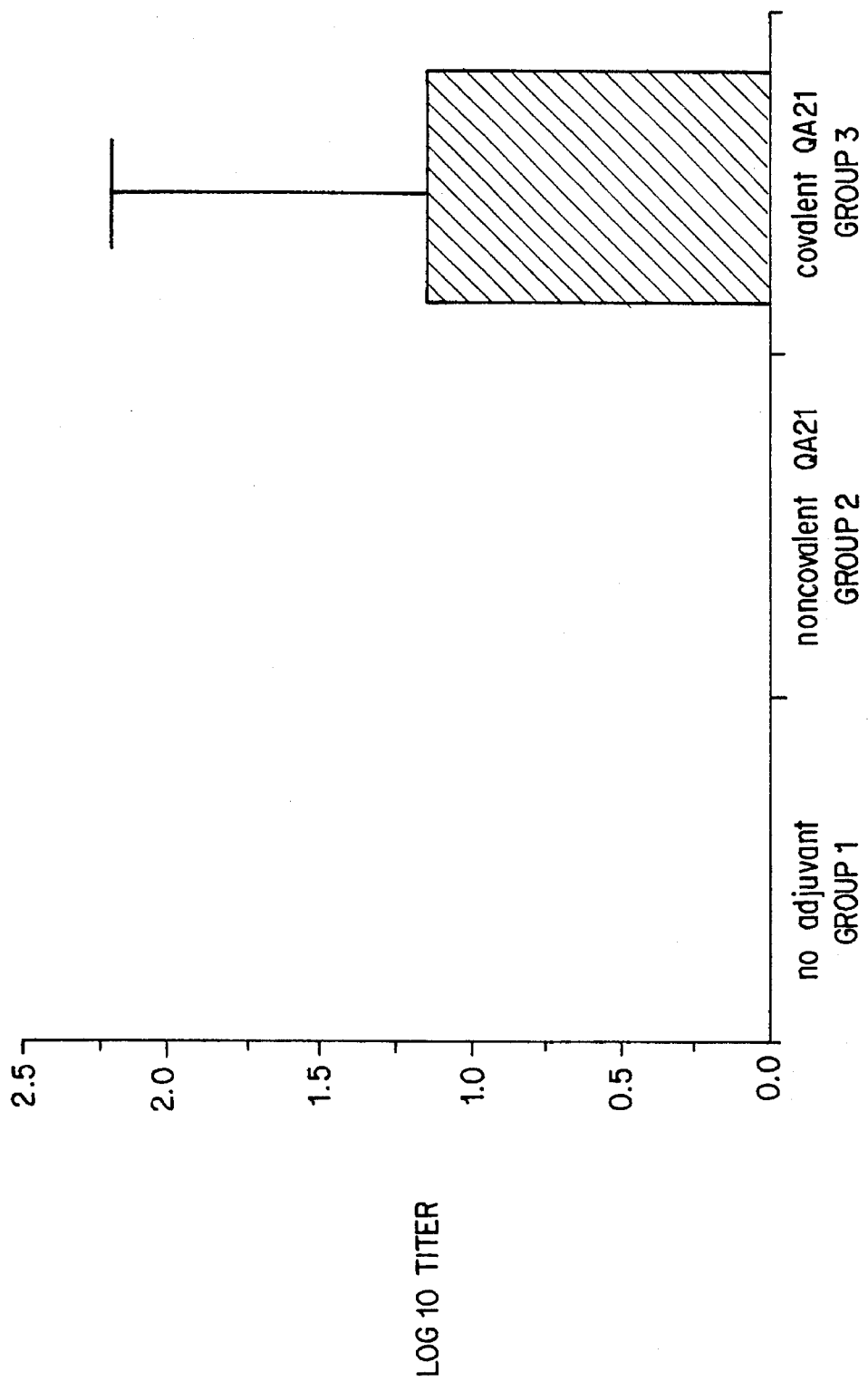
FIG. 20 shows the total IgG titers of mice immunized with lysozyme (10 μg) only and without an adjuvant; with lysozyme (10 μg) and free (noncovalent) QA-21 (1.6 μg, 1:1 molar ratio); and with QA-21-lysozyme conjugate (11.6 μg, 1:1 molar ratio).
Figure 21:
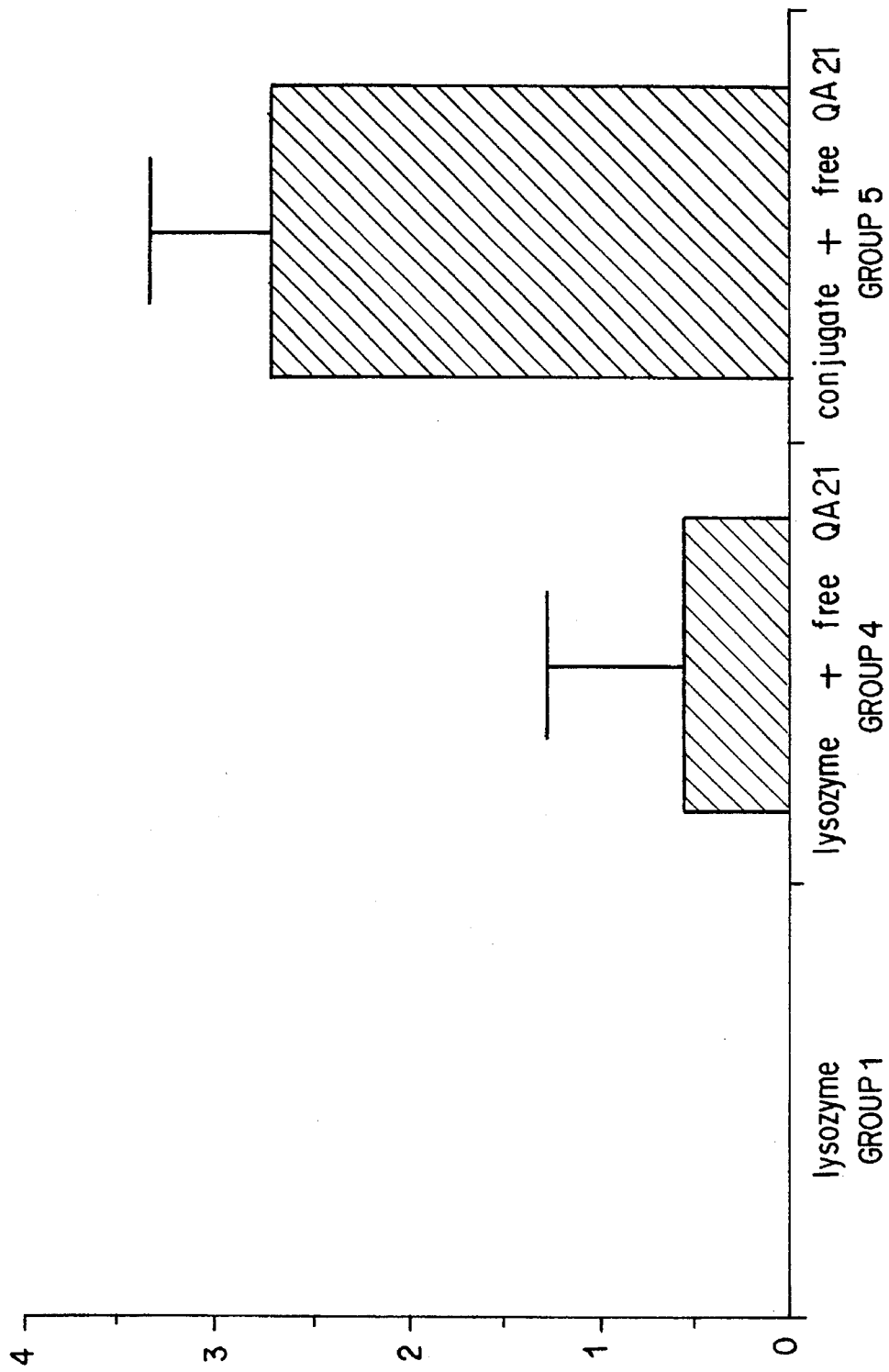
FIG. 21 shows the total IgG titers of mice immunized with lysozyme (10 μg) only; lysozyme (10 μg) and free QA-21 (10 μg); and QA-21-lysozyme conjugate (11.6 μg) and free QA-21 (10 μg).

The total anti-lysozyme IgG titers for each group of the immunized mice appear in FIGS. 20 and 21. FIG. 20 shows the anti-lysozyme titers for mice injected with lysozyme only and without an adjuvant (group 1); with lysozyme and free (noncovalent) QA-21 (group 2); and with QA-21-lysozyme conjugate (group 3). FIG. 21 compares the anti-lysozyme titers of mice injected with lysozyme only; lysozyme and free QA-21 (group 4); and free QA-21 and QA-21-lysozyme conjugate (group 5).

As can be seen in FIGS. 19–21, lysozyme is poorly immunogenic when administered alone or with QA-21 as an adjuvant. However, the mice receiving the lysozyme-QA-21 conjugate had a higher antibody titer than either of the groups receiving free QA-21. Unexpectedly, when the lysozyme-QA-21 conjugate was coadministered with free QA-21 as an adjuvant, a significant increase in antibody titer was observed. While Applicants do not wish to be bound by any particular theory, it appears that the lysozyme-QA-21 conjugate may provide a binding site for the free QA-21 which serves to increase the immunogenic response.

Next, the anti-lysozyme antibodies produced by each group of mice were isotyped. Microtitre plates were incubated at 4° C. overnight with 10 μg/ml of lysozyme in about 100 μl of PBS. The plates were then washed two times with PBS and blocked for one hour with 150 μl/well of 10% normal goat serum in PBS at room temperature. The plates were then washed two times with 0.05% Tween-20 in water.

The mice sera were incubated with the lysozyme coated plates as follows. The serum samples were tested in separate lanes for IgG1, IgG2B, IgG2A, IgM and IgG3. The individual serum samples (10 μl) were diluted with 10% normal goat serum in PBS to make 100 μl, and serial dilutions thereof (1:10) were added to the wells and incubated for 1 hour at room temperature. The wells were then washed four times with 0.05% Tween-20. The wells were then incubated with goat anti-mouse IgG1, IgG2B, IgG2A, IgM or IgG3, each linked to alkaline phosphatase (Southern Biotechnology), in 100 μl of diluent (10% normal goat serum in PBS) for two hours at room temperature, washed four times with 0.05% Tween-20, and two times with water. The conjugates were then detected by adding 100 μl per well of 1 mg/ml p-nitrophenylphosphate in 0.1M borate, pH 9.0. After incubation for 6 and 24 hours at room temperature, tile $OD_{410}$ was read.

Figure 22:
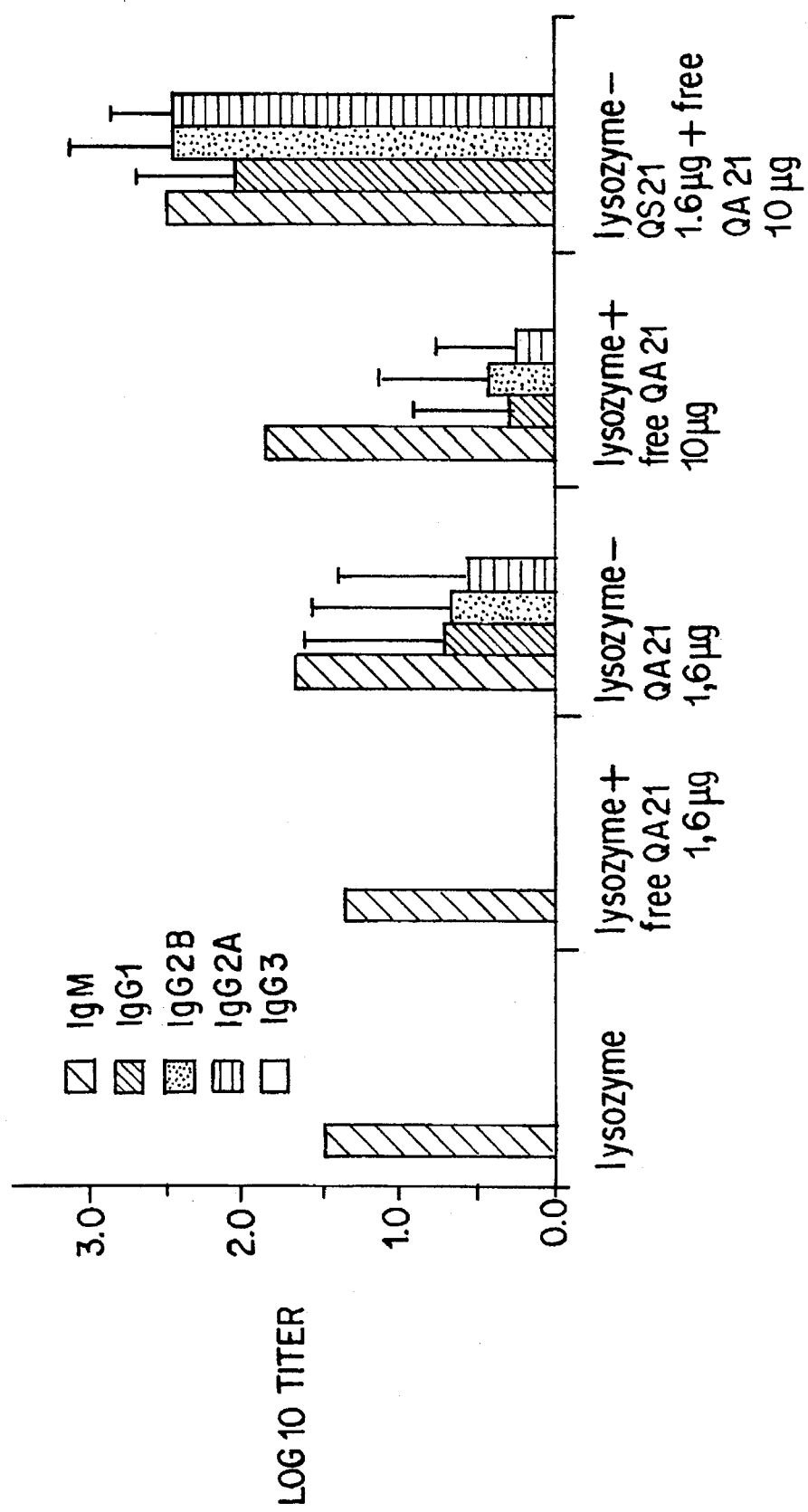
FIG. 22 shows the IgG isotypes produced by each group of mice.

As shown in FIG. 22, only IgM antibodies were produced when lysozyme was used as the immunogen, either alone or with free QA-21. Administration of the lysozyme-QA-21 conjugate led to the production of IgM, IgG1, IgG2B, and IgG2A antibodies. Surprisingly, when the lysozyme-QA-21 conjugate was co-administered with free QA-21 as an Adjuvant, a significant increase in titers for each isotype was obsessed.

EXAMPLE 20

CONJUGATION OF QA-21 TO GLYCINE, ETHYLENE DIAMINE, AND ETHYLAMINE THROUGH QA-21 CARBOXYL GROUP OF GLUCURONIC ACID

Preparation of Active Ester Derivative of QA-21:

Forty mg of QA-21 (approximately 20 μmole) was dissolved in 0.4 ml of dimethylformamide (DMF). Sulfo-N-hydroxysuccinimide (S-NHS, 8.7 mg, 40 μmole) was dissolved in the QA-21 solution. Neither QA-21 nor S-NHS was fully soluble in DMF. A stock solution of DCC (45.3 mg in 0.5 ml of DMF) was prepared. DCC was added to the QA-21 solution according to the following schedule:

| Time | DCC solution |
| --- | --- |
| 0 | 0.05 ml |
| 19.5 h | 0.05 ml |

At 24 hours after the first addition of DCC, the reaction mixture was cooled to 4° C. for 1 h, and filtered through a 0.45 micron filter. A total of 3 ml of ethyl acetate was added to the filtered reaction mixture. A precipitate formed and was collected by centrifugation. Another 3 ml of ethyl acetate was added to wash the precipitate. The precipitate was centrifuged and collected. The wash step with ethyl acetate was repeated. The precipitate was dried in a vacuum dessicator. This precipitate was analyzed by HPLC and shown to be the S-NHS derivative of QA-21. It was utilized in the preparation of the glycine derivative.

To prepare ethylamine and ethylene diamine derivatives of QA-21, the S-NHS QA-21 was prepared identically to that for the glycine reaction except that the reaction size was doubled and 0.300 ml of the DCC solution was added in one aliquot to the QA-21 solution and stirred overnight before the ethyl acetate wash steps.
Preparation of QA-21 linked to glycine via amide bond between QA-21 carboxyl and glycine amino group.:

The S-NHS-QA-21 precipitate was added to 75 mg (1 mmole) of glycine dissolved in 1 ml of 0.1M sodium phosphate, pH 7.0. After two hours of reaction at room temperature, the reaction mixture was loaded on reverse phase HPLC (Vydac C4, 300 angstrom pore size, 5 micron) in a gradient of 30–40% B over 60 minutes. Solvent A was 0.1% Trifluoro-acetic acid in water. Solvent B was 0.1% TFA in acetonitrile. A new peak at 34.30 minutes, not present either in an unmodified QA-21 solution or in the unreacted S-NHS-QA-21 solution, was collected, dried under nitrogen, and freeze-dried. The new product was confirmed by FAB-MS.
Preparation of QA-21 linked via amide bond between QA-21 carboxyl to amino group of ethylene diamine:

To react ethylene diamine with the active ester derivative of QA-21, 266 mg (2 mmole) of ethylenediamine was dissolved in 2.0 ml 0.1M potassium phosphate, pH 7. The pH was readjusted to 7 by addition of NaOH. Final volume was 2.45 ml. Thirty-two mg of S-NHS-QA-21 was added to this solution. The reaction was analyzed by HPLC after 1.5 hours at room temperature and showed the generation of a new peak with a shorter retention time than QA-21. The reaction mixture was stored at 4° C. overnight and then purified by semipreparative HPLC by the same method as for the glycine derivative. The peak at 32.5 minutes was collected, dried under nitrogen to remove acetonitrile, and freeze-dried. This derivative is an example of a linker which could be used to couple QA-21 to antigen. The new product was confirmed by FAB-MS.
Preparation of QA-21 linked via amide bond between QA-21 carboxyl to amino group of ethylamine:

To prepare the ethylamine derivative of QA-21, 70 ml of ethylamine was diluted to 100 ml with water. A total of 0.091 ml of this ethylamine solution was added to 1 ml of 0.1M potassium phosphate, pH 7.0. The pH was readjusted to 7 with phosphoric acid. A total of 32 mg of S-NHS-QA-21 was added to this solution. It was analyzed by HPLC after 45 minutes; a new peak was observed which was more hydrophobic than QA-21. The reaction mixture was stored overnight at 4° C. The mixture was slightly cloudy. It was solubilized with an addition of 0.1 ml acetonitrile. It was injected on HPLC and purified by the same method as for the other two derivatives. The peak at 52.3 minutes was collected, dried under nitrogen to remove acetonitrile, and freeze-dried. The new product was confirmed by FAB-MS.

EXAMPLE 21

CONJUGATION OF QA-21 TO GLYCINE AND ETHYLENE DIAMINE TO QA-21 TRITERPENE ALDEHYDE VIA REDUCTIVE ALKYLATION

Preparation of QA-21 linked to Glycine via Reduction of Schiff's base of QA-21 Triterpene Aldehyde with Amino Group of Glycine:

To react glycine with tile aldehyde on tile QA-21 triterpene, 20 mg of QA-21 was dissolved in 0.8 ml of 50% methanol, 50 mM sodium phosphate, pH 6.0. A 0.5 ml solution of glycine was prepared in water. A total of 0.1 ml of glycine was added to the QA-21 solution. A 0.1M solution of sodium cyanoborohydride was prepared in methanol (32 mg in 5 ml). A total of 0.1 ml of the sodium cyanoborohydride was added to the QA-21 solution. The addition of sodium cyanoborohydride was repeated at 2.5, 21, 25 and 46 hours. The reaction mixture was purified by reverse phase HPLC. A new peak at 31.3 minutes was collected. The new product was confirmed by FAB-MS.
Preparation of QA-21 linked to ethylene diamine via Reduction of Schiff's base of QA-21 Triterpene Aldehyde with Amino Group of Ethylene Diamine:

To react ethylenediamine with the aldehyde on the QA-21 triterpene, 6 mg of QA-21 was dissolved in 1 ml 50% methanol, 20 mM triethylaminephosphate, pH 6. A total of 0.15 ml of a 0.1M ethylenediamine solution in water was added followed by 0.06 ml of 50 mM sodium cyanoborohydride in methanol. Additional aliquots of the sodium cyanoborohydride were added at 45 minutes and 16 hours. The reaction was purified by reverse phase HPLC on a 30–60% B method. A new peak at 19.6 minutes was collected. This material was freeze-dried. The resulting peak was analyzed by reverse phase thin layer chromatography and shown to be reactive with ninhydrin, indicating the addition of a free amino group to QA-21. This derivative is an example of a linker that could be used to couple QA-21 to antigen.

EXAMPLE 22

REDUCTION OF QA-21 TRITERPENE ALDEHYDE TO ALCOHOL

Twelve mg of QA-21 in four ml of water was mixed with 8 ml of 0.1M sodium phosphate, pH 6.0 for a final QA-21 concentration of 1 mg/ml. A stock solution of 1M sodium borohydride was prepared in 0.01M NaOH. A total volume of 0.580 ml of sodium borohydride was added to the QA-21 in small increments (approximately 50 µl increments). The final concentration of sodium borohydride was 0.05M. This reaction mixture was incubated for one hour at room temperature. The reaction was quenched with 1 ml of 1N acetic acid. To remove sodium borohydride the QA-21 was absorbed to $C_{18}$. Four mls of reaction mix was passed through a cartridge containing $C_{18}$. The cartridge was then washed with two 5 ml water washes. The QA-21 was then eluted from the $C_{18}$ with 5 ml of methanol. This process was repeated with the remaining 8 ml of reaction mix. The methanol was evaporated under a stream of $N_2$. The reduced QA-21 was then redissolved in 30% acetonitrile/0.15% trifluoroacetic acid and purified by HPLC to remove residual unreduced QA-21 (Vydac $C_4$, 5 µm particle size, in a gradient of 25–40% B over 60 minutes at a flow rate of 3 ml/min (Solvent A—0.15% TFA in water, Solvent B—0.15% TFA in acetonitrile)). The reduced QA-21 eluted with a retention time of 46.8 minutes (compared to a retention time of 48.1 minutes for unreduced QA-21). The peak corresponding to the reduced QA-21 was pooled, diluted ½ with water and collected on $C_{18}$ cartridges as described above. The final product was lyophilized and used for immunization studies.

EXAMPLE 23

ADJUVANT ACTIVITIES OF MODIFIED QA-21 SAPONINS

Figure 23A:
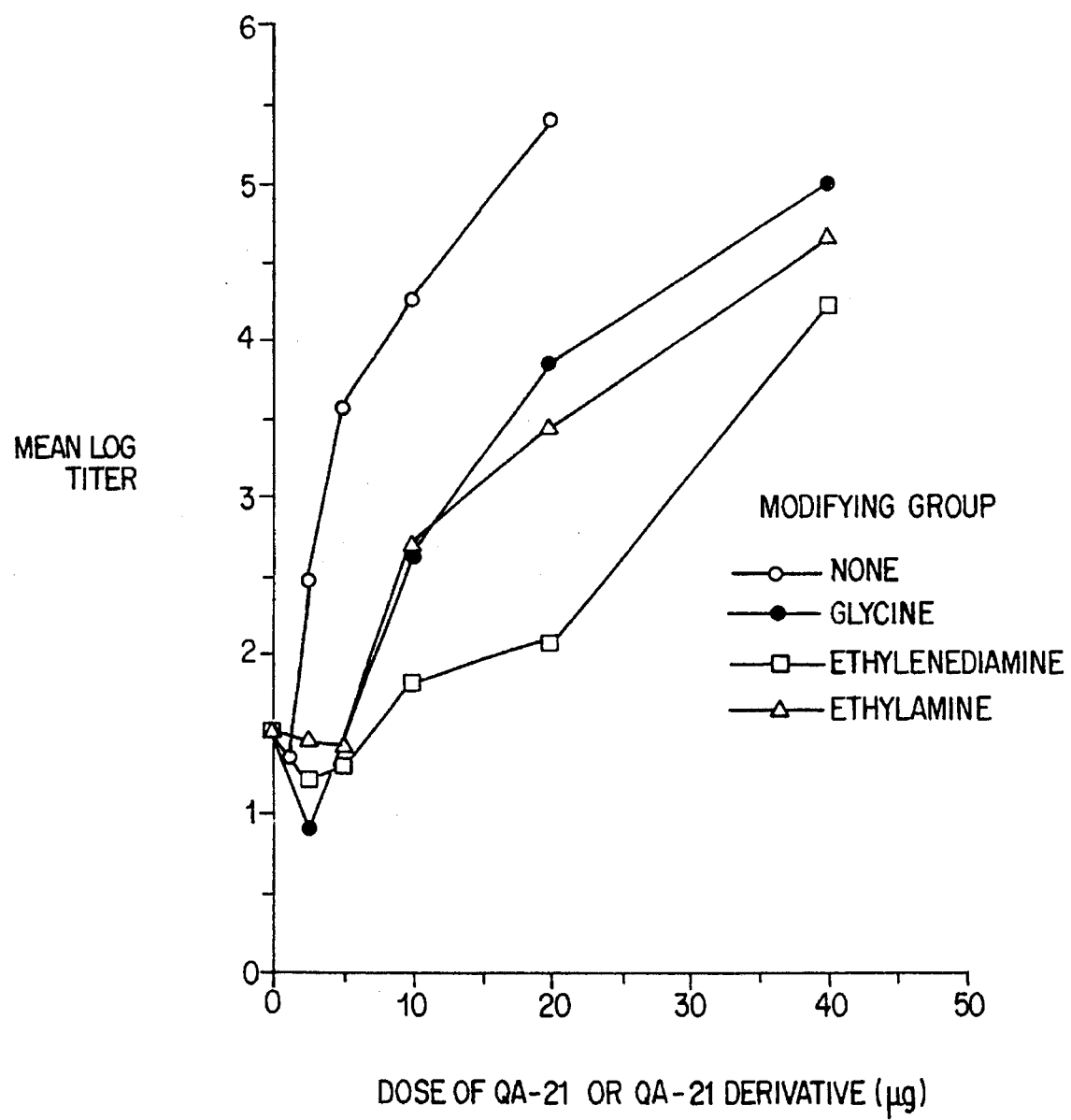
FIG. 23A–23C show the adjuvant activities of modified saponin QA-21 at the glucuronate carboxyl (FIG. 23A), at the triterpene aldehyde through reductive amination (FIG. 23B) and at the triterpene aldehyde through reduction to an alcohol (FIG. 23C).
Figure 23B:
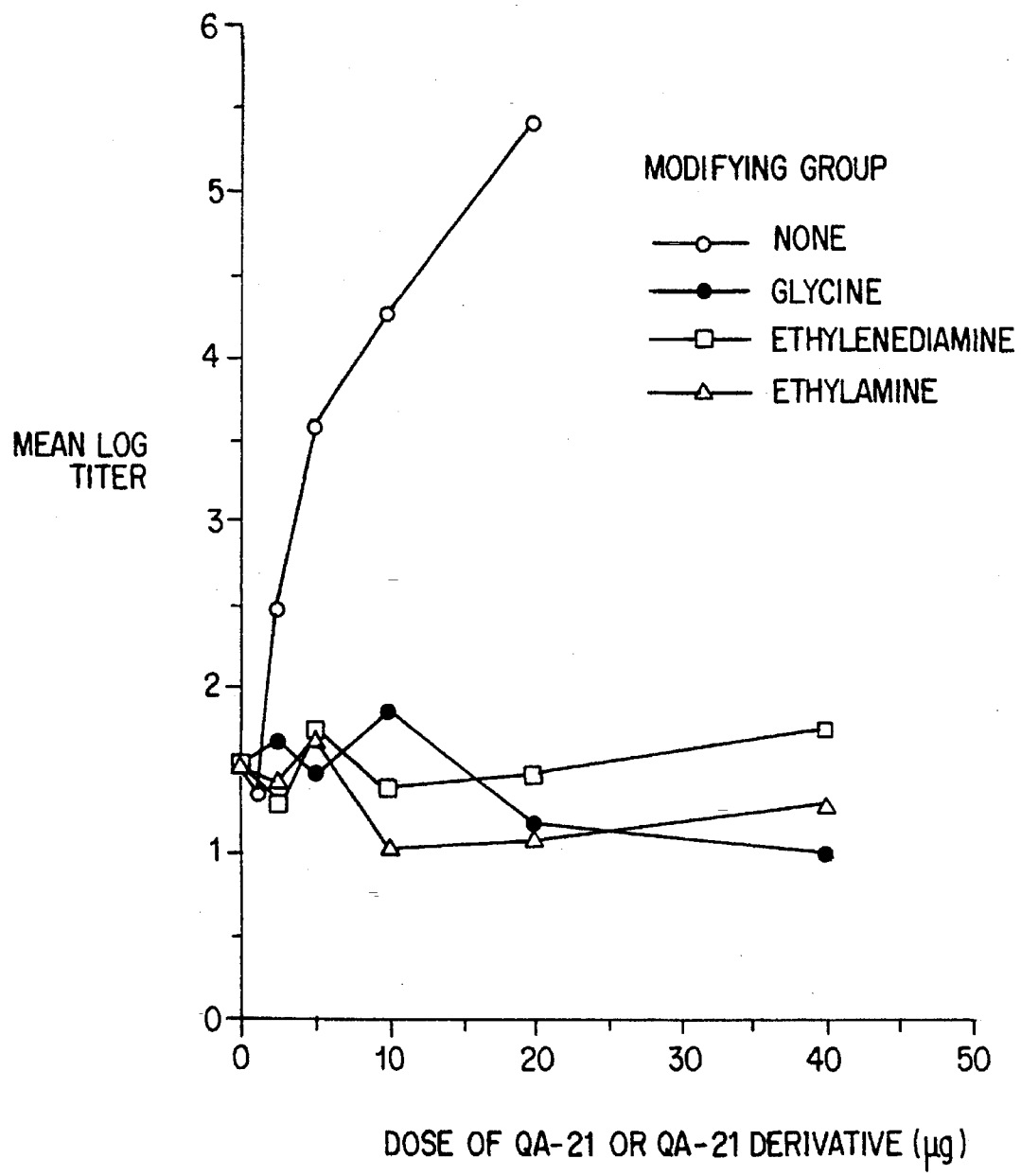
Figure 23C:
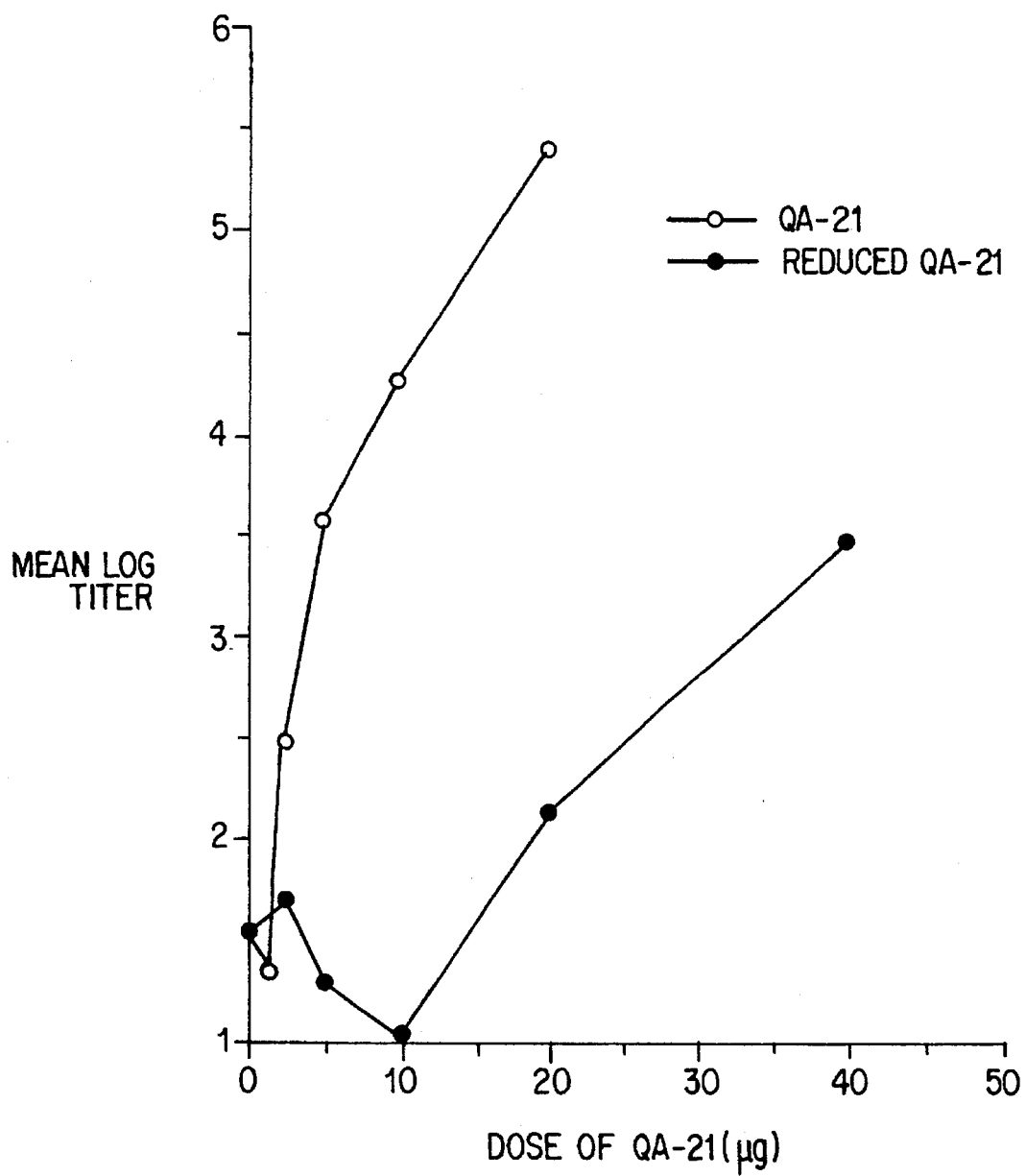

Modified QA-21 saponins, as prepared in Examples 20, 21 and 22, were tested as in Example 11. C57 bl/6 mice (5 per group) were immunized subcutaneously with 25 µg ovalbumin and 10–50 µg QA-21 or one of its derivatives in saline. A booster immunization was given at day 14. Antibody response (total IgG) was tested by enzyme immunoassay after the second immunization. The three derivatives (etnhylamine and ethylene diamine glycine) at the glucuronate carboxyl group were still adjuvant active, although the minimum effective dose was higher than for QA-21 (FIG. 23A). In contrast, derivatives prepared by reductive alkylation at the triterpene aldehyde did not retain adjuvant activity at the doses tested (FIG. 23B). However, the modified QA-21 in which the triterpene aldehyde was reduced to an alcohol retained some adjuvant activity, but with a higher minimum effective dose than QA-21 (FIG. 23C). Results from similar experiments in which two booster immunizations were given at two week intervals are summarized in Table 7.

TABLE 7

Adjuvant Activity of QA-21 and Derivatives

| Saponin (10 µg) administered with ovalbumin (25 µg) | Anti-ovalbumin IgG, Total (log titer) |
| --- | --- |
| none | 2.59 ± 0.81 |
| QA-21 | 4.06 ± 0.30 |
| QA-21-C-ethylamine[a] | 3.78 ± 0.40 |
| QA-21-C-ethylenediamine[a] | 3.15 ± 0.45 |
| QA-21C-glycine[a] | 3.34 ± 0.21 |
| QA-21-A-ethylamine[b] | 2.69 ± 0.59 |
| QA-21-A-ethylene diamine[b] | 2.68 ± 0.36 |
| QA-21-A-glycine[b] | 2.00 ± 0.19 |

[a]Modified at glucuronate carboxyl.
[b]Modified at triterpene aldehyde.

EXAMPLE 24

CONJUGATION OF BIOTIN TO QA-21 THROUGH ETHYLENE DIAMINE LINKING GROUP

Figure 24:
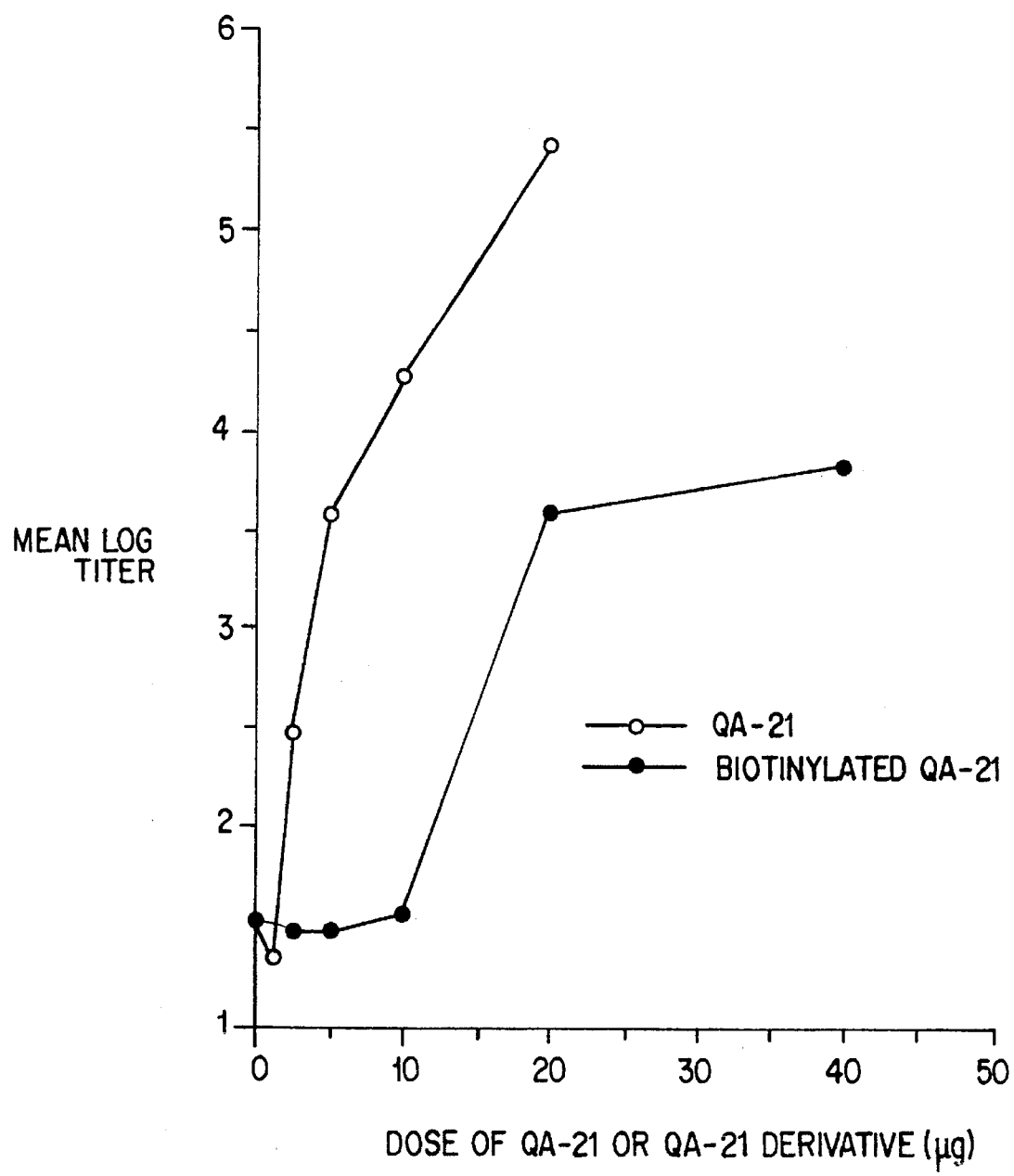
FIG. 24 shows the adjuvant activity of QA-21 linked to biotin through ethylene diamine linked to the glucuronate carboxyl.

A commercially available active ester derivative (S-NHS) of biotin (Pierce) was utilized for this conjugation. The activated biotin was then linked to the free amino group of the ethylene diamine derivative of QA-21 of Example 20. This biotin derivative also retained adjuvant activity (FIG. 24).

The invention now being fully described, it will be apparent to one of ordinary skill in the art that many changes and modifications can be made thereto without departing from the spirit or scope of the invention as set forth below.

What is claimed is:

1. A saponin/antigen covalent conjugate composition or a saponin alkaline hydrolysis product/antigen covalent conjugate composition comprising a substantially pure saponin selected from the group consisting of QA-21-V1 and QA-21-V2, or an alkaline hydrolysis product of a substantially pure saponin selected from the group consisting of QA-21-V1 and QA-21-V2, wherein said saponin or saponin alkaline hydrolysis product comprises a glucuronate carboxyl group, said saponin or said saponin alkaline hydrolysis product being linked at the glucuronate carboxyl group to an antigen either directly or through a linker group, wherein the linkage does not interfere with the ability of said substantially pure saponin or said alkaline hydrolysis product to stimulate an immune response in an animal.

2. The saponin/antigen covalent conjugate of claim 1, wherein said linker group is a bifunctional molecule.

3. The saponin/antigen covalent conjugate of claim 1, wherein said linker group is selected from the group consisting of:

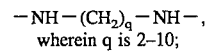
wherein q is 2–10;

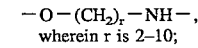
wherein r is 2–10;

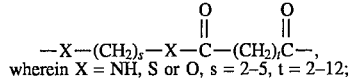
wherein X = NH, S or O, s = 2–5, t = 2–12;

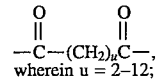
wherein u = 2–12;

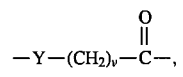

wherein Y is NH or S, v = 1–3; and NH(R)—CH—$CO_2H$, wherein R" is hydrogen, $C_{1-4}$ alkyl, or $C_{1-4}$ alkyl substituted by phenyl, hydroxyphenyl, indolyl, mercapto, $C_{1-4}$ alkylthio, hydroxy, carboxy, amino, guanidino, imidazolyl or carbamyl; or wherein R and R" together form a pyrrolidinyl or piperidinyl ring.

4. The saponin/antigen covalent conjugate of claim 1, wherein said substantially pure saponin is QA-21-V1, which has a retention time of approximately 6.4 minutes on HILIC on a PolyLC PHEA column having 5 µm particle size, 4.6 mm ID×200 mm L in a solvent of 10 mM TEAP, pH 6.0, in water/acetonitrile (15/85%, v/v) at a flow rate of 1 ml/min.

5. The saponin/antigen covalent conjugate of claim 4, wherein said saponin contains about 22% carbohydrate per dry weight, and wherein said carbohydrate has a composition consisting of the following monosaccharides: terminal arabinose, terminal apiose, terminal xylose, 4-rhamnose, terminal galactose, 2-fucose, 3-xylose, and 2,3-glucuronic acid.

6. The saponin/antigen covalent conjugate of claim 1, wherein said substantially pure saponin is QA-21-V2, which has a retention time of approximately 6.9 minutes on HILIC on a PolyLC PHEA column having 5 μm particle size, 4.6 mm ID×200 mm L in a solvent of 10 mM TEAP, pH 6.0, in water/acetonitrile (15/85%, v/v) at a flow rate of 1 ml/min.

7. The saponin/antigen covalent conjugate of claim 6, wherein said saponin contains about 22% carbohydrate per dry weight, and wherein said carbohydrate has a composition consisting of the following monosaccharides: terminal arabinose, two terminal xyloses, 4-rhamnose, terminal galactose, 2-fucose, 3-xylose, and 2,3-glucuronic acid.

8. A vaccine which comprises a saponin/antigen covalent conjugate composition or a saponin alkaline hydrolysis product/antigen covalent conjugate composition and a pharmaceutically acceptable carrier, wherein said conjugate comprises a substantially pure saponin selected from the group consisting of QA-21-V1 and QA-21-V2, or an alkaline hydrolysis product of a substantially pure saponin selected from the group consisting of QA-21-V1 and QA-21-V2, wherein said saponin or saponin alkaline hydrolysis product comprises a glucuronate carboxyl group, said saponin or said saponin alkaline hydrolysis product being linked at the glucuronate carboxyl group to an antigen either directly or through a linker group, wherein the linkage does not interfere with the ability of said substantially pure saponin or said alkaline hydrolysis product to stimulate an immune response in an animal.

9. The vaccine of claim 8, wherein said linker group is a bifunctional molecule.

10. The vaccine of claim 8, wherein said linker group is selected from the group consisting of:

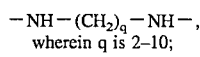
wherein q is 2–10;

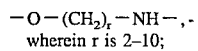
wherein r is 2–10;

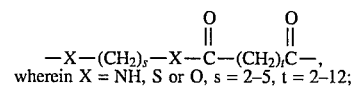
wherein X = NH, S or O, s = 2–5, t = 2–12;

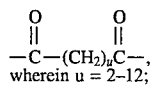
wherein u = 2–12;

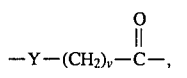
wherein Y is NH or S, v = 1–3; and NH(R)—CH—CO$_2$H, wherein R" is hydrogen, $C_{1-4}$alkyl, or $C_{1-4}$ alkyl substituted by phenyl, hydroxyphenyl, indolyl, mercapto, $C_{1-4}$ alkylthio, hydroxy, carboxy, amino, guanidino, imidazolyl or carbamyl; or wherein R and R" together form a pyrrolidinyl or piperidinyl ring.

11. The vaccine of claim 8, wherein said substantially pure saponin is QA-21-V1, which has a retention time of approximately 6.4 minutes on HILIC on a PolyLC PHEA column having 5 μm particle size, 4.6 mm ID×200 mm L in a solvent of 10 mM TEAP, pH 6.0, in water/acetonitrile (15/85 %, v/v) at a flow rate of 1 ml/min.

12. The vaccine of claim 11, wherein said saponin contains about 22% carbohydrate per dry weight, and wherein said carbohydrate has a composition consisting of the following monosaccharides: terminal arabinose, terminal apiose, terminal xylose, 4-rhamnose, terminal galactose, 2-fucose, 3-xylose, and 2,3-glucuronic acid.

13. The vaccine of claim 8, wherein said substantially pure saponin is QA-21-V2, which has a retention time of approximately 6.9 minutes on HILIC on a PolyLC PHEA column having 5 μm particle size, 4.6 mm ID×200 mm L in a solvent of 10 mM TEAP, pH 6.0, in water/acetonitrile (15/85 %, v/v) at a flow rate of 1 ml/min.

14. The vaccine of claim 13, wherein said saponin contains about 22% carbohydrate per dry weight, and wherein said carbohydrate has a composition consisting of the following monosaccharides: terminal arabinose, two terminal xyloses, 4-rhamnose, terminal galactose, 2-fucose, 3-xylose, and 2,3-glucuronic acid.

15. The vaccine of claim 8, further comprising an adjuvant.

16. The vaccine of claim 15, wherein said adjuvant is a saponin.

17. A method of enhancing an immune response to an antigen in an individual comprising administration of an effective amount of a saponin/antigen covalent conjugate composition or a saponin alkaline hydrolysis product/antigen covalent conjugate composition and a pharmaceutically acceptable carrier, wherein said conjugate comprises a substantially pure saponin selected from the group consisting of QA-21-V1 and QA-21-V2, or an alkaline hydrolysis product of a substantially pure saponin selected from the group consisting of QA-21-V1 and QA-21-V2, wherein said saponin or saponin alkaline hydrolysis product comprises a glucuronate carboxyl group, said saponin or said saponin alkaline hydrolysis product being linked at the glucuronate carboxyl group to an antigen either directly or through a linker group, wherein the linkage does not interfere with the ability of said substantially pure saponin or said alkaline hydrolysis product to stimulate an immune response in an animal.

18. The method of enhancing an immune response of claim 17, wherein said linker group is a bifunctional molecule.

19. The method of enhancing an immune response of claim 17, wherein said linker group is selected from the group consisting of:

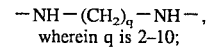
wherein q is 2–10;

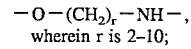
wherein r is 2–10;

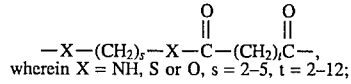
wherein X = NH, S or O, s = 2–5, t = 2–12;

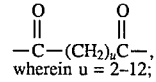
wherein u = 2–12;

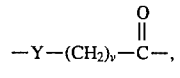
wherein Y is NH or S, v = 1–3; and NH(R)—CH—CO$_2$H, wherein R" is hydrogen, $C_{1-4}$alkyl, or $C_{1-4}$ alkyl substituted by phenyl, hydroxyphenyl, indolyl, mercapto, $C_{1-4}$ alkylthio, hydroxy, carboxy, amino, guanidino, imidazolyl or carbamyl; or wherein R and R" together form a pyrrolidinyl or piperidinyl ring.

20. The method of claim 17, wherein said substantially pure saponin is QA-21-V1, which has a retention time of approximately 6.4 minutes on HILIC on a PolyLC PHEA column having 5 μm particle size, 4.6 mm ID×200 mm L in a solvent of 10 mM TEAP, pH 6.0, in water/acetonitrile (15/85 %, v/v) at a flow rate of 1 ml/min.

21. The method of claim 20, wherein said saponin contains about 22% carbohydrate per dry weight, and wherein said carbohydrate has a composition consisting of the following monosaccharides: terminal arabinose, terminal apiose, terminal xylose, 4-rhamnose, terminal galactose, 2-fucose, 3-xylose, and 2,3-glucuronic acid.

22. The method of claim 17, wherein said substantially pure saponin is QA-21-V2, which has a retention time of approximately 6.9 minutes on HILIC on a PolyLC PHEA column having 5 μm particle size, 4.6 mm ID×200 mm L in a solvent of 10 mM TEAP, pH 6.0, in water/acetonitrile (15/85 %, v/v) at a flow rate of 1 ml/min.

23. The method of claim 22, wherein said saponin contains about 22% carbohydrate per dry weight, and wherein said carbohydrate has a composition consisting of the following monosaccharides: terminal arabinose, two terminal xyloses, 4-rhamnose, terminal galactose, 2-fucose, 3-xylose, and 2,3-glucuronic acid.

24. The method of claim 19, further comprising administering an adjuvant to said individual.

25. The method of claim 24, wherein said adjuvant is a saponin.

26. The method of claim 19, wherein said individual is an animal.

27. The method of claim 19, wherein said individual is a human.

28. Substantially pure QA-21-V 1 saponin, wherein said pure saponin is characterized by a peak at 6.4 minutes on HILIC on a PolyLC PHEA column having 5 μm particle size, 4.6 mm ID×200 mm L in a solvent of 10 mM TEAP, pH 6.0, in water/acetonitrile (15/85 %, v/v) at a flow rate of 1 ml/min.

29. The substantially pure QA-21-V 1 saponin of claim 28, wherein said saponin contains about 22% carbohydrate per dry weight, and wherein said carbohydrate has a composition consisting of the following monosaccharides: terminal arabinose, terminal apiose, terminal xylose, 4-rhamnose, terminal galactose, 2-fucose, 3-xylose, and 2,3-glucuronic acid.

30. Substantially pure QA-21-V2 saponin, wherein said pure saponin is characterized by a peak at 6.9 minutes on HILIC on a PolyLC PHEA column having 5 μm particle size, 4.6 mm ID×200 mm L in a solvent of 10 mM TEAP, pH 6.0, in water/acetonitrile (15/85 %, v/v) at a flow rate of 1 ml/min.

31. The substantially pure QA-21-V2 saponin of claim 30, wherein said saponin contains about 22% carbohydrate per dry weight, and wherein said carbohydrate has a composition consisting of the following monosaccharides: terminal arabinose, two terminal xyloses, 4-rhamnose, terminal galactose, 2-fucose, 3-xylose, and 2,3-glucuronic acid.

32. A method of enhancing an immune response to an antigen in an individual comprising administration of the substantially pure saponin adjuvant of any one of claims 28–31 and an immunologically effective amount of an antigen to said individual in an amount sufficient to enhance the immune response of said individual to said antigen.

33. A pharmaceutical composition useful for inducing the production of antibodies to an antigen in an individual comprising an immunogenically effective amount of an antigen and at least one substantially pure saponin of any one of claims 28–31, wherein said substantially pure saponin is present in an amount sufficient to enhance the immune response of said individual to said antigen.

34. The pharmaceutical composition of claim 33 wherein said individual is a mammal.

35. A substantially pure modified saponin comprising:
1) a saponin selected from the group consisting of QA-21-V 1 and QA-2 1-V2, wherein said saponin comprises a glucuronate carboxyl group; and
2) a linking group or blocking group covalently attached at said glucuronate carboxyl group, wherein said substantially pure modified saponin retains the ability to stimulate an immune response in an animal.

36. The substantially pure modified saponin of claim 35, wherein said blocking group is ethylamine.

37. The substantially pure modified saponin of claim 35, wherein said linking group is bifunctional.

38. The substantially pure modified saponin of claim 35, wherein said linking group is selected from the group consisting of:

$$-NH-(CH_2)_q-NH-,$$
wherein q is 2–10;

$$-O-(CH_2)_r-NH-,$$
wherein r is 2–10;

$$-X-(CH_2)_s-X-\overset{O}{\underset{\|}{C}}-(CH_2)_t\overset{O}{\underset{\|}{C}}-,$$
wherein X = NH, S or O, s = 2–5, t = 2–12;

$$-\overset{O}{\underset{\|}{C}}-(CH_2)_u\overset{O}{\underset{\|}{C}}-,$$
wherein u = 2–12;

$$-Y-(CH_2)_v-\overset{O}{\underset{\|}{C}}-,$$
wherein Y is NH or S, v = 1–3; and $NH(R)-\underset{\underset{R''}{|}}{CH}-CO_2H$, wherein R" is hydrogen, $C_{1-4}$ alkyl, or $C_{1-4}$ alkyl substituted by phenyl, hydroxyphenyl, indolyl, mercapto, $C_{1-4}$ alkylthio, hydroxy, carboxy, amino, guanidino, imidazolyl or carbamyl; or wherein R and R" together form a pyrrolidinyl or piperidinyl ring.

39. The substantially pure modified saponin of claim 38, wherein said linking group is ethylene diamine.

40. The substantially pure modified saponin of claim 38, wherein said linking group is glycine.

41. Substantially pure modified saponin QA-7 which is reduced to an alcohol group at the triterpine aldehyde.

42. The substantially pure modified saponin of any of claims 35–40 in which the saponin is QA-7.

43. The substantially pure modified saponin of any of claims 35–40 in which the saponin is QA-17.

44. The substantially pure modified saponin of any of claims 35—40 in which the saponin is QA-18.

45. The substantially pure modified saponin of any of claims 35–40 in which the saponin is QA-21.

46. The substantially pure modified saponin of any of claims 35–40 in which the saponin is QA-21-V1.

47. The substantially pure modified saponin of any of claims 35–40 in which the saponin is QA-2 1-V2.

48. A method of enhancing an immune response to an antigen in an individual comprising administering the substantially pure modified saponin adjuvant of any one of claims 35–41 by any suitable means, or administering parenterally, intravenously, intramuscularly or subcutaneously an antigen and at least one substantially pure modified saponin selected from the group consisting QA-18, QA-21, QA-21-V1 and QA-21-V2 which is reduced to an alcohol group at the triterpine aldehyde, to said individual in an amount sufficient to enhance the immune response of said individual to said antigen.

49. A pharmaceutical composition useful of inducing the production of antibodies to an antigen in an individual comprising an immunogenically effective amount of an antigen and at least one substantially pure modified saponin of any one of claims 35–41 administered by any suitable means, or an antigen and at least one substantially pure modified saponin selected from the group consisting QA-18, QA-21, QA-21-V1 and QA-21-V2 which is reduced to an alcohol group at the triterpine aldehyde which is administered parenterally, intravenously, intramuscularly or subcutaneously wherein said substantially pure modified saponin is present in an amount sufficient to enhance the immune response of said individual to said antigen.

50. The pharmaceutical composition of claim 49 wherein said individual is a mammal.

* * * * *